US008927808B2

(12) United States Patent
Rommens et al.

(10) Patent No.: US 8,927,808 B2
(45) Date of Patent: Jan. 6, 2015

(54) POTYVIRUS RESISTANCE IN POTATO

(75) Inventors: Caius Rommens, Boise, ID (US); Hui Duan, Boise, ID (US); Rekha Chawla, Boise, ID (US)

(73) Assignee: J.R. Simplot Company, Boise, ID (US)

( * ) Notice: Subject to any disclaimer, the term of this patent is extended or adjusted under 35 U.S.C. 154(b) by 189 days.

(21) Appl. No.: 13/275,897

(22) Filed: Oct. 18, 2011

(65) Prior Publication Data

US 2012/0102589 A1 Apr. 26, 2012

Related U.S. Application Data

(60) Provisional application No. 61/394,081, filed on Oct. 18, 2010, provisional application No. 61/482,579, filed on May 4, 2011.

(51) Int. Cl.

*C12N 15/82* (2006.01)
*C12N 15/87* (2006.01)
*A01H 1/00* (2006.01)
*A01H 5/04* (2006.01)
*C07K 14/415* (2006.01)
*A23L 1/216* (2006.01)
*A23L 1/212* (2006.01)

(52) U.S. Cl.

CPC .............. *C12N 15/8283* (2013.01); *A01H 5/04* (2013.01); *C07K 14/415* (2013.01); *A23L 1/216* (2013.01); *A23L 1/212* (2013.01)

USPC .......................................... 800/279; 800/294

(58) Field of Classification Search

None

See application file for complete search history.

(56) References Cited

U.S. PATENT DOCUMENTS

2005/0255455 A1 11/2005 Caranta et al.
2008/0148432 A1 * 6/2008 Abad ............................ 800/279

FOREIGN PATENT DOCUMENTS

WO WO 03/066900 A2 8/2003
WO WO 2010/048398 A2 4/2010
WO WO 2010048398 A2 * 4/2010 ............... A01H 5/00

OTHER PUBLICATIONS

Jones et al. Government of Western Austrialia Department of Agriculture Potato Virus Y Factsheet. 2003. No. 02/2003. ISSN 1443-7783. p. 1-2.* van der Vossen et al. An ancient R gene from the wild potato species *Solanum bulbocastanum* confers broad-specturm resistance to *Phytophthora infestans* in cultivated potato and tomato. 2003. Plant Journal. 36:867-882.*

Ruffel et al.The recessive potyvirus resistance gene pot-1 is the tomato orthologue of the pepper pvr2-elF4E gene. 2005. Mol. Gen. Genomics. 274:346-353.*

PCT International Search Report, dated Mar. 2, 2012, 3 pages, PCT Application No. PCT/US2011/056690.

The First Examination Report received in the related Australian Patent Application 610767, dated Sep. 20, 2013.

* cited by examiner

*Primary Examiner* — Cathy Kingdon Worley
*Assistant Examiner* — Jeffrey Bolland
(74) *Attorney, Agent, or Firm* — Cooley LLP

(57) ABSTRACT

The present invention is drawn to novel genes from wild plants, such as wild potato and pepper plants, that confer potyvirus resistance to plants, such as in transformed cultivated plants. Also encompassed are cultivated plants transformed with the novel gene, food products made from the transformed cultivated plants, and methods for making such plants and food products.

21 Claims, 12 Drawing Sheets

FIG. 1

```
pvr1, pepper          MATAEMEKTTTFDE------AEKVKL---NANEADDEVEEGEIVEETDD--TTSYLSK---
pvr1-1, pepper        MATAEMEKTTTFDE------AEKVKL---NANEADDEVEEGEIVEETDD--TTSYLSK---
pvr1-2, pepper        MATAEMEKTTTFDE------AEKVKL---NANEADDEVEEGEIVEETDD--TTSYLSK---
pvr2-3, pepper        MATAEMEKTTTFDE------AEKVKL---NANEADDEVEEGEIVEETDD--TTSYLSK---
pvr2-4, pepper        MATAEMEKTTTFDE------AEKVKL---NANEADDEVEEGEIVEETDD--TTSYLSK---
pvr2-5, pepper        MATAEMEKTTTFDE------AEKVKL---NANEADDEVEEGEIVEETDD--TTSYLSK---
pvr2-6, pepper        MATAEMEKTTTFDE------AEKVKL---NANEADDEVEEGEIVEETDD--TTSYLSK---
pvr2-7, pepper        MATAEMEKTTTFDE------AEKVKL---NANEADDEVEEGEIVEETDD--TTSYLSK---
pvr2-8, pepper        MATAEMEKTTTFDE------AEKVKL---NANEADDEVEEGEIVEETDD--TTSYLSK---
pvr2-9, pepper        MATAEMEKTTTFDE------AEKVKL---NANEADDEVEEGEIVEETDD--TTSYLSK---
pot1, tomato          MAAAEMERTMSFDA------AEKLKAADGGGEVDDELEEGEIVEESND--TASYLGK---
pot1, wild tomato     MAAAEMERTMSFDA------AEKLKAADGGGEVDDELEEGEIVEESND--TASYLGK---
mo1, lettuce          MKSERQ-KLIDVNK-------HRGVKAD-----GEEDEQLEEGEIVEED----ADTLS---SS
mo2, lettuce          MKSERQ-KLIDVNK-------HRGVKED-----GEEDEQLEEGEIVGED----ADTLS---SS
sbm1-1, pea           MVVEETPKSIITDD---------QITTSP-NPVIEDDNNLEEGEILDEDD--SSATSKP---
sbm1-2, pea           MVVEETPKSIITDD---------QITTSP-NPVIEDDNNLEEGEILDEDD--SSATSKP---
bc3, bean             ---------ESTITDE---------Q----NP-SKVDNDDDDLEDGEILEDADDAASAASKPPSA
nsv, melon            MVVEDSMKATSAEDLANSIANQ---NPRGRGGDEDEELEEGEIVGDDDLDSSNLS---AS
rym4, barley          MA----EDTETRPA-----SAGA------------EEEEEGEIADDGDG--EAAAAAG---
rym5, barley          MA----EDTETRPA-----SAGA------------EERREGEIADDGDG--EAAAAAG---

pvr1, pepper          EIAAK-------HPLEHSWTFWFDNTVAKSKQAAWGS-SLRNVYTFSTVEDFWGAYNNIHH
pvr1-1, pepper        EIATK-------HPLEHSWTFWFDNPEAKSKQAAWGS-SLRNVYTFSTVEDFWGAYNNIHH
pvr1-2, pepper        EIATK-------HPLEHSWTFWFDNPEAKSKQAAWGS-SLRNVYTFSTVEDFWGAYNNIHH
pvr2-3, pepper        EIATK-------HPLEHSWTFWFDNPEAKSKQAAWGS-SLRNVYTFSTVEDFWGAYNNIHH
pvr2-4, pepper        EIATK-------HPLEHSWTFWFDNPEAKSKQAAWGS-SLRNVYTFSTVEDFWGAYNNIHH
pvr2-5, pepper        EIATK-------HPLEHSWTFWFDNTEAKSKQDAWGS-SLRNVYTFSTVEDFWGAYNNIHH
pvr2-6, pepper        EIATK-------HPLEHSWTFWFDNPVEKSKQDDWGS-SLRNVYTFSTVEDFWGAYNNIHH
pvr2-7, pepper        EIATK-------HPLEHSWTFWFDNPEAKSKQAAWGS-SLRNVYTFSTVEDFWGAYNNIHH
pvr2-8, pepper        EIATK-------HPLEHSWTFWFDNPVEKSKQAAWGS-SLRNVYTFSTVEDFWGAYNNIHH
pvr2-9, pepper        EIATK-------HPLEHSWTFWFDNPVKASKQDAWGS-SLRNVYTFSTVEDFWGAYNNIHH
pot1, tomato          EITVK-------HPLEHSWTFWFDKSTTKSRQTEWGS-SLRNLFTFSTVEDFWGAYNNIHH
mo1, lettuce          SSSRPSTAIAQHPLEHSWTFWFDTPSEEGKQVAWGS-SHRPIYTFSSVEEFWSLYNNIHR
mo2, lettuce          SSSRPGTAIAQHPLEHSWTFWFDTPSAKSKQVAWGS-SHRPIYTFSSVEEFWSLYNNIHR
sbm1-1, pea           VVNQP-------HLLEHSWTFLFDTPAAKSKQDDWGSS-HRPIYTFSTVEEFWSIYNNIHH
sbm1-2, pea           VVNQP-------HLLEHSWTFWFDTPAAKSKQEEWGS--HRPIYTFSTVEEFWSIYNNIHH
bc3, bean             FLKEP-------HPLEHSWTFWYDNPSAKSKQASWGS-SIRPIYTFSTVEEFWSIYNNIHH
nsv, melon            LVNQP-------HPLEHSWTFWFDNPSAKSKQATWGA-SIRPIYTFSTVEDFWGVYNNIHH
rym4, barley          KVSA--------HPLENAWTFWFDNTQGKFRAVAWGS-TIHPIHTFSTVEDFWSLYNNIHH
rym5, barley          KVSA--------HPLENAWTFWFDNPQGKSRAVAWGS-TIHPIHTFSTVEDFWSLYNNIHH

pvr1, pepper          PSKLVV--SADLHCFKHKIEPKWEDPVCANGGTWKMSFSKGKSDTSWLYTLLAMIGHQFD
pvr1-1, pepper        PSKLVV--GADLHCFKHKIEPKWEDPVCANGGTWKMSFSKGKSDTSWLYTLLAMIGHQFD
pvr1-2, pepper        PSKLVV--GANLHCFKHKIEPKWEDPVCANGGTWKMSFSKGKSDTSWLYTLLAMIGHQFD
pvr2-3, pepper        PSKLVV--GADLHCFKHKIEPKWEDPVCANGGTWKMSFSKGKSDTSWLYTLLAMIGHQFD
pvr2-4, pepper        PSKLVV--GADLHCFKHKIEPKWEDPVCANGGTWKMSFSKGKSDTSWLYTLLAMIGHQFD
pvr2-5, pepper        PSKLVV--GADLHCFKHKIEPKWEDPVCANGGTWKMSFSKGKSDTSWLYTLLAMIGHQFD
pvr2-6, pepper        PSKLVV--GADLHCFKHKIEPKWEDPVCANGGTWKMSFSKGKSDTSWLYTLLAMIGHQFD
pvr2-7, pepper        PSKLVV--GADLHCFKHKIEPKWEDPVCANGGTWKMSFSKGKSDTSWLYTLLAMIGHQFD
pvr2-8, pepper        PSKLVV--SADLHCFKHKIEPKWEDPVCANGGTWKMSFSKGKSDTSWLYTLLAMIGHQFD
pvr2-9, pepper        PSKLVV--GADLHCFKHKIEPKWEDPVCANGGTWKMSFSKGKSDTSWLYTLLAMIGHQFD
pot1, tomato          PSKLII--GADFHCFKNKIEPKWEDPVCANGGTWKMSFSKGKSDTSWLYTLLAMIGHQFD
mo1, lettuce          PSKLAQGA--DFYCFKNKIEPKWEDPVCANGGKWTMTFTKAKSDTCWLYTLLAMIGEQFD
mo2, lettuce          PSKLAN----DFYCFKNKIEPKWEDPVCANGGKWTMTFTKAKSDTCWLYTLLAMIGEQFD
sbm1-1, pea           PGKLAV--RADFYCFKHKIEPKWEDPICANGGKWTANYPKGKSDTSWLYTLLAMIGEQFD
sbm1-2, pea           PGKLAV--GADFYCFKHKIEPKWEDPICANGGKWTANYPKGKSDTSWLYTLLAMIGEQFD
bc3, bean             PSKLGV--GAGFHCFKNKIEPKWEDPICANGGKWTMTFQRGKSDTSWLYTLLAMIGEQFD
nsv, melon            PSKLAM--RADLYCFKHKIEPKWEDPVCANGGKWTVNFPRGKSDNGWLYTLLAMIGEQFD
rym4, barley          PSKLNV--GADFHCFKDKIEPKWEDPICANGGTWTISCGRGKSDTFWLHTLLALIGEQFD
rym5, barley          PSKLNV--GADFHCFKDKIEPKWEDPICANGGKWTISCGKGKSDTFWLHTLLALIGEQFD

pvr1, pepper          HEDEICGAVVSVRGKGEKISLWTKNAANETAQVSIGKQWKQFLDYSDSVGFIFHDDAKRL
pvr1-1, pepper        HEDEICGAVVSVRGKGEKISLWTKNAANETAQVSIGKQWKQFLDYSDSVGFIFHDDAKRL
pvr1-2, pepper        HEDEICGAVVSVRGKGEKISLWTKNAANETAQVSIGKQWKQFLDYSDSVGFIFHDDAKRL
pvr2-3, pepper        HEDEICGAVVSVRGKGEKISLWTKNAANETAQVSIGKQWKQFLDYSGSVGFIFHDDAKRL
pvr2-4, pepper        HEDEICGAVVSVRGKGEKISLWTKNAANETAQVSIGKQWKQFLDYSDSVGFIFHDDAKRL
pvr2-5, pepper        HEDEICGAVVSVRGKGEKISLWTKNAANETAQVSIGKQWKQFLDYSDSVGFIFHDDAKRL
pvr2-6, pepper        HEDEICGAVVSVRGKGEKISLWTKNAANETAQVSIGKQWKQFLDYSGSVGFIFHDDAKRL
```

FIG. 1 (continued)

```
pvr2-7, pepper      HEDEICGAVVSVRGKGEKISLWTKNAANETAQVSIGKQWKQFLDYSGSVGFIFHDDAKRL
pvr2-8, pepper      HEDEICGAVVSVRGKGEKISLWTKNAANETAQVSIGKQWKQFLDYSDSVGFIFHDDAKRL
pvr2-9, pepper      HEDEICGAVVSVRGRGEKISLWTKNAANETAQVSIGKQWKQFLDYSGSVGFIFHDDAKRL
pot1, tomato        HGDEICGAVVSVRAKGEKIALWTKNAANETAQVSIGKQWKQFLDYSDSVGFIFHDDAKRL
mo1, lettuce        HGEDICGAVVNVRARQEKIALWTKNAANESAQLSIGKQWKEFIDYNDTIGFIFHEDAKTL
mo2, lettuce        HGEDICGAVVNVRARQEKIALWTKNSANESAQLSIGKQWKEFIDYNDTIGFIFHEDAKTL
sbm1-1, pea         NGDEICGAVVKVRGRAEKISIWTKNASNEAAQVSIGKQWKEFLDYNETMGFIFHDDARKL
sbm1-2, pea         NGDEICGAVVNVRGRAEKISIWTKNASNEAAQVSIGKQWKEFLDYNETMGFIFHDDARKL
bc3, bean           YGDEICGAVVNVRNRQDKISIWTKNASNEAAQMSIGKQWKEFLDYNEPIGFIFHEDAKKH
nsv, melon          CGDEICGAVVNVRSGQDKISIWTKNASNEAAQASIGKQWKEFLDYNESIGFIFHDDAKKF
rym4, barley        FGDEICGAVVSVRKNQERVAIWTKNAANETAQISIGKQWKEFLDYKDSIGFVVHEDAKRS
rym5, barley        FGDEICGAVVSVRKDERRVAIWTKNAANETAQISIGKQWKEFLDYKDSIGFVVHEDAKRS

pvr1, pepper        DRNAKNRYTV
pvr1-1, pepper      DRNAKNRYTV
pvr1-2, pepper      DRNAKNRYTV
pvr2-3, pepper      DRNAKNRYTV
pvr2-4, pepper      DRNAKNRYTV
pvr2-5, pepper      NRNAKNRYTV
pvr2-6, pepper      DRNAKNRYTV
pvr2-7, pepper      DRNAKNRYTV
pvr2-8, pepper      DRNAKNRYTV
pvr2-9, pepper      DRNAKNRYTV
pot1, tomato        DRSAKNRYTV
mo1, lettuce        DRSAKNKYTV
mo2, lettuce        DRSAKNKYTV
sbm1-1, pea         DKNAKNKYVV
sbm1-2, pea         DKNAKNKYVV
bc3, bean           ER--------
nsv, melon          DKLAKNKYMV
rym4, barley        DKGAKNRYTV
rym5, barley        DKDAKNRYTV
```

FIGURE 2

```
Potato EIF4E allele 1        MAAAEMERTTSFDAADKLKAADAGGGEVDDELEEGEIVEESNDTASYLGKEITVKHPLEH
Potato EIF4E allele 2        MAAAEMERTTSFDAAEKLKAADAGGGEVDDELEEGEIVEESNDTASYLGKEITVKHPLEH
Wild potato EIF4E pwp1       MAAAEMERTTSFDAAEKLKAADAGGGEVDDELEEGEIVEESNDAASYLGKEITVKHPLEH
Wild potato EIF4E pwp2       MAAAEMERTMSFDAAEKLKAADGGGGEVDDELEEGEIVEESNDTASFLGKEITVKHPLEH
Potato EIF4E allele 1        SWTFWFDSPIAKSRQTAWGSSLRNVYTFSTVEDFWGAYNNIHHPSKLVMGADFHCFKHKI
Potato EIF4E allele 2        SWTFWFDSPIAKSRQTAWGSSLRNVYTFSTVEEFWGAYNNIHHPSKLVMGADFHCFKHKI
Wild potato EIF4E pwp1       SWTFWFDNPTARSRQIDWGSSLRNVYTFSTVEDFWGAYNNIHHPSKLVMGADFHCFKHKI
Wild potato EIF4E pwp2       SWTFWFDSPIAKSRQTAWGSSLRNVYTFSTVEDFWGAYYNIHHPSKLVMGADFHCFKHKI

Potato EIF4E allele 1        EPKWEDPVCANGGTWKMSFSKGKSDTSWLYTPLAMIGHQFDHGDEICGAVVSVRAKGEKI
Potato EIF4E allele 2        EPKWEDPVCANGGTWKMSFLKGKSDTSWLYTLLAMIGHQFDHGDEICGAVVSVRSKGEKI
Wild potato EIF4E pwp1       EPKWEDPICSNGGTWKMSFSKGKSDTSWLYTLLAMIGHQFDHGDEICGAVVNVRVKGEKI
Wild potato EIF4E pwp2       EPKWEDPVCANGGTWKMSFPKGKSDTSWLYTLLAMIGHQFDHGDEICGAVVSVRAKGEKI

Potato EIF4E allele 1        ALWTKNAANETAQVSIGKQWKQFLDYSDSVGFIFHDDAKRLDRNAKNRYTV
Potato EIF4E allele 2        ALWTKNAANETAQVSIGKQWKQFLDHSDSVGFIFHDDAKRLDRSAKNRYTV
Wild potato EIF4E pwp1       ALWTKNAANETAQVSIGKQWKQFLDYSDSVGFIFHDDAKRLDRNAKNRYTV
Wild potato EIF4E pwp2       ALWTKNAANETAQVSIGKQWKQFLDYSDSVGFIFHDDAKRLDRNAKNRYTV
```

FIG. 3

```
pmp1, potato     MAAAEMEATTSFDA------AEKLKAADAGGGEVDDELEEGEIVEESND--AASYLGK---
pmp2, potato     MAAAEMERTQSFDA------AEKLKAADAGGGEVDDELEEGEIVEESND--TASYLGK---
pvr1, pepper     MATAEMEKTTTFDE------AEKVKL---NANEADDEVEEGEIVEETDD--TTSYLSK---
pvr1-1, pepper   MATAEMEKTTTFDE------AEKVKL---NANEADDEVEEGEIVEETDD--TTSYLSK---
pvr1-2, pepper   MATAEMEKTTTFDE------AEKVKL---NANEADDEVEEGEIVEETDD--TTSYLSK---
pvr2-3, pepper   MATAEMEKTTTFDE------AEKVKL---NANEADDEVEEGEIVEETDD--TTSYLSK---
pvr2-4, pepper   MATAEMEKTTTFDE------AEKVKL---NANEADDEVEEGEIVEETDD--TTSYLSK---
pvr2-5, pepper   MATAEMEKTTTFDE------AEKVKL---NANEADDEVEEGEIVEETDD--TTSYLSK---
pvr2-6, pepper   MATAEMEKTTTFDE------AEKVKL---NANEADDEVEEGEIVEETDD--TTSYLSK---
pvr2-7, pepper   MATAEMEKTTTFDE------AEKVKL---NANEADDEVEEGEIVEETDD--TTSYLSK---
pvr2-8, pepper   MATAEMEKTTTFDE------AEKVKL---NANEADDEVEEGEIVEETDD--TTSYLSK---
pvr2-9, pepper   MATAEMEKTTTFDE------AEKVKL---NANEADDEVEEGEIVEETDD--TTSYLSK---
pot1, tomato     MAAAEMERTMSFDA------AEKLKAADGGGGEVDDELEEGEIVEESND--TASYLGK---
mo1, lettuce     MKSEEQ-KLIDVNK-------HEGVRSD-----GEEDEQLEEGEIVGGD----ADTLS---GG
mo2, lettuce     MESERQ-KLIDVNK-------HEGVRSD-----GEEDEQLEEGEIVGGD----ADTLS---SS
sbm1-1, pea      MVVEETPKSIITDD--------QITTNP-NRVIEDDNNLEEGEILDEDD--SSATSKP---
sbm1-2, pea      MVVEETPKSIITDD--------QITTNP-NRVIEDDNNLEEGEILDEDD--SSATSKP---
bc3, bean        -------KSTITDE--------Q---NP-SRVDNDDDDLEDGEILEDADDAAGAASKPPSA
MSV, melon       MVVEDSHKATSAEDLSRSIANQ---HPPGRGGEDEELEEGEIVGDDDLDSSNLS---AS
rym4, barley     MA-----EDTETRPA------SAGA--------------EEEKEGKIADXXDS--SAAAAAG---
rym5, barley     MA-----EDTETRPA------SAGA--------------EEREEEIADDGDQ--SAAAAAG---

pmp1, potato     EITVK-------HPLEHSWTFWFDNPTAKSRQIDWGS-SLRNVYTFSTVEDFWGAYNNIHH
pmp2, potato     EITVK-------HPLEHSWTFWFDSPIAKSRQTAWGS-SLRNVYTFSTVEDFWGAYNNIHH
pvr1, pepper     EIAAK-------HPLEHSWTFWFDNPVAKSKQAAWGS-SLRNVYTFSTVEDFWGAYNNIHH
pvr1-1, pepper   EIATK-------HPLEHSWTFWFDNPEAKSKQAAWGS-SRRNVYTFSTVEDFWGAYNNIHH
pvr1-2, pepper   EIATK-------HPLEHSWTFWFDNPEAKSKQAAWGS-SRRNVYTFSTVEDFWGAYNNIHH
pvr2-3, pepper   EIATK-------HPLEHSWTFWFDNPEAKSKQAAWGS-SLRNVYTFSTVEDFWGAYNNIHH
pvr2-4, pepper   EIATK-------HPLEHSWTFWFDNPVAKSKQAAWGS-SLRNVYTFSTVEDFWGAYNNIHH
pvr2-5, pepper   EIATK-------HPLEHSWTFWFDNTEAKSKQDAWGS-SLRNVYTFSTVEDFWGAYNNIHH
pvr2-6, pepper   EIATK-------HPLEHSWTFWFDNPVEKSKQDDWGS-SLRNVYTFSTVEDFWGAYNNIHH
pvr2-7, pepper   EIATK-------HPLEHSWTFWFDNPEAKSKQAAWGS-SRRNVYTFSTVEDFWGAYNNIHH
pvr2-8, pepper   EIATK-------HPLEHSWTFWFDNPVEKSKQAAWGS-SLRNVYTFSTVEDFWGAYNNIHH
pvr2-9, pepper   EIATK-------HPLEHSWTFWFDNPVEKSKQDAWGS-SLRNVYTFSTVEDFWGAYNNIHH
pot1, tomato     EITVK-------HPLEHSWTFWFDKSTTKSRQTTWGS-SLRNLYTFSTVEDFWGAYNNIHH
mo1, lettuce     SSSRPGTAIAQHPLEHSWTFWFDTPSPKSKQVAWGS-SMRPIYTFSSVEEFWSLYNNIHR
mo2, lettuce     GSSRPGTAIAQHPLEHSWTFWFDTPSAKSKQVAWGS-SMRPIYTFSSVEEFWSLYNNIHR
sbm1-1, pea      VVHQP-------HLLEHSWTFLFDTPAAKSKQDDWGSS-MRPIYTFSTVEEFWSIYNNIHH
sbm1-2, pea      VVHQP-------HLLEHSWTFWFDTPAAKSKQEDWGS--MRPIYTFSTVEEFWSIYNNIHH
bc3, bean        FLKKP-------HPLEHSWTFWYDNPSAKSKQAEWGS-SIRPIYTFSTVEEFWSIYNNIHH
msv, melon       LVHQP-------HPLEHSWTFWFDNPSAKSKQATWGA-SIRPIYTFSTVEEFWSVYNNIHH
rym4, barley     FVSA--------HPLENAWTFWFDNTQGKFRAVAWGS-TIHPIHTFSTVEDFWSLYNNIHH
rym5, barley     FVSA--------HPLENAWTFWFDNPQGKSRAVAWGS-TIHPIHTFSTVEDFWSLYNNIHH

pmp1, potato     PSKLVM--GADFHCFKHKIEPKWEDPICSNGGTWKMSFSKGKSDTSWLYTLLAMIGHQFD
pmp2, potato     PSKLNM--GADFHCFKHKIEPKWEDPVCANGGTWKMSFSKGKSDTSWLYTLLAMIGHQFD
pvr1, pepper     PSKLAV--GADLHCFKHKIEPKWEDPVCANGGTWKMSFSKGKSDTSWLYTLLAMIGHQFD
pvr1-1, pepper   PSKLVV--GADLHCFKHKIEPKWEDPVCANGGTWKMSFSKGKSDTSWLYTLLAMIGHQFD
pvr1-2, pepper   PSKLVV--GADLHCFKHKIEPKWEDPVCANGGTWKMSFSKGKSDTSWLYTLLAMIGHQFD
pvr2-3, pepper   PSKLAV--GADLHCFKHKIEPKWEDPVCANGGTWKMSFSKGKSDTSWLYTLLAMIGHQFD
pvr2-4, pepper   PSKLVV--GADLHCFKHKIEPKWEDPVCANGGTWKMSFSKGKSDTSWLYTLLAMIGHQFD
pvr2-5, pepper   PSKLVV--GADLHCFKHKIEPKWEDPVCANGGTWKMSFSKGKSDTSWLYTLLAMIGHQFD
pvr2-6, pepper   PSKLVV--GADLHCFKHKIEPKWEDPVCANGGTWKMSFSKGKSDTSWLYTLLAMIGHQFD
pvr2-7, pepper   PSKLVV--GADLHCFKHKIEPKWEDPVCANGGTWKMSFSKGKSDTSWLYTLLAMIGHQFD
pvr2-8, pepper   PSKLAV--RADLHCFKHKIEPKWEDPVCANGGTWKMSFSKGKSDTSWLYTLLAMIGHQFD
pvr2-9, pepper   PSKLVV--GADLHCFKHKIEPKWEDPVCANGGTWKMSFSKGKSDTSWLYTLLAMIGHQFD
pot1, tomato     PSKLII--GADFHCFKHKIEPQWEDPVCANGGTWKMSFSKGKSDTSWLYTLLAMIGHQFD
mo1, lettuce     PSKLAQGA--DFYCFKNKIEPKWEDPVCANGGKWTMTFTKAKSDTCWLYTLLAMIGEQFD
mo2, lettuce     PSKLAN----DFYCFKNKIEPKWEDPVCANGGKWTMTFTKAKSDTCWLYTLLAMIGEQFD
sbm1-1, pea      PGKLAV--RADFYCFKHKIEPKWEDPICANGGKWTANYPKGKSDTSWLYTLLAMIGEQFD
sbm1-2, pea      PGKLAV--GADFYCFKHKIEPKWEDPICANGGKWTANYPKGKSDTSWLYTLLAMIGEQFD
bc3, bean        PSKLAV--GAGFHCFKHKIEPKWEDPICANGGKWTMTFQRGKSDTSWLYTLLAMIGEQFD
msv, melon       PSKLAM--KADLYCFKHKIEPKWEDPVCANGGKWTVNFPRGKSDNGWLYTLLAMIGEQFD
rym4, barley     PSKLNV--GADFHCFKDKIEPKWEDPICANGGKWTISCGKGKSDTFWLHTLLALIGEQFD
rym5, barley     PSKLNV--GADFHCFKDKIEPKWEDPICANGGKWTISCGRGKSDTFWLHTLLALIGEQFD

pmp1, potato     HGDEICGAVVNVRVRGEKIALWTKNAANETAQVSIGKQWKQFLDYSDSVGFIFHDDAKKL
pmp2, potato     HGDEICGAVVSVRAKGEKIALWTKNAANETAQVSIGKQWKQFLDYSDSVGFIFHDDAKRL
pvr1, pepper     HEDEICGAVVSVRGRGEKISLWTKNAANETAQVSIGKQWKQFLDYSDSVGFIFHDDAKRL
pvr1-1, pepper   HEDEICGAVVSVRSRGEKISLWTKNAANETAQVSIGKQWKQFLDYSDSVGFIFHDDAKRL
```

FIG. 3 (continued)

```
pvr1-2, pepper       HKDKICGAVVSVRGKGEKISLWTKNAANETAQVSIGKQWKQFLDYSDSVGFIFHDDAKRL
pvr2-3, pepper       HKDEICGAVVSVRGKGEKISLWTKNAANETAQVSIGKQWKQFLDYSGSVGFIFHDDAKRL
pvr2-4, pepper       HKDKICGAVVSVRGKGEKISLWTKNAANETAQVSIGKQWKQFLDYSDSVGFIFHDDAKRL
pvr2-5, pepper       HEDEICGAVVSVRGKGEKISLWTKNAANETAQVSIGKQWKQFLDYSDSVGFIFHDDAKRL
pvr2-6, pepper       HKDEICGAVVSVRGKGEKISLWTKNAANETAQVSIGKQWKQFLDYSGSVGFIFHDDAKRL
pvr2-7, pepper       HEDEICGAVVSVRGKGEKISLWTKNAANETAQVSIGKQWKQFLDYSGSVGFIFHDDAKRL
pvr2-8, pepper       HEDEICGAVVSVRGKGEKISLWTKNAANETAQVSIGKQWKQFLDYSDSVGFIFHDDAKRL
pvr2-9, pepper       HEDEICGAVVSVRGKGEKISLWTKNAANETAQVSIGKQWKQFLDYSGSVGFIFHDDAKRL
pot1, tomato         HGDEICGAVVSVRANGEKIALWTKNAANETAQVSIGKQWKQFLDYSDSVGFIFHDDAKRL
mo1, lettuce         HGDDICGAVVNVRARQEKIALWTKNAANKSAQLSIGKQWKEFIDYNDTIGFIFHEDAKTL
mo2, lettuce         HGDDICGAVVNVRARQEKIALWTKNSANESAQLSIGKQWKEFIDYNDTIGFIFHEDAKTL
sbm1-1, pea          HGDEICGAVVEVRGRAEKISIWTKNASNEAAQVSIGKQWKEFLDYNETMGFIFHDDAKKL
sbm1-2, pea          HGDEICGAVVNVRGRAEKISIWTKNASNEAAQVSIGKQWKEFLDYNETMGFIFHDDAKKL
bc3, bean            YGDEICGAVVNVRNRQDKISIWTKNASNEAAQMSIGKQWKEFLDYNEPIGFIFHEDAKKH
nsv, melon           CGDEICGAVVNVRSGQDKISIWTKNASNEAAQASIGKQWKEFLDYNESIGFIFHDDAKKF
rym4, barley         FGDEICGAVVSVRKNQERVAIWTKNAANETAQISIGKQWKEFLDYKDSIGFVVHEDAKRS
rym5, barley         FGDEICGAVVSVRKNKERVAIWTKNAANETAQISIGKQWKEFLDYKDSIGFVVHEDAKRS

pwp1, potato         DRNAKNRYTV
pwp2, potato         DRNAKNRYTV
pvr1, pepper         DRNAKNRYTV
pvr1-1, pepper       DRNAKNRYTV
pvr1-2, pepper       DRNAKNRYTV
pvr2-3, pepper       DRNAKNRYTV
pvr2-4, pepper       DRNAKDRYTV
pvr2-5, pepper       NRNAKNRYTV
pvr2-6, pepper       DRNAKNRYTV
pvr2-7, pepper       DRNAKNRYTV
pvr2-8, pepper       DRNAKNRYTV
pvr2-9, pepper       DRNAKNRYTV
pot1, tomato         DRSAKNRYTV
mo1, lettuce         DRSAKNKYTV
mo2, lettuce         DRSAKNKYTV
sbm1-1, pea          DRNAKNKYVV
sbm1-2, pea          DRNAKNKYVV
bc3, bean            ER--------
nsv, melon           DRLAKNKYMV
rym4, barley         DKGAKNKYTV
rym5, barley         DKDAKDRYTV
```

FIGURE 9
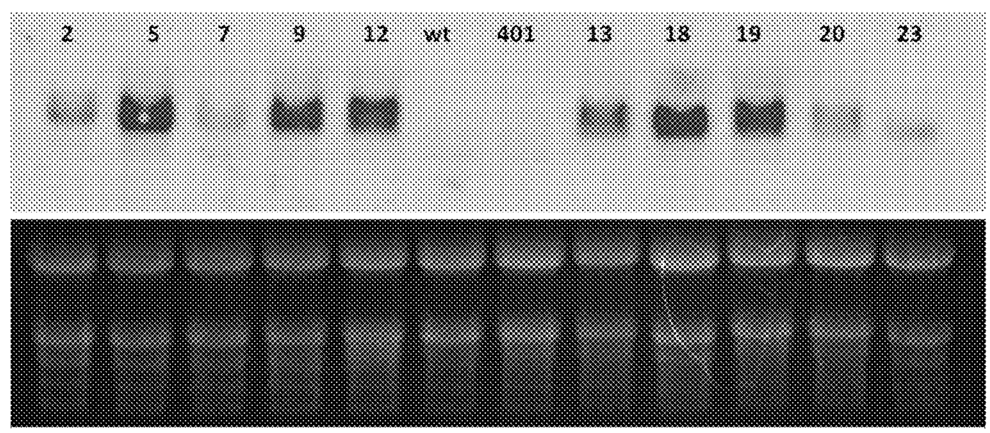
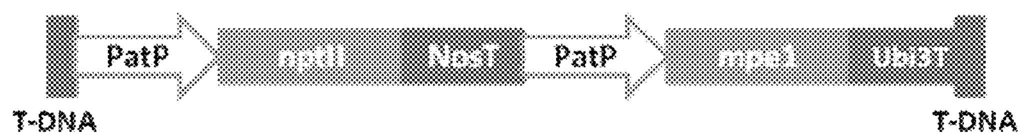
pSIM1588

FIGURE 10
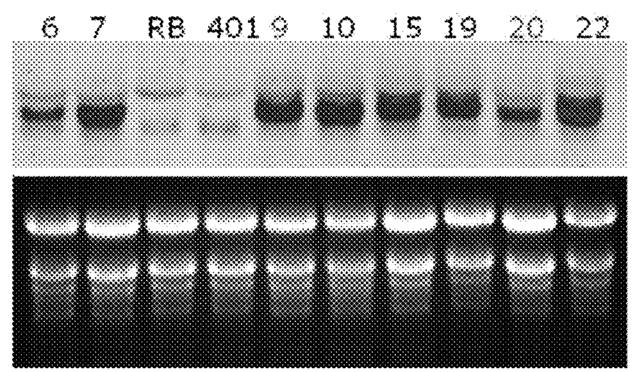
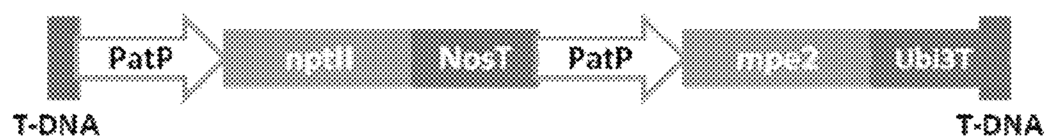
pSIM1723

SEQUENCE LISTING

<160> NUMBER OF SEQ ID NOS: 84

<210> SEQ ID NO 1
<211> LENGTH: 696
<212> TYPE: DNA
<213> ORGANISM: Unknown
<220> FEATURE:
<223> OTHER INFORMATION: Description of Unknown: pwp1 full length polynucleotide sequence

<400> SEQUENCE: 1
atggcagcag ctgaaatgga gagaacgacg tcgtttgatg cagctgagaa gttgaaggcc 60
gccgatgcag gaggaggaga ggtagacgat gaacttgaag aaggtgaaat tgttgaagaa 120
tcaaatgatg cggcgtcgta tttggggaaa gaaatcacag tgaagcatcc attggagcat 180
tcatggactt tttggtttga taaccctact gctagatctc gacaaattga ttggggaagc 240
tcacttcgaa atgtctacac tttctccact gttgaagatt tttggggtgc ttacaataat 300
atccatcacc caagcaagtt ggttatggga gcagactttc attgttttaa gcataaaatt 360
gagccaaagt gggaagatcc tatatgttcc aatggaggga cgtggaaaat gagtttttcg 420
aagggtaaat ctgataccag ctggctatat acgctgctgg caatgattgg acatcaattc 480
gatcatggag atgaaatttg tggagcagtc gttaatgtcc gggttaaggg agaaaaaata 540
gctttgtgga ccaagaatgc tgcaaatgaa acagctcagg ttagcattgg taagcaatgg 600
aagcagtttc tagattacag cgattcggtt ggcttcatat ttcatgacga tgcaaagagg 660
ctcgacagaa atgccaagaa tcgttacaca gtatag 696

<210> SEQ ID NO 2
<211> LENGTH: 231
<212> TYPE: PRT
<213> ORGANISM: Unknown
<220> FEATURE:
<223> OTHER INFORMATION: Description of Unknown: pwp1 full length amino acid sequence

<400> SEQUENCE: 2

Met Ala Ala Ala Glu Met Glu Arg Thr Thr Ser Phe Asp Ala Ala Glu
1 5 10 15

Lys Leu Lys Ala Ala Asp Ala Gly Gly Gly Glu Val Asp Asp Glu Leu
20 25 30

Glu Glu Gly Glu Ile Val Glu Glu Ser Asn Asp Ala Ala Ser Tyr Leu
35 40 45

Gly Lys Glu Ile Thr Val Lys His Pro Leu Glu His Ser Trp Thr Phe
50 55 60

Trp Phe Asp Asn Pro Thr Ala Arg Ser Arg Gln Ile Asp Trp Gly Ser
65 70 75 80

Ser Leu Arg Asn Val Tyr Thr Phe Ser Thr Val Glu Asp Phe Trp Gly
85 90 95

Ala Tyr Asn Asn Ile His His Pro Ser Lys Leu Val Met Gly Ala Asp
100 105 110

```
Phe His Cys Phe Lys His Lys Ile Glu Pro Lys Trp Glu Asp Pro Ile
        115                 120                 125

Cys Ser Asn Gly Gly Thr Trp Lys Met Ser Phe Ser Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Asn Val Arg Val Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Asn
    210                 215                 220

Ala Lys Asn Arg Tyr Thr Val
225                 230


<210> SEQ ID NO 3
<211> LENGTH: 695
<212> TYPE: DNA
<213> ORGANISM: Unknown
<220> FEATURE:
<223> OTHER INFORMATION: Description of Unknown: pwp2 full length
      polynucleotide sequence

<400> SEQUENCE: 3

atggcagcag ctgaaatgga gagaacgatg tcgtttgatg cagctgagaa gctgaaggcc      60

gccgatggag gaggaggga ggtagacgat gaacttgaag aaggtgaaat tgttgaagaa      120

tcaaatgata cggcgtcgtt tttagggaaa gaaatcacag tgaagcatcc attggagcat     180

tcatggactt tttggtttga tagccctatt gctaaatctc gacaaactgc ttggggaagc     240

tcacttcgaa atgtctacac tttctccact gttgaagatt tttggggtgc ttactataat     300

atccatcacc caagcaagtt ggttatggga gcagactttc attgttttaa gcataaaatt     360

gagccaaagt gggaagatcc tgtatgtgcc aatggaggga cgtggaaaat gagttttccg     420

aagggtaaat ctgataccag ctggctatat acgctgctgg caatgattgg acatcaattc     480

gatcatggag atgaaatttg tggagcagtc gttagtgtcc gggctaaggg agaaaaaata     540

gctttgtgga ccaagaatgc tgcaaacgaa acagctcagg ttagcattgg caaacaatgg     600

aagcagtttc tagattacag cgattcggtt ggcttcatat ttcacgatga tgcaaagagg     660

ctcgacagaa atgccaagaa tcgttacaca gttag                                695


<210> SEQ ID NO 4
<211> LENGTH: 231
<212> TYPE: PRT
<213> ORGANISM: Unknown
<220> FEATURE:
<223> OTHER INFORMATION: Description of Unknown: pwp2 full length
      amino acid sequence

<400> SEQUENCE: 4

Met Ala Ala Ala Glu Met Glu Arg Thr Met Ser Phe Asp Ala Ala Glu
1               5                   10                  15

Lys Leu Lys Ala Ala Asp Gly Gly Gly Gly Glu Val Asp Asp Glu Leu
            20                  25                  30

Glu Glu Gly Glu Ile Val Glu Glu Ser Asn Asp Thr Ala Ser Phe Leu
        35                  40                  45
```

```
Gly Lys Glu Ile Thr Val Lys His Pro Leu Glu His Ser Trp Thr Phe
    50                  55                  60

Trp Phe Asp Ser Pro Ile Ala Lys Ser Arg Gln Thr Ala Trp Gly Ser
65                  70                  75                  80

Ser Leu Arg Asn Val Tyr Thr Phe Ser Thr Val Glu Asp Phe Trp Gly
                85                  90                  95

Ala Tyr Tyr Asn Ile His His Pro Ser Lys Leu Val Met Gly Ala Asp
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Ser Phe Pro Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Ser Val Arg Ala Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Asn
    210                 215                 220

Ala Lys Asn Arg Tyr Thr Val
225                 230


<210> SEQ ID NO 5
<211> LENGTH: 696
<212> TYPE: DNA
<213> ORGANISM: Solanum sp.

<400> SEQUENCE: 5

atggcagcag ctgaaatgga gagaacgacg tcgtttgatg cagctgagaa gttgaaggcc      60

gccgatgcag gaggaggaga ggtagacgat gaacttgaag aaggtgaaat tgttgaagaa     120

tcaaatgata cggcgtcgta tttagggaaa gaaatcacag tgaaacatcc attggagcat     180

tcatggactt tttggtttga tagccctatt gctaaatctc gacaaactgc ttggggaagc     240

tcacttcgaa atgtctacac tttctccact gttgaagatt tttggggtgc ttacaataat     300

atccatcacc caagcaagtt ggttatggga gcagactttc attgttttaa gcataaaatt     360

gagccaaagt gggaagatcc tgtatgtgcc aatggaggga cgtggaaaat gaatttttttg     420

aagggtaaat ctgataccag ctggctatat acgctgctgg caatgattgg acatcaattc     480

gatcacggag atgaaatttg tggagcagtc gttagtgtcc ggtctaaggg agaaaaaata     540

gctttgtgga ccaagaatgc tgcaaatgaa acagctcagg ttagcattgg taagcaatgg     600

aagcagtttc tagattacag cgattcggtt ggcttcatat ttcacgatga tgcaaagagg     660

ctcgacagaa gtgccaagaa tcgttacaca gtatag                               696


<210> SEQ ID NO 6
<211> LENGTH: 231
<212> TYPE: PRT
<213> ORGANISM: Solanum sp.

<400> SEQUENCE: 6

Met Ala Ala Ala Glu Met Glu Arg Thr Thr Ser Phe Asp Ala Ala Glu
1               5                   10                  15
```

```
Lys Leu Lys Ala Ala Asp Ala Gly Gly Gly Glu Val Asp Asp Glu Leu
            20                  25                  30

Glu Glu Gly Glu Ile Val Glu Glu Ser Asn Asp Thr Ala Ser Tyr Leu
        35                  40                  45

Gly Lys Glu Ile Thr Val Lys His Pro Leu Glu His Ser Trp Thr Phe
    50                  55                  60

Trp Phe Asp Ser Pro Ile Ala Lys Ser Arg Gln Thr Ala Trp Gly Ser
65                  70                  75                  80

Ser Leu Arg Asn Val Tyr Thr Phe Ser Thr Val Glu Asp Phe Trp Gly
                85                  90                  95

Ala Tyr Asn Asn Ile His His Pro Ser Lys Leu Val Met Gly Ala Asp
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Asn Phe Leu Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Ser Val Arg Ser Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp His Ser Asp
        195                 200                 205

Ser Val Gly Phe Ile Phe His Asp Asp Ala Lys Arg Leu Asp Arg Ser
    210                 215                 220

Ala Lys Asn Arg Tyr Thr Val
225                 230


<210> SEQ ID NO 7
<211> LENGTH: 780
<212> TYPE: DNA
<213> ORGANISM: Cauliflower mosaic virus

<400> SEQUENCE: 7

atggtggagc acgacactct cgtctactcc aagaatatca aagatacagt ctcagaagac      60

caaagggcta ttgagacttt tcaacaaagg gtaatatcgg gaaacctcct cggattccat     120

tgcccagcta tctgtcactt catcaaaagg acagtagaaa aggaaggtgg cacctacaaa     180

tgccatcatt gcgataaagg aaaggctatc gttcaagatg cctctgccga cagtggtccc     240

aaagatggac ccccacccac gaggagcatc gtggaaaaag aagacgttcc aaccacgtct     300

tcaaagcaag tggattgatg tgaacatggt ggagcacgac actctcgtct actccaagaa     360

tatcaaagat acagtctcag aagaccaaag ggctattgag acttttcaac aaagggtaat     420

atcgggaaac ctcctcggat tccattgccc agctatctgt cacttcatca aaaggacagt     480

agaaaaggaa ggtggcacct acaaatgcca tcattgcgat aaaggaaagg ctatcgttca     540

agatgcctct gccgacagtg gtcccaaaga tggaccccca cccacgagga gcatcgtgga     600

aaaagaagac gttccaacca cgtcttcaaa gcaagtggat tgatgtgata tctccactga     660

cgtaagggat gacgcacaat cccactatcc ttcgcaagac ccttcctcta tataaggaag     720

ttcatttcat ttggagagga cacgctgaaa tcaccagtct ctctctacaa atctatctct     780


<210> SEQ ID NO 8
<211> LENGTH: 1150
```

```
<212> TYPE: DNA
<213> ORGANISM: Solanum sp.

<400> SEQUENCE: 8

gccaaagcac atacttatcg atttaaattt catcgaagag attaatatcg aataatcata     60

tacatacttt aaatacataa caaattttaa atacatatat ctggtatata attaattttt    120

taaagtcatg aagtatgtat caaatacaca tatggaaaaa attaactatt cataatttaa    180

aaaatagaaa agatacatct agtgaaatta ggtgcatgta tcaaatacat taggaaaagg    240

gcatatatct tgatctagat aattaacgat tttgatttat gtataatttc caaatgaagg    300

tttatatcta cttcagaaat aacaatatac ttttatcaga acattcaaca aagtaacaac    360

caactagagt gaaaaataca cattgttctc taaacataca aaattgagaa aagaatctca    420

aaatttagag aaacaaatct gaatttctag aagaaaaaaa taattatgca ctttgctatt    480

gctcgaaaaa taaatgaaag aaattagact tttttaaaag atgttagact agatatactc    540

aaaagctatc aaaggagtaa tattcttctt acattaagta ttttagttac agtcctgtaa    600

ttaaagacac attttagatt gtatctaaac ttaaatgtat ctagaataca tatatttgaa    660

tgcatcatat acatgtatcc gacacaccaa ttctcataaa aagcgtaata tcctaaacta    720

atttatcctt caagtcaact taagcccaat atacattttc atctctaaag gcccaagtgg    780

cacaaaatgt caggcccaat tacgaagaaa agggcttgta aaaccctaat aaagtggcac    840

tggcagagct tacactctca ttccatcaac aaagaaaccc taaaagccgc agcgccactg    900

atttctctcc tccaggcgaa gatgcagatc ttcgtgaaga ccctaacggg gaagacgatc    960

accctagagg ttgagtcttc cgacaccatc gacaatgtca aagccaagat ccaggacaag   1020

gaagggattc ccccagacca gcagcgtttg attttcgccg gaaagcagct tgaggatggt   1080

cgtactcttg ccgactacaa catccagaag gagtcaactc tccatctcgt gctccgtctc   1140

cgtggtggtg                                                          1150


<210> SEQ ID NO 9
<211> LENGTH: 1738
<212> TYPE: DNA
<213> ORGANISM: Solanum sp.

<400> SEQUENCE: 9

cacattgatt gagttttata tgcaatatag taataataat aatatttctt ataaagcaag     60

aggtcaattt ttttttatta taccaacgtc actaaattat atttgataat gtaaaacaat    120

tcaattttac ttaaatatca tgaaataaac tatttttata accaaattac taaatttttc    180

caataaaaaa aagtcattaa gaagacataa aataaatttg agtaaaaaga gtgaagtcga    240

ctgacttttt tttttttatc ataagaaaat aaattattaa ctttaaccta ataaaacact    300

aatataattt catggaatct aatacttacc tcttagaaat aagaaaaagt gtttctaata    360

gaccctcaat ttacattaaa tattttcaat caaatttaaa taacaaatat caatatgagg    420

tcaataacaa tatcaaaata atatgaaaaa agagcaatac ataatataag aaagaagatt    480

taagtgcgat tatcaaggta gtattatatc ctaatttgct aatatttaaa ctcttatatt    540

taaggtcatg ttcatgataa acttgaaatg cgctatatta gagcatatat taaaataaaa    600

aaatacctaa aataaaatta agttattttt agtatatatt tttttacatg acctacattt    660

ttctgggttt ttctaaagga gcgtgtaagt gtcgacctca ttctcctaat tttccccacc    720

acataaaaat taaaaaggaa aggtagcttt tgcgtgttgt tttggtacac tacacctcat    780
```

```
tattacacgt gtcctcatat aattggttaa ccctatgagg cggtttcgtc tagagtcggc    840

catgccatct ataaaatgaa gctttctgca cctcattttt ttcatcttct atctgatttc    900

tattataatt tctctcaatt gccttcaaat ttctctttaa ggttagaaat cttctctatt    960

tttggttttt gtctgtttag attctcgaat tagctaatca ggtgctgtta tagcccttaa   1020

ttttgagttt tttttcggtt gttttgatgg aaaaggccta aaatttgagt ttttttacgt   1080

tggtttgatg gaaaaggcct acaattggag ttttccccgt tgttttgatg aaaaagcccc   1140

tagtttgaga ttttttttct gtcgattcga ttctaaaggt ttaaaattag agtttttaca   1200

tttgtttgat gaaaaaggcc ttaaatttga gtttttccgg ttgatttgat gaaaaagccc   1260

tagaatttgt gtttttttcgt cggtttgatt ctgaaggcct aaaatttgag tttctccggc   1320

tgttttgatg aaaaagccct aaatttgagt ttctccggct gttttgatga aaaagcccta   1380

aatttgagtt ttttccccgt gttttagatt gtttggtttt aattctcgaa tcagctaatc   1440

agggagtgtg aaaagcccta aaatttgagt ttttttcgtt gttctgattg ttgtttttat   1500

gaatttgcag atgcagatct ttgtgaaaac tctcaccgga aagactatca ccctagaggt   1560

ggaaagttct gatacaatcg acaacgttaa ggctaagatc caggataagg aaggaattcc   1620

cccggatcag caaaggctta tcttcgccgg aaagcagttg gaggacggac gtactctagc   1680

tgattacaac atccagaagg agtctaccct ccatttggtg ctccgtctac gtggaggt     1738
```

```
<210> SEQ ID NO 10
<211> LENGTH: 286
<212> TYPE: DNA
<213> ORGANISM: Solanum sp.

<400> SEQUENCE: 10

cacctccatc aacaatattc aaagagaatt gtactacaga ggaataatag ggagcctggg     60

gaagtaatgc agaacacgcg aattgtagag gcatggattc aaaccaaaca attttccgcg    120

attagaaagt gcaaacacca atacacgagt tactcaaacc agaagcttat caaatgagaa    180

acaaaaccag tgcctaccaa ctttccagta cgaattgtgt ttcttgcatt cccacattgc    240

atcaagaact aatttgctgc tctgtggact gtggagcact tttttt                  286
```

```
<210> SEQ ID NO 11
<211> LENGTH: 6564
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

tcgagcacat tgattgagtt ttatatgcaa tatagtaata ataataatat ttcttataaa     60

gcaagaggtc aatttttttt taattatacc aacgtcacta aattatattt gataatgtaa    120

aacaattcaa ttttacttaa atatcatgaa ataaactatt tttataacca aattactaaa    180

tttttccaat aaaaaaaagt cattaagaag acataaaata aatttgagta aaaagagtga    240

agtcgactga cttttttttt ttttatcata agaaaataaa ttattaactt taacctaata    300

aaacactaat ataatttcat ggaatctaat acttacctct tagaaataag aaaaagtgtt    360

tctaatagac cctcaattta cattaaatat tttcaatcaa atttaaataa caaatatcaa    420

tatgaggtca ataacaatat caaaataata tgaaaaaaga gcaatacata atataagaaa    480

gaagatttaa gtgcgattat caaggtagta ttatatccta atttgctaat atttaaactc    540
```

-continued

```
ttatatttaa ggtcatgttc atgataaact tgaaatgcgc tatattagag catatattaa    600
aataaaaaaa tacctaaaat aaaattaagt tatttttagt atatattttt ttacatgacc    660
tacatttttc tgggtttttc taaaggagcg tgtaagtgtc gacctcattc tcctaatttt    720
ccccaccaca taaaaattaa aaaggaaagg tagcttttgc gtgttgtttt ggtacactac    780
acctcattat tacacgtgtc ctcatataat tggttaaccc tatgaggcgg tttcgtctag    840
agtcggccat gccatctata aaatgaagct ttctgcacct catttttttc atcttctatc    900
tgatttctat tataatttct ctcaattgcc ttcaaatttc tctttaaggt tagaaatctt    960
ctctattttt ggtttttgtc tgtttagatt ctcgaattag ctaatcaggt gctgttatag   1020
cccttaattt tgagtttttt ttcggttgtc ttgatggaaa aggcctaaaa tttgagtttt   1080
tttacgttgg tttgatggaa aaggcctaca attggagttt tccccgttgt tttgatgaaa   1140
aagcccctag tttgagattt tttttctgtc gattcgattc taaaggttta aaattagagt   1200
ttttacattt gtttgatgaa aaaggcctta aatttgagtt tttccggttg atttgatgaa   1260
aaagccctag aatttgtgtt ttttcgtcgg tttgattctg aaggcctaaa atttgagttt   1320
ctccggctgt tttgatgaaa aagccctaaa tttgagtttc tccggctgtt ttgatgaaaa   1380
agccctaaat ttgagttttt tccccgtgtt ttagattgtt tggttttaat tctcgaatca   1440
gctaatcagg gagtgtgaaa agccctaaat ttgagttttt ttcgttgttc tgattgttgt   1500
ttttatgaat ttgcagatgc agatctttgt gaaaactctc accggaaaga ctatcaccct   1560
agaggtggaa agttctgata caatcgacaa cgttaaggct aagatccagg ataaggaagg   1620
aattcccccg gatcagcaaa ggcttatctt cgccggaaag cagttggagg acggacgtac   1680
tctagctgat tacaacatcc agaaggagtc taccctccat ttggtgctcc gtctacgtgg   1740
aggtggatcc atggcagcag ctgaaatgga gagaacgacg tcgtttgatg cagctgagaa   1800
gttgaaggcc gccgatgcag gaggaggaga ggtagacgat gaacttgaag aaggtgaaat   1860
tgttgaagaa tcaaatgatg cggcgtcgta tttggggaaa gaaatcacag tgaagcatcc   1920
attggagcat tcatggactt tttggtttga taaccctact gctagatctc gacaaattga   1980
ttggggaagc tcacttcgaa atgtctacac tttctccact gttgaagatt tttggggtgc   2040
ttacaataat atccatcacc caagcaagtt ggttatggga gcagactttc attgttttaa   2100
gcataaaatt gagccaaagt gggaagatcc tatatgttcc aatggaggga cgtggaaaat   2160
gagtttttcg aagggtaaat ctgataccag ctggctatat acgctgctgg caatgattgg   2220
acatcaattc gatcatggag atgaaatttg tggagcagtc gttaatgtcc gggttaaggg   2280
agaaaaaata gctttgtgga ccaagaatgc tgcaaatgaa acagctcagg ttagcattgg   2340
taagcaatgg aagcagtttc tagattacag cgattcggtt ggcttcatat ttcatgacga   2400
tgcaaagagg ctcgacagaa atgccaagaa tcgttacaca gtatagacta gtttttaatg   2460
tttagcaaat gtcctatcag ttttctcttt ttgtcgaacg gtaatttaga gttttttttg   2520
ctatatggat tttcgttttt gatgtatgtg acaaccctcg ggattgttga tttatttcaa   2580
aactaagagt ttttgcttat tgttctcgtc tattttggat atcaatctta gttttatatc   2640
ttttctagtt ctctacgtgt taaatgttca acacactagc aatttggctg cagcgtatgg   2700
attatggaac tatcaagtct gtgggatcga taaatatgct tctcaggaat ttgagatttt   2760
acagtcttta tgctcattgg gttgagtata atatagtaaa aaaataggta tcgataccgt   2820
cgacctcgat cgaggggggg ccccacattg attgagtttt atatgcaata tagtaataat   2880
aataatattt cttataaagc aagaggtcaa ttttttttta ttataccaac gtcactaaat   2940
```

```
tatatttgat aatgtaaaac aattcaattt tacttaaata tcatgaaata aactattttt   3000
ataaccaaat tactaaattt ttccaataaa aaaaagtcat taagaagaca taaaataaat   3060
ttgagtaaaa agagtgaagt cgactgactt tttttttttt atcataagaa aataaattat   3120
taactttaac ctaataaaac actaatataa tttcatggaa tctaatactt acctcttaga   3180
aataagaaaa agtgtttcta atagaccctc aatttacatt aaatattttc aatcaaattt   3240
aaataacaaa tatcaatatg aggtcaataa caatatcaaa ataatatgaa aaaagagcaa   3300
tacataatat aagaaagaag atttaagtgc gattatcaag gtagtattat atcctaattt   3360
gctaatattt aaactcttat atttaaggtc atgttcatga taaacttgaa atgcgctata   3420
ttagagcata tattaaaata aaaaaatacc taaaataaaa ttaagttatt tttagtatat   3480
atttttttac atgacctaca tttttctggg tttttctaaa ggagcgtgta agtgtcgacc   3540
tcattctcct aattttcccc accacataaa aattaaaaag gaaaggtagc ttttgcgtgt   3600
tgttttggta cactacacct cattattaca cgtgtcctca tataattggt taaccctatg   3660
aggcggtttc gtctagagtc ggccatgcca tctataaaat gaagctttct gcacctcatt   3720
tttttcatct tctatctgat ttctattata atttctctca attgccttca aatttctctt   3780
taaggttaga aatcttctct atttttggtt tttgtctgtt tagattctcg aattagctaa   3840
tcaggtgctg ttatagccct taattttgag tttttttttcg gttgttttga tggaaaaggc   3900
ctaaaatttg agtttttttta cgttggtttg atggaaaagg cctacaattg gagttttccc   3960
cgttgttttg atgaaaaagc ccctagtttg agattttttt tctgtcgatt cgattctaaa   4020
ggtttaaaat tagagttttt acatttgttt gatgaaaaag gccttaaatt tgagtttttc   4080
cggttgattt gatgaaaaag ccctagaatt tgtgtttttt cgtcggtttg attctgaagg   4140
cctaaaattt gagtttctcc ggctgttttg atgaaaaagc cctaaatttg agtttctccg   4200
gctgttttga tgaaaaagcc ctaaatttga gtttttttccc cgtgttttag attgtttggt   4260
tttaattctc gaatcagcta atcagggagt gtgaaaagcc ctaaaatttg agtttttttc   4320
gttgttctga ttgttgtttt tatgaatttg cagatgcaga tctttgtgaa aactctcacc   4380
ggaaagacta tcaccctaga ggtggaaagt tctgatacaa tcgacaacgt taaggctaag   4440
atccaggata aggaaggaat tcccccggat cagcaaaggc ttatcttcgc cggaaagcag   4500
ttggaggacg gacgtactct agctgattac aacatccaga aggagtctac cctccatttg   4560
gtgctccgtc tacgtggagg tggatcccac ctccatcaac aatattcaaa gagaattgta   4620
ctacagagga ataatággga gcctggggaa gtaatgcaga acacgcgaat tgtagaggca   4680
tggattcaaa ccaaacaatt ttccgcgatt agaaagtgca aacaccaata cacgagttac   4740
tcaaaccaga agcttatcaa atgagaaaca aaaccagtgc ctaccaactt tccagtacga   4800
attgtgtttc ttgcattccc acattgcatc aagaactaat ttgctgctct gtggactgtg   4860
gagcactttt tttgaattcg taacttttac tcatctcctc caattatttc tgatttcatg   4920
catgtttccc tacattctat tatgaatcgt gttatggtgt ataaacgttg tttcatatct   4980
catctcatct attctgattt tgattctctt gcctactgaa tttgacccta ctgtaatcgg   5040
tgataaatgt gaatgcttcc tcttcttctt cttcttctca gaaatcaatt tctgttttgt   5100
ttttgttcat ctgtagccgc ggaaaaaaag tgctccacag tccacagagc agcaaaatag   5160
ttcttgatgc aatgtgggaa tgcaagaaac acaattcgta ctggaaagtt ggtaggcact   5220
ggttttgttt ctcatttgat aagcttctgg tttgagtaac tcgtgtattg gtgtttgcac   5280
```

```
tttctaatcg cggaaaattg tttggtttga atccatgcct ctacaattcg cgtgttctgc   5340

attacttccc caggctccct attattcctc tgtagtacaa ttctctttga atattgttga   5400

tggaggtgac tagtcaccac cacggagacg gagcacgaga tggagagttg actccttctg   5460

gatgttgtag tcggcaagag tacgaccatc ctcaagctgc tttccggcga aaatcaaacg   5520

ctgctggtct gggggaatcc cttccttgtc ctggatcttg gctttgacat tgtcgatggt   5580

gtcggaagac tcaacctcta gggtgatcgt cttccccgtt agggtcttca cgaagatctg   5640

catcttcgcc tggaggagag aaatcagtgg cgctgcggct tttagggttt ctttgttgat   5700

ggaatgagag tgtaagctct gccagtgcca ctttattagg gttttacaag ccctttttctt   5760

cgtaattggg cctgacattt tgtgccactt gggcctttag agatgaaaat gtatattggg   5820

cttaagttga cttgaaggat aaattagttt aggatattac gctttttatg agaattggtg   5880

tgtcggatac atgtatatga tgcattcaaa tatatgtatt ctagatacat ttaagtttag   5940

atacaatcta aaatgtgtct ttaattacag gactgtaact aaaatactta atgtaagaag   6000

aatattactc ctttgatagc ttttgagtat atctagtcta acatctttta aaaaagtcta   6060

atttctttca tttattttc gagcaatagc aaagtgcata attattttt tcttctagaa   6120

attcagattt gtttctctaa attttgagat tcttttctca attttgtatg tttagagaac   6180

aatgtgtatt tttcactcta gttggttgtt actttgttga atgttctgat aaaagtatat   6240

tgttatttct gaagtagata taaaccttca tttggaaatt atacataaat caaaatcgtt   6300

aattatctag atcaagatat atgccctttt cctaatgtat ttgatacatg cacctaattt   6360

cactagatgt atcttttcta tttttaaat tatgaatagt taattttttc catatgtgta   6420

tttgatacat acttcatgac tttaaaaaat taattatata ccagatatat gtatttaaaa   6480

tttgttatgt atttaaagta tgtatatgat tattcgatat taatctcttc gatgaaattt   6540

aaatcgataa gtatgtgctt tggc                                          6564
```

```
<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

gattggggat ccatggcaaa gcatccatta gagcat                                36


<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

atgctctaat ggatgctttg ccatggatcc ccaatc                                36


<210> SEQ ID NO 14
<211> LENGTH: 687
<212> TYPE: DNA
<213> ORGANISM: Capsicum sp.

<400> SEQUENCE: 14

atggcaacag ctgaaatgga gaaaacgacg acgtttgatg aagctgagaa ggtgaaattg      60
```

```
aatgctaatg aggcagatga tgaagttgaa gaaggtgaaa ttgttgaaga aactgatgat    120

acgacgtcgt atttgagcaa agaaatagca acaaagcatc cattagagca ttcatggact    180

ttctggtttg ataatccaga ggcgaaatcg aaacaagctg cttggggtag ctcgcgtcgc    240

aacgtctaca ctttctccac tgttgaagat tttggggtg cttacaataa tatccaccac     300

ccaagcaagt tagttgtggg agcagactta cattgtttca agcataaaat tgagccaaag    360

tgggaagatc ctgtatgtgc caatggaggg acatggaaaa tgagtttttc aaagggtaaa    420

tctgatacca gctggctata tacgctgctt gcaatgattg gacatcaatt cgatcatgaa    480

gatgaaattt gtggagcagt agttagtgtc agaggtaagg gagaaaaaat atctttgtgg    540

accaagaatg ctgcaaatga aacggctcag gttagcattg gtaagcaatg gaagcagttt    600

ctggattaca gcgacagtgt tggcttcata tttcacgacg atgcaaagag gctcgacaga    660

aatgcaaaga atcgttacac agtataa                                        687
```

```
<210> SEQ ID NO 15
<211> LENGTH: 540
<212> TYPE: DNA
<213> ORGANISM: Capsicum sp.

<400> SEQUENCE: 15

atggcaaagc atccattaga gcattcatgg actttctggt ttgataatcc agaggcgaaa     60

tcgaaacaag ctgcttgggg tagctcgcgt cgcaacgtct acactttctc cactgttgaa    120

gatttttggg gtgcttacaa taatatccac cacccaagca agttagttgt gggagcaaac    180

ttacattgtt tcaagcataa aattgagcca aagtgggaag atcctgtatg tgccaatgga    240

gggacatgga aaatgagttt ttcaaagggt aaatctgata ccagctggct atatacgctg    300

cttgcaatga ttggacatca attcgatcat gaagatgaaa tttgtggagc agtagttagt    360

gtcagaggta agggagaaaa aatatctttg tggaccaaga atgctgcaaa tgaaacggct    420

caggttagca ttggtaagca atggaagcag tttctggatt acagcgacag tgttggcttc    480

atatttcacg acgatgcaaa gaggctcgac agaaatgcaa agaatcgtta caccgtatag    540
```

```
<210> SEQ ID NO 16
<211> LENGTH: 180
<212> TYPE: PRT
<213> ORGANISM: Capsicum sp.

<400> SEQUENCE: 16

Met Ala Thr Lys His Pro Leu Glu His Ser Trp Thr Phe Trp Phe Asp
1               5                   10                  15

Asn Pro Glu Ala Lys Ser Lys Gln Ala Ala Trp Gly Ser Ser Arg Arg
            20                  25                  30

Asn Val Tyr Thr Phe Ser Thr Val Glu Asp Phe Trp Gly Ala Tyr Asn
        35                  40                  45

Asn Ile His His Pro Ser Lys Leu Val Val Gly Ala Asn Leu His Cys
    50                  55                  60

Phe Lys His Lys Ile Glu Pro Lys Trp Glu Asp Pro Val Cys Ala Asn
65                  70                  75                  80

Gly Gly Thr Trp Lys Met Ser Phe Ser Lys Gly Lys Ser Asp Thr Ser
                85                  90                  95

Trp Leu Tyr Thr Leu Leu Ala Met Ile Gly His Gln Phe Asp His Glu
            100                 105                 110

Asp Glu Ile Cys Gly Ala Val Val Ser Val Arg Gly Lys Gly Glu Lys
```

```
        115                 120                 125

Ile Ser Leu Trp Thr Lys Asn Ala Ala Asn Glu Thr Ala Gln Val Ser
    130                 135                 140

Ile Gly Lys Gln Trp Lys Gln Phe Leu Asp Tyr Ser Asp Ser Val Gly
145                 150                 155                 160

Phe Ile Phe His Asp Asp Ala Lys Arg Leu Asp Arg Asn Ala Lys Asn
                165                 170                 175

Arg Tyr Thr Val
            180


<210> SEQ ID NO 17
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Lys His Pro Leu Glu His Ser Trp Thr Phe Trp Phe Asp Ser
1               5                   10                  15

Pro Glu Ala Lys Ser Arg Gln Thr Ala Trp Gly Ser Ser Arg Arg Asn
            20                  25                  30

Val Tyr Thr Phe Ser Thr Val Glu Asp Phe Trp Gly Ala Tyr Asn Asn
        35                  40                  45

Ile His His Pro Ser Lys Leu Val Met Gly Ala Asn Phe His Cys Phe
    50                  55                  60

Lys His Lys Ile Glu Pro Lys Trp Glu Asp Pro Val Cys Ala Asn Gly
65                  70                  75                  80

Gly Thr Trp Lys Met Asn Phe Leu Lys Gly Lys Ser Asp Thr Ser Trp
                85                  90                  95

Leu Tyr Thr Leu Leu Ala Met Ile Gly His Gln Phe Asp His Gly Asp
            100                 105                 110

Glu Ile Cys Gly Ala Val Val Ser Val Arg Ser Lys Gly Glu Lys Ile
        115                 120                 125

Ala Leu Trp Thr Lys Asn Ala Ala Asn Glu Thr Ala Gln Val Ser Ile
    130                 135                 140

Gly Lys Gln Trp Lys Gln Phe Leu Asp Tyr Ser Asp Ser Val Gly Phe
145                 150                 155                 160

Ile Phe His Asp Asp Ala Lys Arg Leu Asp Arg Ser Ala Lys Asn Arg
                165                 170                 175

Tyr Thr Val


<210> SEQ ID NO 18
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

atggcaaaac atccattgga gcattcatgg actttttggt ttgatagccc tgaagctaaa      60

tctcgacaaa ctgcttgggg aagctcaaga cgaaatgtct acactttctc cactgttgaa     120

gatttttggg gtgcttacaa taatatccat cacccaagca agttggttat gggagcaaac     180

tttcattgtt ttaagcataa aattgagcca aagtgggaag atcctgtatg tgccaatgga     240
```

```
gggacgtgga aaatgaattt tttgaagggt aaatctgata ccagctggct atatacgctg    300

ctggcaatga ttggacatca attcgatcac ggagatgaaa tttgtggagc agtcgttagt    360

gtccggtcta agggagaaaa aatagctttg tggaccaaga atgctgcaaa tgaaacagct    420

caggttagca ttggtaagca atggaagcag tttctagatt acagcgattc ggttggcttc    480

atatttcacg atgatgcaaa gaggctcgac agaagtgcca agaatcgtta cacagtatag    540


<210> SEQ ID NO 19
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

atggcaaagc atccattgga gcattcatgg actttttggt ttgataaccc tactgctaga     60

tctcgacaaa ttgattgggg aagctcactt cgaaatgtct acactttctc cactgttgaa    120

gatttttggg gtgcttacaa taatatccat cacccaagca agttggttat gggagcagac    180

tttcattgtt ttaagcataa aattgagcca aagtgggaag atcctatatg ttccaatgga    240

gggacgtgga aaatgagttt ttcgaagggt aaatctgata ccagctggct atatacgctg    300

ctggcaatga ttggacatca attcgatcat ggagatgaaa tttgtggagc agtcgttaat    360

gtccgggtta agggagaaaa aatagctttg tggaccaaga atgctgcaaa tgaaacagct    420

caggttagca ttggtaagca atggaagcag tttctagatt acagcgattc ggttggcttc    480

atatttcatg acgatgcaaa gaggctcgac agaaatgcca agaatcgtta cacagtatag    540


<210> SEQ ID NO 20
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Lys His Pro Leu Glu His Ser Trp Thr Phe Trp Phe Asp Asn
1               5                   10                  15

Pro Thr Ala Arg Ser Arg Gln Ile Asp Trp Gly Ser Ser Leu Arg Asn
            20                  25                  30

Val Tyr Thr Phe Ser Thr Val Glu Asp Phe Trp Gly Ala Tyr Asn Asn
        35                  40                  45

Ile His His Pro Ser Lys Leu Val Met Gly Ala Asp Phe His Cys Phe
    50                  55                  60

Lys His Lys Ile Glu Pro Lys Trp Glu Asp Pro Ile Cys Ser Asn Gly
65                  70                  75                  80

Gly Thr Trp Lys Met Ser Phe Ser Lys Gly Lys Ser Asp Thr Ser Trp
                85                  90                  95

Leu Tyr Thr Leu Leu Ala Met Ile Gly His Gln Phe Asp His Gly Asp
            100                 105                 110

Glu Ile Cys Gly Ala Val Val Asn Val Arg Val Lys Gly Glu Lys Ile
        115                 120                 125

Ala Leu Trp Thr Lys Asn Ala Ala Asn Glu Thr Ala Gln Val Ser Ile
    130                 135                 140

Gly Lys Gln Trp Lys Gln Phe Leu Asp Tyr Ser Asp Ser Val Gly Phe
145                 150                 155                 160
```

```
Ile Phe His Asp Asp Ala Lys Arg Leu Asp Arg Asn Ala Lys Asn Arg
                165                 170                 175

Tyr Thr Val


<210> SEQ ID NO 21
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala Lys His Pro Leu Glu His Ser Trp Thr Phe Trp Phe Asp Ser
1               5                   10                  15

Pro Ile Ala Lys Ser Arg Gln Thr Ala Trp Gly Ser Ser Leu Arg Asn
            20                  25                  30

Val Tyr Thr Phe Ser Thr Val Glu Asp Phe Trp Gly Ala Tyr Tyr Asn
        35                  40                  45

Ile His His Pro Ser Lys Leu Val Met Gly Ala Asp Phe His Cys Phe
    50                  55                  60

Lys His Lys Ile Glu Pro Lys Trp Glu Asp Pro Val Cys Ala Asn Gly
65                  70                  75                  80

Gly Thr Trp Lys Met Ser Phe Pro Lys Gly Lys Ser Asp Thr Ser Trp
                85                  90                  95

Leu Tyr Thr Leu Leu Ala Met Ile Gly His Gln Phe Asp His Gly Asp
            100                 105                 110

Glu Ile Cys Gly Ala Val Val Ser Val Arg Ala Lys Gly Glu Lys Ile
        115                 120                 125

Ala Leu Trp Thr Lys Asn Ala Ala Asn Glu Thr Ala Gln Val Ser Ile
    130                 135                 140

Gly Lys Gln Trp Lys Gln Phe Leu Asp Tyr Ser Asp Ser Val Gly Phe
145                 150                 155                 160

Ile Phe His Asp Asp Ala Lys Arg Leu Asp Arg Asn Ala Lys Asn Arg
                165                 170                 175

Tyr Thr Val


<210> SEQ ID NO 22
<211> LENGTH: 539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

atggcaaagc atccattgga gcattcatgg actttttggt ttgatagccc tattgctaaa     60

tctcgacaaa ctgcttgggg aagctcactt cgaaatgtct acactttctc cactgttgaa    120

gatttttggg gtgcttacta taatatccat cacccaagca agttggttat gggagcagac    180

tttcattgtt ttaagcataa aattgagcca aagtgggaag atcctgtatg tgccaatgga    240

gggacgtgga aaatgagttt tccgaagggt aaatctgata ccagctggct atatacgctg    300

ctggcaatga ttggacatca attcgatcat ggagatgaaa tttgtggagc agtcgttagt    360

gtccgggcta agggagaaaa aatagctttg tggaccaaga atgctgcaaa cgaaacagct    420

caggttagca ttggcaaaca atggaagcag tttctagatt acagcgattc ggttggcttc    480
```

atatttcacg atgatgcaaa gaggctcgac agaaatgcca agaatcgtta cacagttag 539

<210> SEQ ID NO 23
<211> LENGTH: 177
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Ala Lys His Pro Leu Glu His Ser Trp Thr Phe Trp Phe Asp Ser
1               5                   10                  15

Pro Ile Pro Lys Ser Arg Gln Thr Ala Trp Gly Ser Ser Leu Arg Asn
            20                  25                  30

Val Tyr Thr Phe Ser Thr Val Glu Asp Phe Trp Gly Ala Tyr Asn Asn
        35                  40                  45

Ile His His Pro Ser Lys Leu Val His Asp Phe His Cys Phe Lys His
    50                  55                  60

Lys Ile Glu Pro Lys Trp Glu Asp Pro Val Cys Ala Asn Gly Gly Thr
65                  70                  75                  80

Trp Lys Met Asn Phe Leu Lys Gly Lys Ser Asp Thr Ser Trp Leu Tyr
                85                  90                  95

Thr Leu Leu Ala Met Ile Gly His Gln Phe Asp His Gly Asp Glu Ile
            100                 105                 110

Cys Gly Ala Val Val Ser Val Arg Ser Lys Gly Glu Lys Ile Ala Leu
        115                 120                 125

Trp Thr Lys Asn Ser Ala Asn Glu Thr Ala Gln Val Ser Ile Gly Lys
    130                 135                 140

Gln Trp Lys Gln Phe Leu Asp Tyr Ser Asp Ser Val Gly Phe Ile Phe
145                 150                 155                 160

His Asp Asp Ala Lys Arg Leu Asp Arg Ser Ala Lys Asn Arg Tyr Thr
                165                 170                 175

Val
```

<210> SEQ ID NO 24
<211> LENGTH: 534
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
atggcaaaac atccattgga gcattcatgg actttttggt ttgatagccc tattcctaaa     60

tctcgacaaa ctgcttgggg aagctcactt cgaaatgtct acactttctc cactgttgaa    120

gatttttggg gtgcttacaa taatatccat cacccaagca agttggttca cgactttcat    180

tgttttaagc ataaaattga gccaaagtgg gaagatcctg tatgtgccaa tggagggacg    240

tggaaaatga atttttgaa gggtaaatct gataccagct ggctatatac gctgctggca     300

atgattggac atcaattcga tcacggagat gaaatttgtg gagcagtcgt tagtgtccgg    360

tctaagggag aaaaaatagc tttgtggacc aagaatagtg caaatgaaac agctcaggtt    420

agcattggta agcaatggaa gcagtttcta gattacagcg attcggttgg cttcatattt    480

cacgatgatg caaagaggct cgacagaagt gccaagaatc gttacacagt atag          534
```

<210> SEQ ID NO 25

<211> LENGTH: 46
<212> TYPE: PRT
<213> ORGANISM: Artificial Sequence
<220> FEATURE:
<223> OTHER INFORMATION: Description of Artificial Sequence: Synthetic consensus sequence
<220> FEATURE:
<221> NAME/KEY: MOD_RES
<222> LOCATION: (2)..(5)
<223> OTHER INFORMATION: Any neutral amino acid
<220> FEATURE:
<221> NAME/KEY: MOD_RES
<222> LOCATION: (8)..(8)
<223> OTHER INFORMATION: Any basic amino acid
<220> FEATURE:
<221> NAME/KEY: MOD_RES
<222> LOCATION: (10)..(10)
<223> OTHER INFORMATION: Any neutral amino acid
<220> FEATURE:
<221> NAME/KEY: MOD_RES
<222> LOCATION: (16)..(16)
<223> OTHER INFORMATION: Any neutral amino acid
<220> FEATURE:
<221> NAME/KEY: MOD_RES
<222> LOCATION: (18)..(19)
<223> OTHER INFORMATION: Any neutral amino acid
<220> FEATURE:
<221> NAME/KEY: MOD_RES
<222> LOCATION: (24)..(24)
<223> OTHER INFORMATION: Any neutral amino acid
<220> FEATURE:
<221> NAME/KEY: MOD_RES
<222> LOCATION: (27)..(27)
<223> OTHER INFORMATION: Any neutral amino acid
<220> FEATURE:
<221> NAME/KEY: MOD_RES
<222> LOCATION: (30)..(31)
<223> OTHER INFORMATION: Any neutral amino acid
<220> FEATURE:
<221> NAME/KEY: MOD_RES
<222> LOCATION: (37)..(37)
<223> OTHER INFORMATION: Any basic amino acid
<220> FEATURE:
<221> NAME/KEY: MOD_RES
<222> LOCATION: (42)..(43)
<223> OTHER INFORMATION: Any neutral amino acid

<400> SEQUENCE: 25

```
Asp Xaa Xaa Xaa Xaa Lys Ser Xaa Gln Xaa Ala Trp Gly Ser Ser Xaa
1               5                   10                  15

Arg Xaa Xaa Tyr Thr Phe Ser Xaa Val Glu Xaa Phe Trp Xaa Xaa Tyr
            20                  25                  30

Asn Asn Ile His Xaa Pro Ser Lys Leu Xaa Xaa Gly Ala Asp
        35                  40                  45
```

<210> SEQ ID NO 26
<211> LENGTH: 681
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
atggcaacag ctgaaatgga gaaaacgacg acgtttgatg aagctgagaa ggtgaaattg     60

aatgctaatg aggcagatga tgaagttgaa gaaggtgaaa ttgttgaaga aactgatgat    120

acgacgtcgt atttgagcaa agaaatagca acaaagcatc cattagagca ttcatggact    180

ttctggtttg ataatccagt gccgaaatcg aaacaagctg cttggggtag ctcgcttcgc    240

aacgtctaca ctttctccac tgttgaagat ttttggggtg cttacaataa tatccaccac    300
```

```
ccaagcaagt tagttcacga cttacattgt ttcaagcata aaattgagcc aaagtgggaa    360

gatcctgtat gtgccaatgg agggacatgg aaaatgagtt tttcaaaggg taaatctgat    420

accagctggc tatatacgct gcttgcaatg attggacatc aattcgatca tgaagatgaa    480

atttgtgggg cagtagttag tgtcagaggt aagggagaaa aaatatcttt gtggaccaag    540

aattctgcaa atgaaacggc tcaggttagc attggtaagc aatggaagca gtttctggat    600

tacagcgaca gtgttggctt catatttcac gacgatgcaa agaggctcga cagaaatgca    660

aagaatcgtt acaccgtata g                                              681
```

```
<210> SEQ ID NO 27
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Val Pro Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val His Asp Leu His Cys Phe Lys
            100                 105                 110

His Lys Ile Glu Pro Lys Trp Glu Asp Pro Val Cys Ala Asn Gly Gly
        115                 120                 125

Thr Trp Lys Met Ser Phe Ser Lys Gly Lys Ser Asp Thr Ser Trp Leu
    130                 135                 140

Tyr Thr Leu Leu Ala Met Ile Gly His Gln Phe Asp His Glu Asp Glu
145                 150                 155                 160

Ile Cys Gly Ala Val Val Ser Val Arg Gly Lys Gly Glu Lys Ile Ser
                165                 170                 175

Leu Trp Thr Lys Asn Ser Ala Asn Glu Thr Ala Gln Val Ser Ile Gly
            180                 185                 190

Lys Gln Trp Lys Gln Phe Leu Asp Tyr Ser Asp Ser Val Gly Phe Ile
        195                 200                 205

Phe His Asp Asp Ala Lys Arg Leu Asp Arg Asn Ala Lys Asn Arg Tyr
    210                 215                 220

Thr Val
225
```

```
<210> SEQ ID NO 28
<211> LENGTH: 681
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 28

```
atggcaacag ctgaaatgga gaaaacgacg acgtttgatg aagctgagaa ggtgaaattg     60

aatgctaatg aggcagatga tgaagttgaa gaaggtgaaa ttgttgaaga aactgatgat    120

acgacgtcgt atttgagcaa agaaatagca acaaagcatc cattagagca ttcatggact    180

ttctggtttg ataatccagt gccgaaatcg aaacaagctg cttggggtag ctcgcttcgc    240

aacgtctaca ctttctccac tgttgaagat tttggggtg cttacaataa tatccaccac    300

ccaagcaagt tagttcacga cttacattgt ttcaagcata aaattgagcc aaagtgggaa    360

gatcctgtat gtgccaatgg agggacatgg aaaatgagtt tttcaaaggg taaatctgat    420

accagctggc tatatacgct gcttgcaatg attggacatc aattcgatca tgaagatgaa    480

atttgtgggg cagtagttag tgtcagaggt aagggagaaa aaatatcttt gtggaccaag    540

aattctgcaa atgaaacggc tcaggttagc attggtaagc aatggaagca gtttctggat    600

tacagcgaca gtgttggctt catatttcac gacgatgcaa agaggctcga cagaaatgca    660

aagaatcgtt acaccgtata g                                              681
```

<210> SEQ ID NO 29
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Val Pro Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val His Asp Leu His Cys Phe Lys
            100                 105                 110

His Lys Ile Glu Pro Lys Trp Glu Asp Pro Val Cys Ala Asn Gly Gly
        115                 120                 125

Thr Trp Lys Met Ser Phe Ser Lys Gly Lys Ser Asp Thr Ser Trp Leu
    130                 135                 140

Tyr Thr Leu Leu Ala Met Ile Gly His Gln Phe Asp His Glu Asp Glu
145                 150                 155                 160

Ile Cys Gly Ala Val Val Ser Val Arg Gly Lys Gly Glu Lys Ile Ser
                165                 170                 175

Leu Trp Thr Lys Asn Ser Ala Asn Glu Thr Ala Gln Val Ser Ile Gly
            180                 185                 190

Lys Gln Trp Lys Gln Phe Leu Asp Tyr Ser Asp Ser Val Gly Phe Ile
        195                 200                 205

Phe His Asp Asp Ala Lys Arg Leu Asp Arg Asn Ala Lys Asn Arg Tyr
    210                 215                 220
```

Thr Val
225

<210> SEQ ID NO 30
<211> LENGTH: 690
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30
atggcagcag ctgaaatgga gagaacgacg tcgtttgatg cagctgagaa gttgaaggcc 60
gccgatgcag gaggaggaga ggtagacgat gaacttgaag aaggtgaaat tgttgaagaa 120
tcaaatgata cggcgtcgta tttagggaaa gaaatcacag tgaaacatcc attggagcat 180
tcatggactt tttggtttga tagccctatt cctaaatctc gacaaactgc ttggggaagc 240
tcacttcgaa atgtctacac tttctccact gttgaagagt tttggggtgc ttacaataat 300
atccatcacc caagcaagtt ggttcacgac tttcattgtt ttaagcataa aattgagcca 360
aagtgggaag atcctgtatg tgccaatgga gggacgtgga aaatgaattt tttgaagggt 420
aaatctgata ccagctggct atatacgctg ctggcaatga ttggacatca attcgatcac 480
ggagatgaaa tttgtggagc agtcgttagt gtccggtcta agggagaaaa aatagctttg 540
tggaccaaga atactgcaaa tgaaacagct caggttagca ttggtaagca atggaagcag 600
tttctagatt acagcgattc ggttggcttc atatttcacg atgatgcaaa gaggctcgac 660
agaagtgcca agaatcgtta ttccgtgtag 690

<210> SEQ ID NO 31
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Met Ala Ala Ala Glu Met Glu Arg Thr Thr Ser Phe Asp Ala Ala Glu
1 5 10 15

Lys Leu Lys Ala Ala Asp Ala Gly Gly Gly Glu Val Asp Asp Glu Leu
20 25 30

Glu Glu Gly Glu Ile Val Glu Glu Ser Asn Asp Thr Ala Ser Tyr Leu
35 40 45

Gly Lys Glu Ile Thr Val Lys His Pro Leu Glu His Ser Trp Thr Phe
50 55 60

Trp Phe Asp Ser Pro Ile Pro Lys Ser Arg Gln Thr Ala Trp Gly Ser
65 70 75 80

Ser Leu Arg Asn Val Tyr Thr Phe Ser Thr Val Glu Glu Phe Trp Gly
85 90 95

Ala Tyr Asn Asn Ile His His Pro Ser Lys Leu Val His Asp Phe His
100 105 110

Cys Phe Lys His Lys Ile Glu Pro Lys Trp Glu Asp Pro Val Cys Ala
115 120 125

Asn Gly Gly Thr Trp Lys Met Asn Phe Leu Lys Gly Lys Ser Asp Thr
130 135 140

Ser Trp Leu Tyr Thr Leu Leu Ala Met Ile Gly His Gln Phe Asp His
145 150 155 160

```
Gly Asp Glu Ile Cys Gly Ala Val Val Ser Val Arg Ser Lys Gly Glu
                165                 170                 175

Lys Ile Ala Leu Trp Thr Lys Asn Thr Ala Asn Glu Thr Ala Gln Val
            180                 185                 190

Ser Ile Gly Lys Gln Trp Lys Gln Phe Leu Asp Tyr Ser Asp Ser Val
        195                 200                 205

Gly Phe Ile Phe His Asp Asp Ala Lys Arg Leu Asp Arg Ser Ala Lys
    210                 215                 220

Asn Arg Tyr Ser Val
225


<210> SEQ ID NO 32
<211> LENGTH: 228
<212> TYPE: PRT
<213> ORGANISM: Capsicum sp.

<400> SEQUENCE: 32

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Arg Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220

Arg Tyr Thr Val
225


<210> SEQ ID NO 33
<211> LENGTH: 416
<212> TYPE: DNA
<213> ORGANISM: Solanum sp.

<400> SEQUENCE: 33

gtttacagta ccatatatcc tgtcagaggt atagaggcat gactggcatg atcactaaat      60

tgatgcccac agaggagact tataacctac aggggcacgt agttctagga cttgaaagtg     120
```

```
actgaccgta gtccaactcg gtataaagcc tactcccaac taaatatatg aaatttatag    180

cataactgca gatgagctcg attctagagt aggtaccgag ctcgaattcc ttactcctcc    240

acaaagccgt aactgaagcg acttctattt ttctcaacct tcggacctga cgatcaagaa    300

tctcaatagg tagttcttca taagtgagac tatccttcat agctacactt tctaaaggta    360

cgatagattt tggatcaacc acacacactt cgtttacacc ggtatatatc ctgcca        416


<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (16)..(16)
<223> OTHER INFORMATION: a, c, t, g, unknown or other

<400> SEQUENCE: 34

ygryaggata tatwsnvbkg taawy                                           25


<210> SEQ ID NO 35
<211> LENGTH: 231
<212> TYPE: PRT
<213> ORGANISM: Solanum sp.

<400> SEQUENCE: 35

Met Ala Ala Ala Glu Met Glu Arg Thr Thr Ser Phe Asp Ala Ala Asp
1               5                   10                  15

Lys Leu Lys Ala Ala Asp Ala Gly Gly Gly Glu Val Asp Asp Glu Leu
            20                  25                  30

Glu Glu Gly Glu Ile Val Glu Glu Ser Asn Asp Thr Ala Ser Tyr Leu
        35                  40                  45

Gly Lys Glu Ile Thr Val Lys His Pro Leu Glu His Ser Trp Thr Phe
    50                  55                  60

Trp Phe Asp Ser Pro Ile Ala Lys Ser Arg Gln Thr Ala Trp Gly Ser
65                  70                  75                  80

Ser Leu Arg Asn Val Tyr Thr Phe Ser Thr Val Glu Asp Phe Trp Gly
                85                  90                  95

Ala Tyr Asn Asn Ile His His Pro Ser Lys Leu Val Met Gly Ala Asp
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Ser Phe Ser Lys Gly Lys Ser
    130                 135                 140

Asp Thr Ser Trp Leu Tyr Thr Pro Leu Ala Met Ile Gly His Gln Phe
145                 150                 155                 160

Asp His Gly Asp Glu Ile Cys Gly Ala Val Val Ser Val Arg Ala Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Asn
    210                 215                 220

Ala Lys Asn Arg Tyr Thr Val
```

225 230

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ggggatccat ggcaacagct gaaat 25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ccactagtct atacggtgta acgat 25

<210> SEQ ID NO 38
<211> LENGTH: 46
<212> TYPE: PRT
<213> ORGANISM: Artificial Sequence
<220> FEATURE:
<223> OTHER INFORMATION: Description of Artificial Sequence: Synthetic consensus sequence
<220> FEATURE:
<221> NAME/KEY: MOD_RES
<222> LOCATION: (2)..(5)
<223> OTHER INFORMATION: Any neutral amino acid
<220> FEATURE:
<221> NAME/KEY: MOD_RES
<222> LOCATION: (8)..(8)
<223> OTHER INFORMATION: Any neutral amino acid
<220> FEATURE:
<221> NAME/KEY: MOD_RES
<222> LOCATION: (10)..(10)
<223> OTHER INFORMATION: Any neutral amino acid
<220> FEATURE:
<221> NAME/KEY: MOD_RES
<222> LOCATION: (16)..(16)
<223> OTHER INFORMATION: Any neutral amino acid
<220> FEATURE:
<221> NAME/KEY: MOD_RES
<222> LOCATION: (18)..(19)
<223> OTHER INFORMATION: Any neutral amino acid
<220> FEATURE:
<221> NAME/KEY: MOD_RES
<222> LOCATION: (24)..(24)
<223> OTHER INFORMATION: Any neutral amino acid
<220> FEATURE:
<221> NAME/KEY: MOD_RES
<222> LOCATION: (27)..(27)
<223> OTHER INFORMATION: Any neutral amino acid
<220> FEATURE:
<221> NAME/KEY: MOD_RES
<222> LOCATION: (30)..(31)
<223> OTHER INFORMATION: Any neutral amino acid
<220> FEATURE:
<221> NAME/KEY: MOD_RES
<222> LOCATION: (37)..(37)
<223> OTHER INFORMATION: Any neutral amino acid
<220> FEATURE:
<221> NAME/KEY: MOD_RES
<222> LOCATION: (42)..(43)
<223> OTHER INFORMATION: Any neutral amino acid

<400> SEQUENCE: 38

```
Asp Xaa Xaa Xaa Xaa Lys Ser Xaa Gln Xaa Ala Trp Gly Ser Ser Xaa
1               5                   10                  15

Arg Xaa Xaa Tyr Thr Phe Ser Xaa Val Glu Xaa Phe Trp Xaa Xaa Tyr
            20                  25                  30

Asn Asn Ile His Xaa Pro Ser Lys Leu Xaa Xaa Gly Ala Asp
        35                  40                  45
```

<210> SEQ ID NO 39
<211> LENGTH: 25
<212> TYPE: DNA
<213> ORGANISM: Agrobacterium sp.

<400> SEQUENCE: 39
tgacaggata tattggcggg taaac 25

<210> SEQ ID NO 40
<211> LENGTH: 25
<212> TYPE: DNA
<213> ORGANISM: Agrobacterium sp.

<400> SEQUENCE: 40
tggcaggata tattgtggtg taaac 25

<210> SEQ ID NO 41
<211> LENGTH: 25
<212> TYPE: DNA
<213> ORGANISM: Agrobacterium sp.

<400> SEQUENCE: 41
tggcaggata tataccgttg taatt 25

<210> SEQ ID NO 42
<211> LENGTH: 25
<212> TYPE: DNA
<213> ORGANISM: Agrobacterium sp.

<400> SEQUENCE: 42
cggcaggata tattcaattg taatt 25

<210> SEQ ID NO 43
<211> LENGTH: 25
<212> TYPE: DNA
<213> ORGANISM: Unknown
<220> FEATURE:
<223> OTHER INFORMATION: Description of Unknown: LB mutant oligonucleotide

<400> SEQUENCE: 43
tggtaggata tataccgttg taatt 25

<210> SEQ ID NO 44
<211> LENGTH: 25
<212> TYPE: DNA
<213> ORGANISM: Unknown
<220> FEATURE:
<223> OTHER INFORMATION: Description of Unknown: LB mutant oligonucleotide

<400> SEQUENCE: 44
tggcaggata tatggtactg taatt 25

<210> SEQ ID NO 45
<211> LENGTH: 25
<212> TYPE: DNA

<213> ORGANISM: Unknown
<220> FEATURE:
<223> OTHER INFORMATION: Description of Unknown: Border motif sequence
<220> FEATURE:
<221> NAME/KEY: modified_base
<222> LOCATION: (16)..(16)
<223> OTHER INFORMATION: a, c, t, g, unknown or other

<400> SEQUENCE: 45
ygryaggata tatwsnvbkg taawy 25

<210> SEQ ID NO 46
<211> LENGTH: 25
<212> TYPE: DNA
<213> ORGANISM: Rhizobium leguminosarum

<400> SEQUENCE: 46
cggcaggata tatcctgatg taaat 25

<210> SEQ ID NO 47
<211> LENGTH: 25
<212> TYPE: DNA
<213> ORGANISM: Thermoanaerobacter tengcongensis

<400> SEQUENCE: 47
tggcaggagt tattcgaggg taaac 25

<210> SEQ ID NO 48
<211> LENGTH: 25
<212> TYPE: DNA
<213> ORGANISM: Arabidopsis thaliana

<400> SEQUENCE: 48
tgacaggata tatcgtgatg tcaac 25

<210> SEQ ID NO 49
<211> LENGTH: 25
<212> TYPE: DNA
<213> ORGANISM: Arabidopsis thaliana

<400> SEQUENCE: 49
gggaagtaca tattggcggg taaac 25

<210> SEQ ID NO 50
<211> LENGTH: 25
<212> TYPE: DNA
<213> ORGANISM: Oryza sativa

<400> SEQUENCE: 50
ttacaggata tattaatatg tatga 25

<210> SEQ ID NO 51
<211> LENGTH: 25
<212> TYPE: DNA
<213> ORGANISM: Homo sapiens

<400> SEQUENCE: 51
taacatgata tattcccttg taaat 25

<210> SEQ ID NO 52
<211> LENGTH: 25
<212> TYPE: DNA
<213> ORGANISM: Solanum sp.

<400> SEQUENCE: 52

```
tgacaggata tatggtaatg taaac                                             25


<210> SEQ ID NO 53
<211> LENGTH: 25
<212> TYPE: DNA
<213> ORGANISM: Solanum sp.

<400> SEQUENCE: 53

tggcaggata tataccgatg taaac                                             25


<210> SEQ ID NO 54
<211> LENGTH: 228
<212> TYPE: PRT
<213> ORGANISM: Capsicum sp.

<400> SEQUENCE: 54

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Ala Lys His Pro Leu Glu His Ser Trp Thr Phe Trp Phe Asp
    50                  55                  60

Asn Thr Val Ala Lys Ser Arg Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Arg Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220

Arg Tyr Thr Val
225


<210> SEQ ID NO 55
<211> LENGTH: 228
<212> TYPE: PRT
<213> ORGANISM: Capsicum sp.

<400> SEQUENCE: 55

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30
```

```
Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Arg Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220

Arg Tyr Thr Val
225


<210> SEQ ID NO 56
<211> LENGTH: 228
<212> TYPE: PRT
<213> ORGANISM: Capsicum sp.

<400> SEQUENCE: 56

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Arg Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asn Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
```

```
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220

Arg Tyr Thr Val
225


<210> SEQ ID NO 57
<211> LENGTH: 228
<212> TYPE: PRT
<213> ORGANISM: Capsicum sp.

<400> SEQUENCE: 57

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Gly Ser Val Gly
        195                 200                 205

Phe Ile Phe His Asp Asp Ala Lys Arg Leu Asp Arg Asn Ala Lys Asn
    210                 215                 220

Arg Tyr Thr Val
225


<210> SEQ ID NO 58
<211> LENGTH: 228
<212> TYPE: PRT
<213> ORGANISM: Capsicum sp.

<400> SEQUENCE: 58

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
```

```
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220

Arg Tyr Thr Val
225


<210> SEQ ID NO 59
<211> LENGTH: 228
<212> TYPE: PRT
<213> ORGANISM: Capsicum sp.

<400> SEQUENCE: 59

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Thr Glu Ala Lys Ser Lys Gln Asp Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160
```

```
Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asn Arg Asn Ala Lys Asn
    210                 215                 220

Arg Tyr Thr Val
225
```

<210> SEQ ID NO 60
<211> LENGTH: 228
<212> TYPE: PRT
<213> ORGANISM: Capsicum sp.

<400> SEQUENCE: 60

```
Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Val Glu Lys Ser Lys Gln Asp Asp Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Gly Ser Val Gly
        195                 200                 205

Phe Ile Phe His Asp Asp Ala Lys Arg Leu Asp Arg Asn Ala Lys Asn
    210                 215                 220

Arg Tyr Thr Val
225
```

<210> SEQ ID NO 61
<211> LENGTH: 228
<212> TYPE: PRT
<213> ORGANISM: Capsicum sp.

<400> SEQUENCE: 61

```
Met Ala Thr Ala Glu Met Glu Lys Thr Thr Thr Phe Asp Glu Ala Glu
1               5                   10                  15
```

```
Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Arg Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Gly Ser Val Gly
        195                 200                 205

Phe Ile Phe His Asp Asp Ala Lys Arg Leu Asp Arg Asn Ala Lys Asn
    210                 215                 220

Arg Tyr Thr Val
225


<210> SEQ ID NO 62
<211> LENGTH: 228
<212> TYPE: PRT
<213> ORGANISM: Capsicum sp.

<400> SEQUENCE: 62

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Val Glu Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Arg Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160
```

```
Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220

Arg Tyr Thr Val
225


<210> SEQ ID NO 63
<211> LENGTH: 228
<212> TYPE: PRT
<213> ORGANISM: Capsicum sp.

<400> SEQUENCE: 63

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Val Glu Lys Ser Lys Gln Asp Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Gly Ser Val Gly
        195                 200                 205

Phe Ile Phe His Asp Asp Ala Lys Arg Leu Asp Arg Asn Ala Lys Asn
    210                 215                 220

Arg Tyr Thr Val
225


<210> SEQ ID NO 64
<211> LENGTH: 231
<212> TYPE: PRT
<213> ORGANISM: Solanum sp.

<400> SEQUENCE: 64

Met Ala Ala Ala Glu Met Glu Arg Thr Met Ser Phe Asp Ala Ala Glu
1               5                   10                  15
```

```
Lys Leu Lys Ala Ala Asp Gly Gly Gly Gly Glu Val Asp Asp Glu Leu
            20                  25                  30

Glu Glu Gly Glu Ile Val Glu Glu Ser Asn Asp Thr Ala Ser Tyr Phe
        35                  40                  45

Gly Lys Glu Ile Thr Val Lys His Pro Leu Glu His Ser Trp Thr Phe
    50                  55                  60

Trp Phe Asp Lys Ser Thr Thr Lys Ser Arg Gln Thr Asp Trp Gly Ser
65                  70                  75                  80

Ser Leu Arg Asn Leu Tyr Thr Phe Ser Thr Val Glu Asp Phe Trp Gly
                85                  90                  95

Ala Tyr Asn Asn Ile His His Pro Ser Lys Leu Ile Ile Gly Ala Asp
            100                 105                 110

Phe His Cys Phe Lys His Lys Ile Glu Pro Gln Trp Glu Asp Pro Val
        115                 120                 125

Cys Ala Asn Gly Gly Thr Trp Lys Met Ser Phe Ser Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Ser Val Arg Ala Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Ser
    210                 215                 220

Ala Lys Asn Arg Tyr Thr Val
225                 230
```

<210> SEQ ID NO 65
<211> LENGTH: 50
<212> TYPE: PRT
<213> ORGANISM: Solanum sp.

<400> SEQUENCE: 65

```
Met Ala Ala Ala Glu Met Glu Arg Thr Met Ser Phe Asp Ala Ala Glu
1               5                   10                  15

Lys Leu Lys Ala Ala Asp Gly Gly Gly Gly Glu Val Asp Asp Glu Leu
            20                  25                  30

Glu Glu Gly Glu Ile Val Glu Glu Ser Asn Asp Thr Ala Ser Tyr Leu
        35                  40                  45

Gly Lys
    50
```

<210> SEQ ID NO 66
<211> LENGTH: 230
<212> TYPE: PRT
<213> ORGANISM: Lactuca sativa

<400> SEQUENCE: 66

```
Met Lys Ser Glu Glu Gln Lys Leu Ile Asp Val Asn Lys His Arg Gly
1               5                   10                  15

Val Arg Ser Asp Gly Glu Glu Asp Glu Gln Leu Glu Glu Gly Glu Ile
            20                  25                  30

Val Gly Gly Asp Ala Asp Thr Leu Ser Ser Ser Ser Ser Ser Arg Pro
        35                  40                  45
```

```
Gly Thr Ala Ile Ala Gln His Pro Leu Glu His Ser Trp Thr Phe Trp
    50                  55                  60

Phe Asp Thr Pro Ser Pro Lys Ser Lys Gln Val Ala Trp Gly Ser Ser
65                  70                  75                  80

Met Arg Pro Ile Tyr Thr Phe Ser Ser Val Glu Glu Phe Trp Ser Leu
                85                  90                  95

Tyr Asn Asn Ile His Arg Pro Ser Lys Leu Ala Gln Gly Ala Asp Phe
            100                 105                 110

Tyr Cys Phe Lys Asn Lys Ile Glu Pro Lys Trp Glu Asp Pro Val Cys
        115                 120                 125

Ala Asn Gly Gly Lys Trp Thr Met Thr Phe Thr Lys Ala Lys Ser Asp
    130                 135                 140

Thr Cys Trp Leu Tyr Thr Leu Leu Ala Met Ile Gly Glu Gln Phe Asp
145                 150                 155                 160

His Gly Asp Asp Ile Cys Gly Ala Val Val Asn Val Arg Ala Arg Gln
                165                 170                 175

Glu Lys Ile Ala Leu Trp Thr Lys Asn Ala Ala Asn Glu Ser Ala Gln
            180                 185                 190

Leu Ser Ile Gly Lys Gln Trp Lys Glu Phe Ile Asp Tyr Asn Asp Thr
        195                 200                 205

Ile Gly Phe Ile Phe His Glu Asp Ala Lys Thr Leu Asp Arg Ser Ala
    210                 215                 220

Lys Asn Lys Tyr Thr Val
225                 230


<210> SEQ ID NO 67
<211> LENGTH: 228
<212> TYPE: PRT
<213> ORGANISM: Lactuca sativa

<400> SEQUENCE: 67

Met Lys Ser Glu Glu Gln Lys Leu Ile Asp Val Asn Lys His Arg Gly
1               5                   10                  15

Val Arg Ser Asp Gly Glu Glu Asp Glu Gln Leu Glu Glu Gly Glu Ile
            20                  25                  30

Val Gly Gly Asp Ala Asp Thr Leu Ser Ser Ser Ser Ser Ser Arg Pro
        35                  40                  45

Gly Thr Ala Ile Ala Gln His Pro Leu Glu His Ser Trp Thr Phe Trp
    50                  55                  60

Phe Asp Thr Pro Ser Ala Lys Ser Lys Gln Val Ala Trp Gly Ser Ser
65                  70                  75                  80

Met Arg Pro Ile Tyr Thr Phe Ser Ser Val Glu Glu Phe Trp Ser Leu
                85                  90                  95

Tyr Asn Asn Ile His Arg Pro Ser Lys Leu Ala His Asp Phe Tyr Cys
            100                 105                 110

Phe Lys Asn Lys Ile Glu Pro Lys Trp Glu Asp Pro Val Cys Ala Asn
        115                 120                 125

Gly Gly Lys Trp Thr Met Thr Phe Thr Lys Ala Lys Ser Asp Thr Cys
    130                 135                 140

Trp Leu Tyr Thr Leu Leu Ala Met Ile Gly Glu Gln Phe Asp His Gly
145                 150                 155                 160

Asp Asp Ile Cys Gly Ala Val Val Asn Val Arg Ala Arg Gln Glu Lys
                165                 170                 175

Ile Ala Leu Trp Thr Lys Asn Ser Ala Asn Glu Ser Ala Gln Leu Ser
```

```
            180                 185                 190

Ile Gly Lys Gln Trp Lys Glu Phe Ile Asp Tyr Asn Asp Thr Ile Gly
        195                 200                 205

Phe Ile Phe His Glu Asp Ala Lys Thr Leu Asp Arg Ser Ala Lys Asn
    210                 215                 220

Lys Tyr Thr Val
225


<210> SEQ ID NO 68
<211> LENGTH: 228
<212> TYPE: PRT
<213> ORGANISM: Pisum sp.

<400> SEQUENCE: 68

Met Val Val Glu Glu Thr Pro Lys Ser Ile Ile Thr Asp Asp Gln Ile
1               5                   10                  15

Thr Thr Asn Pro Asn Arg Val Ile Glu Asp Asp Asn Asn Leu Glu Glu
            20                  25                  30

Gly Glu Ile Leu Asp Glu Asp Asp Ser Ser Ala Thr Ser Lys Pro Val
        35                  40                  45

Val His Gln Pro His Leu Leu Glu Asn Ser Trp Thr Phe Leu Phe Asp
    50                  55                  60

Thr Pro Ala Ala Lys Ser Lys Gln Asp Asp Trp Gly Ser Ser Met Arg
65                  70                  75                  80

Pro Ile Tyr Thr Phe Ser Thr Val Glu Glu Phe Trp Ser Ile Tyr Asn
                85                  90                  95

Asn Ile His His Pro Gly Lys Leu Ala Val Arg Ala Asp Phe Tyr Cys
            100                 105                 110

Phe Lys His Lys Ile Glu Pro Lys Trp Glu Asp Pro Ile Cys Ala Asn
        115                 120                 125

Gly Gly Lys Trp Thr Ala Asn Tyr Pro Lys Gly Lys Ser Asp Thr Ser
    130                 135                 140

Trp Leu Tyr Thr Leu Leu Ala Met Ile Gly Glu Gln Phe Asp His Gly
145                 150                 155                 160

Asp Glu Ile Cys Gly Ala Val Val Lys Val Arg Gly Arg Ala Glu Lys
                165                 170                 175

Ile Ser Ile Trp Thr Lys Asn Ala Ser Asn Glu Ala Ala Gln Val Ser
            180                 185                 190

Ile Gly Lys Gln Trp Lys Glu Phe Leu Asp Tyr Asn Glu Thr Met Gly
        195                 200                 205

Phe Ile Phe His Asp Asp Ala Arg Lys Leu Asp Arg Asn Ala Lys Asn
    210                 215                 220

Lys Tyr Val Val
225


<210> SEQ ID NO 69
<211> LENGTH: 227
<212> TYPE: PRT
<213> ORGANISM: Pisum sp.

<400> SEQUENCE: 69

Met Val Val Glu Glu Thr Pro Lys Ser Ile Ile Thr Asp Asp Gln Ile
1               5                   10                  15

Thr Thr Asn Pro Asn Arg Val Ile Glu Asp Asp Asn Asn Leu Glu Glu
            20                  25                  30

Gly Glu Ile Leu Asp Glu Asp Asp Ser Ser Ala Thr Ser Lys Pro Val
```

```
        35                  40                  45

Val His Gln Pro His Leu Leu Glu Asn Ser Trp Thr Phe Trp Phe Asp
    50                  55                  60

Thr Pro Ala Ala Lys Ser Lys Gln Pro Asp Trp Gly Ser Met Arg Pro
65                  70                  75                  80

Ile Tyr Thr Phe Ser Thr Val Glu Glu Phe Trp Ser Ile Tyr Asn Asn
                85                  90                  95

Ile His His Pro Gly Lys Leu Ala Val Gly Ala Asp Phe Tyr Cys Phe
            100                 105                 110

Lys His Lys Ile Glu Pro Lys Trp Glu Asp Pro Ile Cys Ala Asn Gly
        115                 120                 125

Gly Lys Trp Thr Ala Asn Tyr Pro Lys Gly Lys Ser Asp Thr Ser Trp
    130                 135                 140

Leu Tyr Thr Leu Leu Ala Met Ile Gly Glu Gln Phe Asp His Gly Asp
145                 150                 155                 160

Glu Ile Cys Gly Ala Val Val Asn Val Arg Gly Arg Ala Glu Lys Ile
                165                 170                 175

Ser Ile Trp Thr Lys Asn Ala Ser Asn Glu Ala Ala Gln Val Ser Ile
            180                 185                 190

Gly Lys Gln Trp Lys Glu Phe Leu Asp Tyr Asn Glu Thr Met Gly Phe
        195                 200                 205

Ile Phe His Asp Asp Ala Arg Lys Leu Asp Arg Asn Ala Lys Asn Lys
    210                 215                 220

Tyr Val Val
225


<210> SEQ ID NO 70
<211> LENGTH: 215
<212> TYPE: PRT
<213> ORGANISM: Phaseolus sp.

<400> SEQUENCE: 70

Lys Ser Thr Ile Thr Asp Glu Gln Asn Pro Ser Arg Val Asp Asn Asp
1               5                   10                  15

Asp Asp Asp Leu Glu Asp Gly Glu Ile Leu Glu Asp Ala Asp Asp Ala
            20                  25                  30

Ala Ser Ala Ala Ser Lys Pro Pro Ser Ala Phe Leu Arg Lys Pro His
        35                  40                  45

Pro Leu Glu Asn Ser Trp Thr Phe Trp Tyr Asp Asn Pro Ser Ala Lys
    50                  55                  60

Ser Lys Gln Ala Glu Trp Gly Ser Ser Ile Arg Pro Ile Tyr Thr Phe
65                  70                  75                  80

Ser Thr Val Glu Glu Phe Trp Ser Ile Tyr Asn Asn Ile His His Pro
                85                  90                  95

Ser Lys Leu Gly Val Gly Ala Gly Phe His Cys Phe Lys His Lys Ile
            100                 105                 110

Glu Pro Lys Trp Glu Asp Pro Ile Cys Ala Asn Gly Gly Lys Trp Thr
        115                 120                 125

Met Thr Phe Gln Arg Gly Lys Ser Asp Thr Ser Trp Leu Tyr Thr Leu
    130                 135                 140

Leu Ala Met Ile Gly Glu Gln Phe Asp Tyr Gly Asp Glu Ile Cys Gly
145                 150                 155                 160

Ala Val Val Asn Val Arg Asn Arg Gln Asp Lys Ile Ser Ile Trp Thr
                165                 170                 175
```

```
Lys Asn Ala Ser Asn Glu Ala Ala Gln Met Ser Ile Gly Lys Gln Trp
            180                 185                 190

Lys Glu Phe Leu Asp Tyr Asn Glu Pro Ile Gly Phe Ile Phe His Glu
        195                 200                 205

Asp Ala Lys Lys His Glu Arg
    210                 215


<210> SEQ ID NO 71
<211> LENGTH: 235
<212> TYPE: PRT
<213> ORGANISM: Unknown
<220> FEATURE:
<223> OTHER INFORMATION: Description of Unknown: melon eIF4E polypeptide
      sequence

<400> SEQUENCE: 71

Met Val Val Glu Asp Ser Met Lys Ala Thr Ser Ala Glu Asp Leu Ser
1               5                   10                  15

Asn Ser Ile Ala Asn Gln Asn Pro Arg Gly Arg Gly Gly Asp Glu Asp
            20                  25                  30

Glu Glu Leu Glu Glu Gly Glu Ile Val Gly Asp Asp Asp Leu Asp Ser
        35                  40                  45

Ser Asn Leu Ser Ala Ser Leu Val His Gln Pro His Pro Leu Glu His
    50                  55                  60

Ser Trp Thr Phe Trp Phe Asp Asn Pro Ser Ala Lys Ser Lys Gln Ala
65                  70                  75                  80

Thr Trp Gly Ala Ser Ile Arg Pro Ile Tyr Thr Phe Ser Thr Val Glu
                85                  90                  95

Glu Phe Trp Ser Val Tyr Asn Asn Ile His His Pro Ser Lys Leu Ala
            100                 105                 110

Met Arg Ala Asp Leu Tyr Cys Phe Lys His Lys Ile Glu Pro Lys Trp
        115                 120                 125

Glu Asp Pro Val Cys Ala Asn Gly Gly Lys Trp Thr Val Asn Phe Pro
    130                 135                 140

Arg Gly Lys Ser Asp Asn Gly Trp Leu Tyr Thr Leu Leu Ala Met Ile
145                 150                 155                 160

Gly Glu Gln Phe Asp Cys Gly Asp Glu Ile Cys Gly Ala Val Val Asn
                165                 170                 175

Val Arg Ser Gly Gln Asp Lys Ile Ser Ile Trp Thr Lys Asn Ala Ser
            180                 185                 190

Asn Glu Ala Ala Gln Ala Ser Ile Gly Lys Gln Trp Lys Glu Phe Leu
        195                 200                 205

Asp Tyr Asn Glu Ser Ile Gly Phe Ile Phe His Asp Asp Ala Lys Lys
    210                 215                 220

Phe Asp Arg Leu Ala Lys Asn Lys Tyr Met Val
225                 230                 235


<210> SEQ ID NO 72
<211> LENGTH: 215
<212> TYPE: PRT
<213> ORGANISM: Hordeum sp.

<400> SEQUENCE: 72

Met Ala Glu Asp Thr Glu Thr Trp Pro Ala Ser Ala Gly Ala Glu Glu
1               5                   10                  15

Arg Glu Glu Gly Glu Ile Ala Asp Asp Gly Asp Gly Ser Ala Ala Ala
            20                  25                  30
```

```
Ala Ala Gly Arg Val Ser Ala His Pro Leu Glu Asn Ala Trp Thr Phe
        35                  40                  45

Trp Phe Asp Asn Thr Gln Gly Lys Phe Arg Ala Val Ala Trp Gly Ser
    50                  55                  60

Thr Ile His Pro Ile His Thr Phe Ser Thr Val Glu Asp Phe Trp Ser
65                  70                  75                  80

Leu Tyr Asn Asn Ile His His Pro Ser Lys Leu Asn Val Gly Ala Asp
                85                  90                  95

Phe His Cys Phe Lys Asp Lys Ile Glu Pro Lys Trp Glu Asp Pro Ile
            100                 105                 110

Cys Ala Asn Gly Gly Thr Trp Thr Ile Ser Cys Gly Lys Gly Lys Ser
        115                 120                 125

Asp Thr Phe Trp Leu His Thr Leu Leu Ala Leu Ile Gly Glu Gln Phe
    130                 135                 140

Asp Phe Gly Asp Glu Ile Cys Gly Ala Val Val Ser Val Arg Lys Asn
145                 150                 155                 160

Gln Glu Arg Val Ala Ile Trp Thr Lys Asn Ala Ala Asn Glu Thr Ala
                165                 170                 175

Gln Ile Ser Ile Gly Lys Gln Trp Lys Glu Phe Leu Asp Tyr Lys Asp
            180                 185                 190

Ser Ile Gly Phe Val Val His Glu Asp Ala Lys Arg Ser Asp Lys Gly
        195                 200                 205

Ala Lys Asn Arg Tyr Thr Val
    210                 215


<210> SEQ ID NO 73
<211> LENGTH: 215
<212> TYPE: PRT
<213> ORGANISM: Hordeum sp.

<400> SEQUENCE: 73

Met Ala Glu Asp Thr Glu Thr Arg Pro Ala Ser Ala Gly Ala Glu Glu
1               5                   10                  15

Arg Glu Glu Gly Glu Ile Ala Asp Asp Gly Asp Gly Ser Ala Ala Ala
            20                  25                  30

Ala Ala Gly Arg Val Ser Ala His Pro Leu Glu Asn Ala Trp Thr Phe
        35                  40                  45

Trp Phe Asp Asn Pro Gln Gly Lys Ser Arg Ala Val Ala Trp Gly Ser
    50                  55                  60

Thr Ile His Pro Ile His Thr Phe Ser Thr Val Glu Asp Phe Trp Ser
65                  70                  75                  80

Leu Tyr Asn Asn Ile His His Pro Ser Lys Leu Asn Val Gly Ala Asp
                85                  90                  95

Phe His Cys Phe Lys Asp Lys Ile Glu Pro Lys Trp Glu Asp Pro Ile
            100                 105                 110

Cys Ala Asn Gly Gly Lys Trp Thr Ile Ser Cys Gly Lys Gly Lys Ser
        115                 120                 125

Asp Thr Phe Trp Leu His Thr Leu Leu Ala Leu Ile Gly Glu Gln Phe
    130                 135                 140

Asp Phe Gly Asp Glu Ile Cys Gly Ala Val Val Ser Val Arg Lys Asp
145                 150                 155                 160

Lys Glu Arg Val Ala Ile Trp Thr Lys Asn Ala Ala Asn Glu Thr Ala
                165                 170                 175

Gln Ile Ser Ile Gly Lys Gln Trp Lys Glu Phe Leu Asp Tyr Lys Asp
            180                 185                 190
```

```
Ser Ile Gly Phe Val Val His Glu Asp Ala Lys Arg Ser Asp Lys Asp
        195                 200                 205

Ala Lys Asn Arg Tyr Thr Val
    210                 215


<210> SEQ ID NO 74
<211> LENGTH: 231
<212> TYPE: PRT
<213> ORGANISM: Solanum sp.

<400> SEQUENCE: 74

Met Ala Ala Ala Glu Met Glu Arg Thr Thr Ser Phe Asp Ala Ala Asp
1               5                   10                  15

Lys Leu Lys Ala Ala Asp Ala Gly Gly Gly Glu Val Asp Asp Glu Leu
            20                  25                  30

Glu Glu Gly Glu Ile Val Glu Glu Ser Asn Asp Thr Ala Ser Tyr Leu
        35                  40                  45

Gly Lys Glu Ile Thr Val Lys His Pro Leu Glu His Ser Trp Thr Phe
    50                  55                  60

Trp Phe Asp Ser Pro Ile Ala Lys Ser Arg Gln Thr Ala Trp Gly Ser
65                  70                  75                  80

Ser Leu Arg Asn Val Tyr Thr Phe Ser Thr Val Glu Asp Phe Trp Gly
                85                  90                  95

Ala Tyr Asn Asn Ile His His Pro Ser Lys Leu Val Met Gly Ala Asp
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Ser Phe Ser Lys Gly Lys Ser
    130                 135                 140

Asp Thr Ser Trp Leu Tyr Thr Pro Leu Ala Met Ile Gly His Gln Phe
145                 150                 155                 160

Asp His Gly Asp Glu Ile Cys Gly Ala Val Val Ser Val Arg Ala Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Asn
    210                 215                 220

Ala Lys Asn Arg Tyr Thr Val
225                 230


<210> SEQ ID NO 75
<211> LENGTH: 231
<212> TYPE: PRT
<213> ORGANISM: Solanum sp.

<400> SEQUENCE: 75

Met Ala Ala Ala Glu Met Glu Arg Thr Thr Ser Phe Asp Ala Ala Glu
1               5                   10                  15

Lys Leu Lys Ala Ala Asp Ala Gly Gly Gly Glu Val Asp Asp Glu Leu
            20                  25                  30

Glu Glu Gly Glu Ile Val Glu Glu Ser Asn Asp Thr Ala Ser Tyr Leu
        35                  40                  45

Gly Lys Glu Ile Thr Val Lys His Pro Leu Glu His Ser Trp Thr Phe
    50                  55                  60
```

```
Trp Phe Asp Ser Pro Ile Ala Lys Ser Arg Gln Thr Ala Trp Gly Ser
65                  70                  75                  80

Ser Leu Arg Asn Val Tyr Thr Phe Ser Thr Val Glu Glu Phe Trp Gly
                85                  90                  95

Ala Tyr Asn Asn Ile His His Pro Ser Lys Leu Val Met Gly Ala Asp
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Ser Phe Leu Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Ser Val Arg Ser Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp His Ser Asp
        195                 200                 205

Ser Val Gly Phe Ile Phe His Asp Asp Ala Lys Arg Leu Asp Arg Ser
    210                 215                 220

Ala Lys Asn Arg Tyr Thr Val
225                 230


<210> SEQ ID NO 76
<211> LENGTH: 231
<212> TYPE: PRT
<213> ORGANISM: Solanum sp.

<400> SEQUENCE: 76

Met Ala Ala Ala Glu Met Glu Arg Thr Thr Ser Phe Asp Ala Ala Glu
1               5                   10                  15

Lys Leu Lys Ala Ala Asp Ala Gly Gly Gly Glu Val Asp Asp Glu Leu
            20                  25                  30

Glu Glu Gly Glu Ile Val Glu Glu Ser Asn Asp Ala Ala Ser Tyr Leu
        35                  40                  45

Gly Lys Glu Ile Thr Val Lys His Pro Leu Glu His Ser Trp Thr Phe
    50                  55                  60

Trp Phe Asp Asn Pro Thr Ala Arg Ser Arg Gln Ile Asp Trp Gly Ser
65                  70                  75                  80

Ser Leu Arg Asn Val Tyr Thr Phe Ser Thr Val Glu Asp Phe Trp Gly
                85                  90                  95

Ala Tyr Asn Asn Ile His His Pro Ser Lys Leu Val Met Gly Ala Asp
            100                 105                 110

Phe His Cys Phe Lys His Lys Ile Glu Pro Lys Trp Glu Asp Pro Ile
        115                 120                 125

Cys Ser Asn Gly Gly Thr Trp Lys Met Ser Phe Ser Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Asn Val Arg Val Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
```

```
        195                 200                 205

Ser Val Gly Phe Ile Phe His Asp Asp Ala Lys Arg Leu Asp Arg Asn
    210                 215                 220

Ala Lys Asn Arg Tyr Thr Val
225                 230


<210> SEQ ID NO 77
<211> LENGTH: 231
<212> TYPE: PRT
<213> ORGANISM: Solanum sp.

<400> SEQUENCE: 77

Met Ala Ala Ala Glu Met Glu Arg Thr Met Ser Phe Asp Ala Ala Glu
1               5                   10                  15

Lys Leu Lys Ala Ala Asp Gly Gly Gly Gly Glu Val Asp Asp Glu Leu
            20                  25                  30

Glu Glu Gly Glu Ile Val Glu Glu Ser Asn Asp Thr Ala Ser Phe Leu
        35                  40                  45

Gly Lys Glu Ile Thr Val Lys His Pro Leu Glu His Ser Trp Thr Phe
    50                  55                  60

Trp Phe Asp Ser Pro Ile Ala Lys Ser Arg Gln Thr Ala Trp Gly Ser
65                  70                  75                  80

Ser Leu Arg Asn Val Tyr Thr Phe Ser Thr Val Glu Asp Phe Trp Gly
                85                  90                  95

Ala Tyr Tyr Asn Ile His His Pro Ser Lys Leu Val Met Gly Ala Asp
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Ser Phe Pro Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Ser Val Arg Ala Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Asn
    210                 215                 220

Ala Lys Asn Arg Tyr Thr Val
225                 230


<210> SEQ ID NO 78
<211> LENGTH: 231
<212> TYPE: PRT
<213> ORGANISM: Solanum sp.

<400> SEQUENCE: 78

Met Ala Ala Ala Glu Met Glu Arg Thr Thr Ser Phe Asp Ala Ala Glu
1               5                   10                  15

Lys Leu Lys Ala Ala Asp Ala Gly Gly Gly Glu Val Asp Asp Glu Leu
            20                  25                  30

Glu Glu Gly Glu Ile Val Glu Glu Ser Asn Asp Ala Ala Ser Tyr Leu
        35                  40                  45

Gly Lys Glu Ile Thr Val Lys His Pro Leu Glu His Ser Trp Thr Phe
```

```
    50                  55                  60

Trp Phe Asp Asn Pro Thr Ala Arg Ser Arg Gln Ile Asp Trp Gly Ser
65                  70                  75                  80

Ser Leu Arg Asn Val Tyr Thr Phe Ser Thr Val Glu Asp Phe Trp Gly
                85                  90                  95

Ala Tyr Asn Asn Ile His His Pro Ser Lys Leu Val Met Gly Ala Asp
            100                 105                 110

Phe His Cys Phe Lys His Lys Ile Glu Pro Lys Trp Glu Asp Pro Ile
        115                 120                 125

Cys Ser Asn Gly Gly Thr Trp Lys Met Ser Phe Ser Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Asn Val Arg Val Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Asn
    210                 215                 220

Ala Lys Asn Arg Tyr Thr Val
225                 230


<210> SEQ ID NO 79
<211> LENGTH: 231
<212> TYPE: PRT
<213> ORGANISM: Solanum sp.

<400> SEQUENCE: 79

Met Ala Ala Ala Glu Met Glu Arg Thr Met Ser Phe Asp Ala Ala Glu
1               5                   10                  15

Lys Leu Lys Ala Ala Asp Gly Gly Gly Gly Glu Val Asp Asp Glu Leu
            20                  25                  30

Glu Glu Gly Glu Ile Val Glu Glu Ser Asn Asp Thr Ala Ser Phe Leu
        35                  40                  45

Gly Lys Glu Ile Thr Val Lys His Pro Leu Glu His Ser Trp Thr Phe
    50                  55                  60

Trp Phe Asp Ser Pro Ile Ala Lys Ser Arg Gln Thr Ala Trp Gly Ser
65                  70                  75                  80

Ser Leu Arg Asn Val Tyr Thr Phe Ser Thr Val Glu Asp Phe Trp Gly
                85                  90                  95

Ala Tyr Tyr Asn Ile His His Pro Ser Lys Leu Val Met Gly Ala Asp
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Ser Phe Pro Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Ser Val Arg Ala Lys
                165                 170                 175

Gly Glu Lys Ile Ala Leu Trp Thr Lys Asn Ala Ala Asn Glu Thr Ala
            180                 185                 190
```

```
Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Asn
    210                 215                 220

Ala Lys Asn Arg Tyr Thr Val
225                 230


<210> SEQ ID NO 80
<211> LENGTH: 215
<212> TYPE: PRT
<213> ORGANISM: Hordeum sp.

<400> SEQUENCE: 80

Met Ala Glu Asp Thr Glu Thr Arg Pro Ala Ser Ala Gly Ala Glu Glu
1               5                   10                  15

Arg Glu Glu Gly Glu Ile Ala Asp Asp Gly Asp Gly Ser Ala Ala Ala
            20                  25                  30

Ala Ala Gly Arg Val Ser Ala His Pro Leu Glu Asn Ala Trp Thr Phe
        35                  40                  45

Trp Phe Asp Asn Pro Gln Gly Lys Ser Arg Ala Val Ala Trp Gly Ser
    50                  55                  60

Thr Ile His Pro Ile His Thr Phe Ser Thr Val Glu Asp Phe Trp Ser
65                  70                  75                  80

Leu Tyr Asn Asn Ile His His Pro Ser Lys Leu Asn Val Gly Ala Asp
                85                  90                  95

Phe His Cys Phe Lys Asp Lys Ile Glu Pro Lys Trp Glu Asp Pro Ile
            100                 105                 110

Cys Ala Asn Gly Gly Lys Trp Thr Ile Ser Cys Gly Lys Gly Lys Ser
        115                 120                 125

Asp Thr Phe Trp Leu His Thr Leu Leu Ala Leu Ile Gly Glu Gln Phe
    130                 135                 140

Asp Phe Gly Asp Glu Ile Cys Gly Ala Val Val Ser Val Arg Lys Asn
145                 150                 155                 160

Lys Glu Arg Val Ala Ile Trp Thr Lys Asn Ala Ala Asn Glu Thr Ala
                165                 170                 175

Gln Ile Ser Ile Gly Lys Gln Trp Lys Glu Phe Leu Asp Tyr Lys Asp
            180                 185                 190

Ser Ile Gly Phe Val Val His Glu Asp Ala Lys Arg Ser Asp Lys Asp
        195                 200                 205

Ala Lys Asn Arg Tyr Thr Val
    210                 215


<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

ggatccatgg cagcagctga aatg                                             24


<210> SEQ ID NO 82
<211> LENGTH: 31
<212> TYPE: DNA
<213> ORGANISM: Artificial Sequence
<220> FEATURE:
<223> OTHER INFORMATION: Description of Artificial Sequence: Synthetic
```

primer

<400> SEQUENCE: 82
actagtctat actgtgtaac gattcttggc a 31

<210> SEQ ID NO 83
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (44)..(44)
<223> OTHER INFORMATION: Thr or Ala
<220> FEATURE:
<221> NAME/KEY: MOD_RES
<222> LOCATION: (68)..(68)
<223> OTHER INFORMATION: Ser or Asn
<220> FEATURE:
<221> NAME/KEY: MOD_RES
<222> LOCATION: (70)..(70)
<223> OTHER INFORMATION: Ile or Thr
<220> FEATURE:
<221> NAME/KEY: MOD_RES
<222> LOCATION: (72)..(72)
<223> OTHER INFORMATION: Lys or Arg
<220> FEATURE:
<221> NAME/KEY: MOD_RES
<222> LOCATION: (76)..(76)
<223> OTHER INFORMATION: Thr or Ile
<220> FEATURE:
<221> NAME/KEY: MOD_RES
<222> LOCATION: (77)..(77)
<223> OTHER INFORMATION: Ala or Asp
<220> FEATURE:
<221> NAME/KEY: MOD_RES
<222> LOCATION: (128)..(128)
<223> OTHER INFORMATION: Val or Ile
<220> FEATURE:
<221> NAME/KEY: MOD_RES
<222> LOCATION: (130)..(130)
<223> OTHER INFORMATION: Ala or Ser
<220> FEATURE:
<221> NAME/KEY: MOD_RES
<222> LOCATION: (172)..(172)
<223> OTHER INFORMATION: Ser or Asn
<220> FEATURE:
<221> NAME/KEY: MOD_RES
<222> LOCATION: (175)..(175)
<223> OTHER INFORMATION: Ser or Val
<220> FEATURE:
<223> OTHER INFORMATION: The first residue listed at each MOD_RES is the amino acid of the wild-type sequence; the second residue is a possible point mutation; at least two mutations must be present

<400> SEQUENCE: 83

```
Met Ala Ala Ala Glu Met Glu Arg Thr Thr Ser Phe Asp Ala Ala Glu
1               5                   10                  15

Lys Leu Lys Ala Ala Asp Ala Gly Gly Gly Glu Val Asp Asp Glu Leu
            20                  25                  30

Glu Glu Gly Glu Ile Val Glu Glu Ser Asn Asp Xaa Ala Ser Tyr Leu
        35                  40                  45

Gly Lys Glu Ile Thr Val Lys His Pro Leu Glu His Ser Trp Thr Phe
    50                  55                  60

Trp Phe Asp Xaa Pro Xaa Ala Xaa Ser Arg Gln Xaa Xaa Trp Gly Ser
65                  70                  75                  80

Ser Leu Arg Asn Val Tyr Thr Phe Ser Thr Val Glu Asp Phe Trp Gly
                85                  90                  95
```

```
Ala Tyr Asn Asn Ile His His Pro Ser Lys Leu Val Met Gly Ala Asp
            100                 105                 110

Phe His Cys Phe Lys His Lys Ile Glu Pro Lys Trp Glu Asp Pro Xaa
        115                 120                 125

Cys Xaa Asn Gly Gly Thr Trp Lys Met Asn Phe Leu Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Xaa Val Arg Xaa Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp His Ser Asp
        195                 200                 205

Ser Val Gly Phe Ile Phe His Asp Asp Ala Lys Arg Leu Asp Arg Ser
    210                 215                 220

Ala Lys Asn Arg Tyr Thr Val
225                 230


<210> SEQ ID NO 84
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Thr or Met
<220> FEATURE:
<221> NAME/KEY: MOD_RES
<222> LOCATION: (23)..(23)
<223> OTHER INFORMATION: Ala or Gly
<220> FEATURE:
<221> NAME/KEY: MOD_RES
<222> LOCATION: (47)..(47)
<223> OTHER INFORMATION: Tyr or Phe
<220> FEATURE:
<221> NAME/KEY: MOD_RES
<222> LOCATION: (99)..(99)
<223> OTHER INFORMATION: Asn or Tyr
<220> FEATURE:
<221> NAME/KEY: MOD_RES
<222> LOCATION: (140)..(140)
<223> OTHER INFORMATION: Leu or Pro
<220> FEATURE:
<223> OTHER INFORMATION: The first residue listed at each MOD_RES is the
      amino acid of the wild-type sequence; the second residue is a
      possible point mutation; at least two mutations must be present

<400> SEQUENCE: 84

Met Ala Ala Ala Glu Met Glu Arg Thr Xaa Ser Phe Asp Ala Ala Glu
1               5                   10                  15

Lys Leu Lys Ala Ala Asp Xaa Gly Gly Gly Glu Val Asp Asp Glu Leu
            20                  25                  30

Glu Glu Gly Glu Ile Val Glu Glu Ser Asn Asp Thr Ala Ser Xaa Leu
        35                  40                  45

Gly Lys Glu Ile Thr Val Lys His Pro Leu Glu His Ser Trp Thr Phe
    50                  55                  60

Trp Phe Asp Ser Pro Ile Ala Lys Ser Arg Gln Thr Ala Trp Gly Ser
65                  70                  75                  80

Ser Leu Arg Asn Val Tyr Thr Phe Ser Thr Val Glu Asp Phe Trp Gly
                85                  90                  95
```

```
Ala Tyr Xaa Asn Ile His His Pro Ser Lys Leu Val Met Gly Ala Asp
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Asn Phe Xaa Lys Gly Lys Ser
    130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Ser Val Arg Ser Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp His Ser Asp
        195                 200                 205

Ser Val Gly Phe Ile Phe His Asp Asp Ala Lys Arg Leu Asp Arg Ser
    210                 215                 220

Ala Lys Asn Arg Tyr Thr Val
225                 230
```

POTYVIRUS RESISTANCE IN POTATO

CROSS-REFERENCE TO RELATED PATENT APPLICATIONS

This application claims priority to U.S. Provisional Application No. 61/394,081 filed on Oct. 18, 2010 and U.S. Provisional Application No. 61/482,579 filed on May 4, 2011, all of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Dec. 9, 2011, is named 58951398.txt and is 116,499 bytes in size.

FIELD OF THE INVENTION

The present invention is in the field of agrogenomics and plant genetic modification to produce plants with altered traits, such as PVY resistance, or improved PVY resistance compared to non-modified or untransformed plants.

BACKGROUND

Potyvirus infection of potato plants results in a variety of symptoms depending on the viral strain. These symptoms include production loss, leaf curling, mild mottling, rapid death of the infected area and area surrounding the infection, distorted and brittle leaves, wrinkled and rough leaves and the potato tuber necrotic ringspot disease. Necrotic ringspots render potatoes unmarketable and can therefore result in a significant loss of income. Potyviruses are transmissible by aphid vectors but may also remain dormant in seed potatoes. This means that using the same line of potato for production of seed potatoes for several consecutive generations will lead to a progressive increase in viral load and subsequent loss of crop.

Recessive resistance against specific potyvirus strains can be associated with one or several amino acid substitutions of the eIF4E protein in tomato, pepper, melon, barley, lettuce, and pea (FIG. 1). Although these substitutions appear clustered, it has proven difficult to design new versions of eIF4E mediating disease resistance.

eIF4E gene-mediated resistance is recessive, but it has been shown that the pepper gene pvr1 provides dominant potyvirus resistance when overexpressed in tomato (Kang et al., Plant Biotechnol J 5: 526-536).

It is impossible to develop potyvirus resistance in tetraploid potato by using TILLING (Piron et al., PLoS ONE 5, 2010). This method requires the use of inbred lines (which cannot be produced in tetraploid potato) and backcrossing (to segregate the trait with undesirable mutations induced by whole-genome mutagenesis treatments). Because potato is highly heterozygote and suffers from inbreeding depression, backcrossing results in reduced fitness and may trigger seedling death.

Nothing is known yet about the molecular basis of potyvirus resistance in potato and its sexually-compatible "wild potato" relatives. This lack of knowledge made it impossible to incorporate resistance into existing varieties through all-native DNA transformation, a new approach to genetic engineering that is perceived as more acceptable by consumers.

The potato eIF4E protein has a 46-amino acid domain with the consensus sequence $DX_1X_2X_3X_4K$ $SX_5Q$ $X_6AW$ GSS $X_7RX_8$ $X_9YT$ $FSX_{10}$ $VEX_{11}$ $FWX_{12}X_{13}YN$ NIH $X_{14}P$ S $KLX_{15}X_{16}GA$ D (SEQ ID NO: 38), whereby either at least one of the neutral amino acids ("X") is substituted by a charged amino acid or at least one of the charged amino acids is substituted by a neutral amino acid or an amino acid having an opposite charge. See U.S. Pat. No. 7,919,677. It is also confirmed that replacement of (i) the neutral amino acid $X_3$ by the negative amino acid glutamate (E), or (ii) the neutral amino acid $X_7$ by the positive amino acid arginine (R) may yield potyvirus resistance. See U.S. Pat. No. 7,772,462 B2. These studies also indicated that resistance may be obtained by replacing amino acid at position 8 by an arginine.

Potato is sexually compatible with hundreds of wild potato species, which means that it is part of an unusually large and diverse gene pool. However, despite this remarkable competitive advantage, none of the currently available potato varieties displays resistance against the agronomically-important potyvirus pathogen potato virus Y (PVY).

SUMMARY

One aspect of the present technology is a method for conferring PVY resistance to a plant for at least a period of time, comprising:

(A) expressing at least one of (i) the full-length pwp1 gene comprising the sequence of SEQ ID NO: 2, or (ii) the full-length pwp2 gene comprising the sequence of SEQ ID NO: 4 in a cell of a plant; or (B) expressing at least one of (i) a full-length pwp1 gene comprising the sequence of SEQ ID NO: 2, or (ii) the full-length pwp2 gene comprising the sequence of SEQ ID NO: 4, in a cell of a plant and also downregulating the expression of the plant's endogenous eIF4E gene; or (C) expressing at least one of (i) an N-terminal-truncated fragment of SEQ ID NO:2 or (ii) an N-terminal-truncated fragment of SEQ ID NO: 4; or (D) mutating the sequence of the plant's endogenous eIF4E gene to comprise at least two point mutations from the group consisting of i) T44A, (ii) S68N, (iii) 170T, (iv) K72R, (v) T76I, (vi) A77D, (vii) V128I, (viii) A130S, (ix) S172N and (x) S175V of SEQ ID NO: 6, or (i) T10M, (ii) A23G, (iii) Y47F, (iv) N99Y, (v) L140P of SEQ ID NO: 6 that confer resistance to PVY for at least a period of time (mutated sequences disclosed as SEQ ID NOS 83 and 84, respectively);

wherein the plant is either fully resistant to PVY virus infection, or develops one or more symptoms of PVY disease after a period of time.

In one embodiment, the fragments are selected from the group consisting of: (i) SEQ ID NO: 20, (ii) SEQ ID NO: 21.

In another embodiment, the period of time is selected from the group consisting of (i) 1-3 days; (ii) 3-5 days; (iii) 5-7 days; (iv) 7-9 days; (v) 9-11 days; (vi) 11-13 days; (vii) 13-15 days; (viii) 2-3 weeks; (ix) 3-4 weeks; (x) 4-5 weeks; (xi) 5-7 weeks; (xii) 7-10 weeks; (xii) 2-3 months and (xiii) 3-5 months.

In another embodiment, the plant is selected from the group consisting of: (i) potato, (ii) tomato, (iii) lettuce and (iv) pepper.

In another embodiment, the plant possesses one or more additional traits selected from the group consisting of: (i) low reducing sugar, (ii) low free asparagines, (iii) low bruising, (iv) reduced cold-induced sweetening, (v) low acrylamide, (vi) resistance to *Phytophthora*, (vii) reduced starch phosphate level and (viii) increased antioxidant.

Another aspect of the present technology is a method of transforming a plant to be fully resistant to PVY virus disease, or to resist the onset of one or more symptoms of PVY disease for a period of time, comprising transforming the plant with a polynucleotide encoding a protein with a sequence selected from the group consisting of: (i) SEQ ID NO: 26, (ii) SEQ ID NO: 28 and (iii) an N-terminus truncated fragments of a sequence selected from the group consisting of SEQ ID NO: 27, SEQ ID NO: 29 and SEQ ID NO: 32.

In one embodiment, the period of time is selected from the group consisting of (i) 1-3 days; (ii) 3-5 days; (iii) 5-7 days; (iv) 7-9 days; (v) 9-11 days; (vi) 11-13 days; (vii) 13-15 days; (viii) 2-3 weeks; (ix) 3-4 weeks; (x) 4-5 weeks; (xi) 5-7 weeks; (xii) 7-10 weeks; (xii) 2-3 months and (xiii) 3-5 months.

In another embodiment, the fragments are selected from the group consisting of (i) SEQ ID NO: 16 and (ii) SEQ ID NO: 23.

In another embodiment, the plant is selected from the group consisting of: (i) potato, (ii) tomato, (iii) lettuce and (iv) pepper.

In another embodiment, the plant possesses one or more additional traits selected from the group consisting of: (i) low reducing sugar, (ii) low free asparagines, (iii) low bruising, (iv) reduced cold-induced sweetening, (v) low acrylamide, (vi) resistance to *Phytophthora*, (vii) reduced starch phosphate level and (viii) increased antioxidant.

In another embodiment, the plant's endogenous eIF4E gene id downregulated or inhibited. For instance, the amount of the RNA transcript of the native eIF4E gene or the protein product of the native eIF4E gene may be reduced by 10%, 20%, 30%, 40%, 50%, 60%, 70%, 80%, 90% or 100%.

In another embodiment, the transformed plant possesses one or more additional traits selected from the group consisting of: (i) low reducing sugar, (ii) low free asparagines, (iii) low bruising, (iv) reduced cold-induced sweetening, (v) low acrylamide, (vi) resistance to *Phytophthora*, (vii) reduced starch phosphate level and (viii) increased antioxidant.

Another aspect of the present technology is an isolated polynucleotide, comprising a sequence that (A) encodes a protein with at least 80% identity to at least 15 contiguous amino acids of the eIF4E protein sequence SEQ ID NO: 6 and comprises at least two amino acids substitutions selected from the group consisting of (i) T44A, (ii) S68N, (iii) 170T, (iv) K72R, (v) T76I, (vi) A77D, (vii) V128I, (viii) A130S, (ix) S172N and (x) S175V of SEQ ID NO: 6, or (i) T10M, (ii) A23G, (iii) Y47F, (iv) N99Y, (v) L140P of SEQ ID NO: 6 (mutated sequences disclosed as SEQ ID NOS 83 and 84, respectively); or (B) encodes the protein comprising the sequence of SEQ ID NO: 2 or SEQ ID NO: 4 (C) encodes an N-terminus truncated fragment of SEQ ID NO: 2 or SEQ ID NO: 4; or (D) encodes a protein comprising the sequence SEQ ID NO: 27 or SEQ ID NO: 28; or (E) encodes an N-terminus truncated fragment of a sequence of SEQ ID NO: 27, SEQ ID NO: 29 or SEQ ID NO: 32; wherein the polynucleotide confers full or partial resistance to PVY disease when it is expressed in the plant.

The S68N substitution is a neutral-to-neutral amino acid change at the position represented by $X_1$ of SEQ ID NO: 25 or 38. The present technology contemplates that S68 may be changed to other neutral amino acids, such as alanine and cysteine.

The S68N substitution is a neutral-to-neutral amino acid change at the position represented by $X_1$ of SEQ ID NO: 25 or 38. The present technology contemplates that S68 may be changed to other neutral amino acids, such as alanine and cysteine.

The I70T substitution is a neutral-to-neutral amino acid change at the position represented by $X_3$ of SEQ ID NO: 25 or 38. The present technology contemplates that 170 may be changed to other neutral amino acids, such as valine and leucine.

The K72R substitution is a neutral-to-neutral amino acid change at the position represented by position 6 of SEQ ID NO: 25 or 38. The present technology contemplates that K72 may be changed to other positive amino acids, such as histidine and lysine.

The A77D substitution is a neutral-to-negative amino acid change at the position represented by position 11 of SEQ ID NO: 25 or 38. The present technology contemplates that A77 may be changed to other negative amino acids, such as glutamic acid and aspartic acid.

In one embodiment, the polynucleotide encodes a protein that shares at least about 99%, 98%, 97%, 96%, 95%, 94%, 93%, 92%, 91%, 90%, 89%, 88%, 87%, 86%, 85%, 84%, 83%, 82%, 81% or 80% sequence identity with SEQ ID NOs: 2, 4 or 6, or with a partial sequence fragment of SEQ ID NOs: 2, 4 or 6. In this respect, a partial sequence fragment of SEQ ID NOs: 2, 4 or 6 means a peptide fragment that comprises more than 2 contiguous amino acids and which also functions to confer resistance to PVY virus upon a plant. Accordingly, in one embodiment, a partial sequence fragment of SEQ ID NOs: 2, 4 or 6 confers PVY resistance to a plant and comprises 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230 or 231 contiguous amino acids of SEQ ID NOs: 2, 4 or 6.

In another embodiment, the polynucleotide encodes an N-terminus truncated fragment of any sequence disclosed herein that confers PVY resistance to a plant, wherein the fragment comprises (i) residues 40-231 of SEQ ID NO: 2, 4, or 6, or (ii) residues 50-231 of SEQ ID NO: 2, 4, or 6, or (iii) residues 51-231 of SEQ ID NO: 2, 4, or 6, or (iv) residues 52-231 of SEQ ID NO: 2, 4, or 6, or (v) residues 53-231 of SEQ ID NO: 2, 4, or 6; or (vi) residues 54-231 of SEQ ID NO: 2, 4, or 6, or (vii) residues 55-231 of SEQ ID NO: 2, 4, or 6, or (viii) residues 60-231 of SEQ ID NO: 2, 4, or 6.

In another embodiment, a fragment of SEQ ID NO: 2 comprises one or more of the following combinations of amino acids: (N68, T70), (N68, R72), (N68, I76), (N68, D77), (N68, I128), (N68, S130), (N68, N172), (N68, V175), (T70, N68), (T70, R72), (T70, I76), (T70, D77), (T70, I128), (T70, S130), (T70, N172), (T70, V175), (R72, N68), (R72, T70), (R72, I76), (R72, D77), (R72, I128), (R72, S130), (R72, N172), (R72, V175), (I76, N68), (I76, T70), (I76, R72), (I76, D77), (I76, I128), (I76, S130), (I76, N172), (I76, V175), (D77, N68), (D77, T70), (D77, R72), (D77, I76), (D77, I128), (D77, S130), (D77, N172), (D77, V175), (I128, N68), (I128, T70), (I128, R72), (I128, I76), (I128, D77), (I128, S130), (I128, N172), (I128, V175), (S130, N68), (S130, T70), (S130, R72), (S130, I76), (S130, D77), (S130, I128), (S130, N172), (S130, V175), (N172, N68), (N172, T70), (N172, R72), (N172, I76), (N172, D77), (N172, I128), (N172, S130), (N172, V175), (V175, N68), (V175, T70), (V175, R72), (V175, I76), (V175, D77), (V175, I128), (V175, S130) and (V175, N172). This numbering scheme reflects the position of the denoted residue within SEQ ID NO: 2. Thus, “N68” refers to asparagine at position 68 of SEQ ID NO: 2; “T70” indicates residue threonine at position 70 of SEQ ID NO: 2, and so on. In one embodiment, a partial sequence fragment of SEQ ID NO: 2 is a fragment of SEQ ID NO: 2 that contains one or more of the following amino acids (i) N68, (ii) T70, (iii) R72, (iv) I76, (v) D77, (vi) I128, (vii) S130, (viii) N172 and (ix) V175, of SEQ ID NO:2.

In another embodiment, a fragment of SEQ ID NO: 4 comprises one or more of the following combinations of amino acids: (T10, A23), (T10, Y57), (T10, N99Y), (T10, S140), (A23,Y57), (A23, N99Y), (A23, S140), (Y57, N99Y), (Y57, S140), (N99Y, S140). This numbering scheme reflects the position of the denoted residue within SEQ ID NO: 4. Thus, “T10” refers to threonine at position 10 of SEQ ID NO: 4; “A23” indicates residue alanine at position 23 of SEQ ID NO: 4, and so on. In one embodiment, a partial sequence fragment of SEQ ID NO: 4 is a fragment of SEQ ID NO: 4 that contains one or more of the following amino acids (i) T10, (ii) A23, (iii) Y47, (iv) N99 and (v) S140 of SEQ ID NO: 4.

In another embodiment, a fragment of SEQ ID NO: 6 comprises one or more of the following combinations of amino acid substitutions of SEQ ID NO: 6: (S68N, I70T), (S68N, K72R), (S68N, T76I), (S68N, A77D), (S68N, V128I), (S68N, A130S), (S68N, S172N), (S68N, S175V), (I70T, S68N), (I70T, K72R), (I70T, T76I), (I70T, A77D), (I70T, V128I), (I70T, A130S), (I70T, S172N), (I70T, S175V), (K72R, S68N), (K72R, I70T), (K72R, T76I), (K72R, A77D), (K72R, V128I), (K72R, A130S), (K72R, S172N), (K72R, S175V), (T76I, S68N), (T76I, I70T), (T76I, K72R), (T76I, A77D), (T76I, V128I), (T76I, A130S), (T76I, S172N), (T76I, S175V), (A77D, S68N), (A77D, I70T), (A77D, K72R), (A77D, T76I), (A77D, V128I), (A77D, A130S), (A77D, S172N), (A77D, S175V), (V128I, S68N), (V128I, I70T), (V128I, K72R), (V128I, T76I), (V128I, A77D), (V128I, A130S), (V128I, S172N), (V128I, S175V), (A130S, S68N), (A130S, I70T), (A130S, K72R), (A130S, T76I), (A130S, A77D), (A130S, V128I), (A130S, S172N), (A130S, S175V), (S172N, S68N), (S172N, I70T), (S172N, K72R), (S172N, T76I), (S172N, A77D), (S172N, V128I), (S172N, A130S), (S172N, S175V), (S175V, S68N), (S175V, I70T), (S175V, K72R), (S175V, T76I), (S175V, A77D), (S175V, V128I), (S175V, A130S) and (S175V, S172N).

In another embodiment, a fragment of SEQ ID NO: 6 comprises one or more of the following combinations of amino acid substitutions of SEQ ID NO: 6: (T10M, A23G), (T10M, Y47F), (T10M, N99Y), (T10M, L140P), (A23G, Y47F), (A23G, N99Y), (A23G, L140P), (Y47F, N99Y), (Y47F, L140P) and (N99Y, L140P).

In one embodiment, the fragments are selected from the group consisting of (i) SEQ ID NO: 20, (ii) SEQ ID NO: 21, (iii) SEQ ID NO: 16 and (iv) SEQ ID NO: 23.

Another aspect of the present technology is a vector, comprising a polynucleotide which comprises a sequence that (A) encodes a protein with at least 80% identity to at least 15 contiguous amino acids of the eIF4E protein sequence SEQ ID NO: 6 and comprises at least two amino acids substitutions selected from the group consisting of (i) T44A, (ii) S68N, (iii) I70T, (iv) K72R, (v) T76I, (vi) A77D, (vii) V128I, (viii) A130S, (ix) S172N and (x) S175V of SEQ ID NO: 6, or (i) T10M, (ii) A23G, (iii) Y47F, (iv) N99Y, (v) L140P of SEQ ID NO: 6 (mutated sequences disclosed as SEQ ID NOS 83 and 84, respectively); or (B) encodes the protein comprising the sequence of SEQ ID NO: 2 or SEQ ID NO: 4 (C) encodes an N-terminus truncated fragment of SEQ ID NO: 2 or SEQ ID NO: 4; or (D) encodes a protein comprising the sequence SEQ ID NO: 27 or SEQ ID NO: 28; or (E) encodes an N-terminus truncated fragment of a sequence of SEQ ID NO: 27, SEQ ID NO: 29 or SEQ ID NO: 32; wherein the polynucleotide confers full or partial resistance to PVY disease when it is expressed in the plant.

In one embodiment, the polynucleotide is located in an *Agrobacterium* transfer-DNA.

In another embodiment, the *Agrobacterium* transfer-DNA comprises border-like sequences that are not 100% identical to any *Agrobacterium* T-DNA border sequences.

Another aspect of the present technology is a plant which comprises within its genome, or otherwise expresses, a polynucleotide which comprises a sequence that (A) encodes a protein with at least 80% identity to at least 15 contiguous amino acids of the eIF4E protein sequence SEQ ID NO: 6 and comprises at least two amino acids substitutions selected from the group consisting of (i) T44A, (ii) S68N, (iii) I70T, (iv) K72R, (v) T76I, (vi) A77D, (vii) V128I, (viii) A130S, (ix) S172N and (x) S175V of SEQ ID NO: 6, or (i) T10M, (ii) A23G, (iii) Y47F, (iv) N99Y, (v) L140P of SEQ ID NO: 6 (mutated sequences disclosed as SEQ ID NOS 83 and 84, respectively); or (B) encodes the protein comprising the sequence of SEQ ID NO: 2 or SEQ ID NO: 4 (C) encodes an N-terminus truncated fragment of SEQ ID NO: 2 or SEQ ID NO: 4; or (D) encodes a protein comprising the sequence SEQ ID NO: 27 or SEQ ID NO: 28; or (E) encodes an N-terminus truncated fragment of a sequence of SEQ ID NO: 27, SEQ ID NO: 29 or SEQ ID NO: 32; wherein the polynucleotide confers full or partial resistance to PVY disease when it is expressed in the plant In one embodiment, the plant is selected from the group consisting of: (i) potato, (ii) tomato, (iii) lettuce and (iv) pepper.

Another embodiment is a tuber, leaf or fruit grown from the plant.

In another embodiment, the plant possesses one or more additional traits selected from the group consisting of: (i) low reducing sugar, (ii) low free asparagines, (iii) low bruising, (iv) reduced cold-induced sweetening, (v) low acrylamide, (vi) resistance to *Phytophthora*, (vii) reduced starch phosphate level and (viii) increased antioxidant.

Another aspect of the present technology is a method of making a food product, comprising: (1) transforming a plant with the polynucleotide of claim 13; (2) growing the transformed plant and obtaining a tuber, fruit, or leaf from the plant; and (3) either (i) directly using the tuber, fruit, or leaf as a food product or (ii) processing the tuber, fruit, or leaf into a food product.

In one embodiment, the expression of the plant's endogenous eIF4E gene is downregulated or inhibited. For instance, the amount of the RNA transcript of the native eIF4E gene or the protein product of the native eIF4E gene may be reduced by 10%, 20%, 30%, 40%, 50%, 60%, 70%, 80%, 90% or 100%.

In another embodiment, substantially all cells of the transformed plant express the polynucleotide.

In another embodiment, at least 5 leaves of the transformed plant express the polynucleotide.

In another embodiment, at least 50% of the cells of the transformed plant express the polynucleotide.

In another embodiment, the polynucleotide is expressed for at least one week.

Another aspect of the present technology is a food product made from a method of making a food product, comprising: (1) transforming a plant with the polynucleotide of claim 13;

(2) growing the transformed plant and obtaining a tuber, fruit, or leaf from the plant; and (3) either (i) directly using the tuber, fruit, or leaf as a food product or (ii) processing the tuber, fruit, or leaf into a food product.

Another aspect of the present technology is a food product, comprising a plant cell obtained from a plant comprising within its genome, or otherwise expressing, a polynucleotide which comprises a sequence that (A) encodes a protein with at least 80% identity to at least 15 contiguous amino acids of the eIF4E protein sequence SEQ ID NO: 6 and comprises at least two amino acids substitutions selected from the group consisting of (i) T44A, (ii) S68N, (iii) I70T, (iv) K72R, (v) T76I, (vi) A77D, (vii) V128I, (viii) A130S, (ix) S172N and (x) S175V of SEQ ID NO: 6, or (i) T10M, (ii) A23G, (iii) Y47F, (iv) N99Y, (v) L140P of SEQ ID NO: 6 (mutated sequences disclosed as SEQ ID NOS 83 and 84, respectively); or (B) encodes the protein comprising the sequence of SEQ ID NO: 2 or SEQ ID NO: 4 (C) encodes an N-terminus truncated fragment of SEQ ID NO: 2 or SEQ ID NO: 4; or (D) encodes a protein comprising the sequence SEQ ID NO: 27 or SEQ ID NO: 28; or (E) encodes an N-terminus truncated fragment of a sequence of SEQ ID NO: 27, SEQ ID NO: 29 or SEQ ID NO: 32; wherein the polynucleotide confers full or partial resistance to PVY disease when it is expressed in the plant.

BRIEF DESCRIPTION OF THE DRAWINGS

FIG. 1: Alignment of eIF4E proteins (SEQ ID NOS 54-73, respectively, in order of appearance) associated with recessive resistance. Mutations observed in each resistant allele are underlined.

FIG. 2: Alignment of the proteins (SEQ ID NOS 74-77, respectively, in order of appearance) encoded by eIF4E from potato (*S. tuberosum*) and segregating individuals from accessions of the wild potato species *S. etuberosum, S. chacoense*, and *S. demissum*. Pwp1 was isolated from *S. etuberosum* accession PI245939, *S. chacoense* accessions PI175446 and PI175419, and *S. demissum* accession PI175423. Pwp2 was isolated from *S. stoloniferum* accessions PI195195 and PI275244. Polymorphisms between two wild type alleles are underlined and mutations on wild potato allele were also underlined.

FIG. 3: Alignment of pwp1 and pwp2 with previously characterized eIF4E proteins associated with recessive resistance (SEQ ID NOS 78-79, 54-64, 66-72, and 80, respectively, in order of appearance). Mutations on pwp1 and pwp2 are underlined.

FIG. 9: RNA gel blot analysis of selected pSIM1588 (modified pepper eIF4E 1, mpe1, overexpression) plants. RNA was isolated from leaf tissues of wild type Burbank (wt), empty vector control (401) and transgenic pSIM1588 (2, 5, 7, 9, 12, 13, 18, 19, 20 and 23) plants, run on the gel, transferred to nylon membrane and hybridized with Dig-labeled pepper eIF4E probe according to standard protocol. EB-stained ribosome RNA was used as loading control. Lines 7, 9, 13, 19 and 20 are resistant to PVY two weeks after infection, and lines 9 and 13 are resistant to PVY four weeks after infection. Lines 2, 5, 12, 18, 23 are susceptible.

FIG. 10: RNA gel blot analysis of selected pSIM1723 (modified pepper eIF4E 2, mpe2, overexpression) plants. RNA was isolated from leaf tissues of wild type Burbank (wt), empty vector control (401) and transgenic pSIM1723 (6, 7, 9, 10, 15, 19, 20 and 22) plants, run on the gel, transferred to nylon membrane and hybridized with Dig-labeled pepper eIF4E probe according to standard protocol. EB-stained ribosome RNA was used as loading control. Lines 9 and 20 are resistant to PVY two weeks after infection, line 20 is resistant to PVY four weeks after infection and lines 6, 7, 10, 15, 19 and 22 are susceptible.

DETAILED DESCRIPTION

Figure 4:
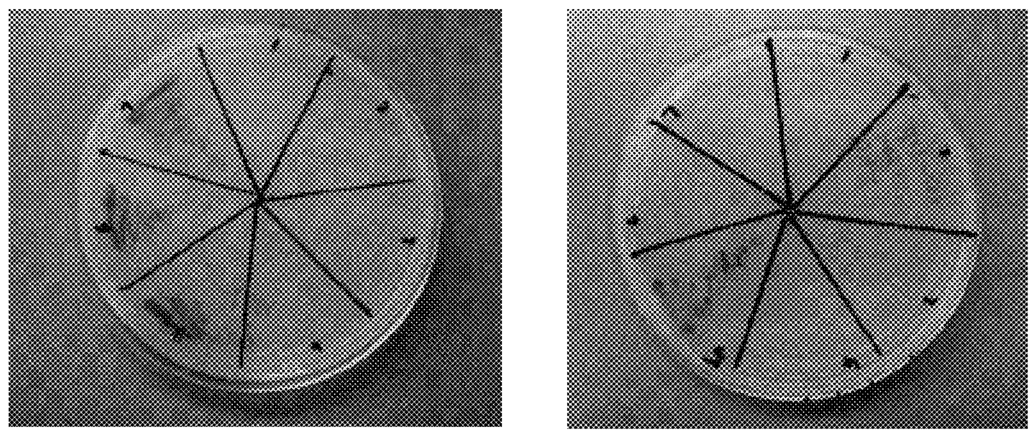
FIG. 4: The vpg binding ability of pwp1, pwp2 and SteIF4EA77D proteins in the yeast two hybrid system. (Top panels) pwp1 and pwp2 binding ability: (Left) Yeast transformants on SD (-Leu, -Trp) plate. (Right) Yeast transformants on SD (-Leu, -Trp, -His) plate. Bait plasmid PBD was used to express vpg from PVY strain NTN. Prey plasmid PAD was used to express wild type potato EIF4E and wild potato pwp1 and pwp2. 1-4: Single vector transformants (1, PBD-vpg; 2, PAD-wt EIF4E; 3, PAD-pwp1; 4, PAD-pwp2). 5-6: double-vector co-transformants (5, PBD-vpg+PAD-wt EIF4E; 6, PBD-vpg+PAD-pwp1; 7, PBD-vpg+PAD-pwp2). Colonies from each co-transformation grow on -leucine, -typtophone medium indicated existence of both constructs. Only PBD-VPg/PAD-WTEIF4E co-transformants grow on -leucine, -trptophone, -histidine plates indicated only wtEIF4E but not pwp1 and pwp2 interacts with VPg. (Bottom panel) SteIF4EA77D binding ability. Two independent yeast transformants were streaked on SD (-Leu, -Trp, -His) plate. 1 and 4 (PAD::SteIF4EA77D and PBD::VPg), 2 and 5 (PAD::SteIF4E and PBD::VPg), 3 and 6 (PAD::SteIF4EA77D). PBD-VPg/PAD-SteIF4EA77D co-transformants grow on -leucine, -trptophone, -histidine plates indicated only A77D mutation did not abolish the VPg binding ability of SteIF4E protein.

Unless defined otherwise, all technical and scientific terms used herein have the same meaning as commonly understood by one of ordinary skill in the art to which this invention belongs. Generally, the nomenclature used herein, and the laboratory procedures in cell culture, molecular genetics, and nucleic acid chemistry and hybridization described herein, are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology disclosed, for example, in "Molecular cloning a laboratory manual", 2d ed., Cold Spring Harbor Laboratory Press, Cold Spring Harbor, N.Y. (1989), and Current protocols in molecular biology, John Wiley & Sons, Baltimore, Md. (1989).

"*Agrobacterium*" means any Agrobacteria that are used for transforming plant cells, are disarmed and virulent derivatives of, usually, *Agrobacterium tumefaciens* or *Agrobacterium rhizogenes* that contain a vector. The vector typically contains a desired polynucleotide that is located between the borders of a T-DNA or, according to the present invention, between the border-like sequences of a "plant-DNA" ("P-DNA"), see definition below, which border (like) sequences are capable of transferring the desired polynucleotide into a plant genome. Examples of Agrobacteria include but are not limited to *Agrobacterium* sp., *Rhizobium* sp., *Phyllobacterium* sp., *SinoRhizobium* sp., and *MesoRhizobium* sp.

"Amino acid sequence" includes an oligopeptide, peptide, polypeptide, or protein and fragments thereof, that are isolated from, native to, or naturally occurring in a plant, or are synthetically made but comprise the nucleic acid sequence of the endogenous counterpart.

"Artificially manipulated" means to move, arrange, operate or control by the hands or by mechanical means or recombinant means, such as by genetic engineering techniques, a plant or plant cell, so as to produce a plant or plant cell that has a different biological, biochemical, morphological, or physiological phenotype and/or genotype in comparison to unmanipulated, naturally-occurring counterpart.

"Asexual propagation" means producing progeny by generating an entire plant from leaf cuttings, stem cuttings, root cuttings, tuber eyes, stolons, single plant cells protoplasts, callus and the like, that does not involve fusion of gametes.

"Backbone" means the nucleic acid sequence of a vector or plasmid outside of a particular cassette or expression cassette or construct that is to be integrated into a plant genome. For example, in the case of an *Agrobacterium* transfer plasmid, the backbone is the entirety of the plasmid that excludes the particular T-DNA or P-DNA sequence within which is positioned the desired nucleic acid for introduction and/or integration into the plant genome. Accordingly, the backbone of such a plasmid may contain other expression cassettes, such as those for expressing a selectable marker, but which are not intended to be transferred into the plant genome. Such cassettes and constructs which are not intended to be transferred into the plant genome may therefore be considered to constitute part of the plasmid or vector "backbone."

"Bacterium-mediated plant transformation" means the modification of a plant by infecting either that plant or an explant or cell derived from that plant with a bacterium selected of the group consisting of *Agrobacterium* sp., *Rhizobium* sp., *Phyllobacterium* sp., *SinoRhizobium* sp., and *MesoRhizobium* sp. to transfer at least part of a plasmid that replicates in that bacterium to the nuclei of individual plant cells for subsequent stable integration into the genome of that plant cell.

"Binary plasmid" or "Binary construct" means a plasmid that can be maintained in both *E. coli* and *A. tumefaciens*, and contains T-DNA right and left borders that are flanked by at least 10 base pairs of DNA that flank these elements in *Agrobacterium* Ti or Ri plasmids. "Border and Border-like sequences" are *Agrobacterium*-derived, or plant-derived sequences, that facilitate cleavage of a transformation vector T-DNA or P-DNA. Typically, a left border sequence and a right border sequence flank a T-DNA or P-DNA and they both function as recognition sites for virD2-catalyzed nicking reactions. Such activity releases nucleic acid that is positioned between such borders. See Table 1 below for examples of border sequences.

TABLE 1

| "Border" and Border-Like sequences | |
|---|---|
| *Agrobacterium* T-DNA borders | |
| TGACAGGATATATTGGCGGGTAAAC (SEQ ID NO. 39) | *Agrobacterium* nopaline strains (RB) |
| TGGCAGGATATATTGTGGTGTAAAC (SEQ ID NO. 40) | *Agrobacterium* nopaline strains (LB) |
| TGGCAGGATATATACCGTTGTAATT (SEQ ID NO. 41) | *Agrobacterium* octopine strains (RB) |
| CGGCAGGATATATTCAATTGTAATT (SEQ ID NO. 42) | *Agrobacterium* octopine strains (LB) |
| TGGTAGGATATATACCGTTGTAATT (SEQ ID NO. 43) | LB mutant |
| TGGCAGGATATATGGTACTGTAATT (SEQ ID NO. 44) | LB mutant |
| YGRYAGGATATATWSNVBKGTAAWY (SEQ ID NO. 45) | Border motif |
| Border-like sequences | |
| CGGCAGGATATATCCTGATGTAAAT (SEQ ID NO. 46) | *R. leguminosarum* |
| TGGCAGGAGTTATTCGAGGGTAAAC (SEQ ID NO. 47) | *T. tengcongensis* |
| TGACAGGATATATCGTGATGTCAAC (SEQ ID NO. 48) | *Arabidopsis thaliana* |
| GGGAAGTACATATTGGCGGGTAAAC (SEQ ID NO. 49) | *A. thaliana* CHR1v07142002 |
| TTACAGGATATATTAATATGTATGA (SEQ ID NO. 50) | *Oryza sativa* AC078894 |
| TAACATGATATATTCCCTTGTAAAT (SEQ ID NO. 51) | *Homo sapiens* clone HQ0089 |

TABLE 1-continued

| "Border" and Border-Like sequences | |
|---|---|
| TGACAGGATATATGGTAATGTAAAC (SEQ ID NO. 52) | potato (left border sequence)* |
| TGGCAGGATATATACCGATGTAAAC (SEQ ID NO. 53) | potato (right border sequence)* |

Y = C or T; R = A or G; K = G or T; M = A or C; W = A or T; S = C or G; V = A, C, or G; B = C, G, or T.
The accession numbers for the border-like sequences are: *Oryza sativa* chromosome 10 BAC OSJNBa0096G08 genomic sequence (AC078894.11); *Arabidopsis thaliana* chromosome 3 (NM_114337.1); *Arabidopsis thaliana* chromosome 1 (NM_105664.1); *T. tengcongensis* strain MB4T, section 118 of 244 of the complete genome (AE013091.1); *Homo sapiens* clone HQ0089 (AF090888.1); *Rhizobium* Clone: rhiz98e12.q1k.
*potato left and right border sequences were obtained and isolated according to the presently-described inventive methods.

The released nucleic acid, complexed with virD2 and virE2, is targeted to plant cell nuclei where the nucleic acid is often integrated into the genome of the plant cell. Usually, two border sequences, a left-border and a right-border, are used to integrate a nucleotide sequence that is located between them into another nucleotide sequence. It is also possible to use only one border, or more than two borders, to accomplish integration of a desired nucleic acid in such fashion.

A "native P-DNA border sequence" is about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51% or 50% similar in nucleotide sequence, but not identical to, to an *Agrobacterium* T-DNA border sequence. A border-like sequence can, therefore, be isolated from a plant genome and be modified or mutated to change the efficiency by which they are capable of integrating a nucleotide sequence into another nucleotide sequence. Other polynucleotide sequences may be added to or incorporated within a border-like sequence of the present invention. Thus, a P-DNA left border or a P-DNA right border may be modified so as to possess 5'- and 3'-multiple cloning sites, or additional restriction sites. A P-DNA border sequence may be modified to increase the likelihood that backbone DNA from the accompanying vector is not integrated into the plant genome.

A "border-like sequence" is isolated from the selected plant species that is to be modified, or from a plant that is sexually-compatible with the plant species to be modified, and functions like the border sequences of *Agrobacterium*. That is, a border-like sequence of the present invention promotes and facilitates the integration of a polynucleotide to which it is linked. A plant-DNA, i.e., P-DNA, of the present invention preferably contains border-like sequences. A border-like sequence may comprise the 5'-YGRYAGGATATATWSNVBKGTAAWY-3' (SEQ ID NO: 34) consensus sequence as described in U.S. Pat. No. 7,619,138, wherein Y is C or T; R is A or G; K is G or T; M is A or C; W is A or T; S is C or G; V is A, C, or G; and B is C, G, or T. A border-like sequence from potato (SEQ ID NO: 33) is described, for instance, in U.S. Pat. No. 7,880,057.

A border-like sequence of a P-DNA is between 5-100 bp in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length.

"Cassette" is a DNA sequence that may comprise various genetic elements. Accordingly, any one of the expression cassettes described herein may be inserted into a transfer-DNA that is delimited by such P-DNA border sequences, which are capable of integrating the cassette into another nucleic acid, such as a plant genome or plant chromosome. Accordingly, an *Agrobacterium* plasmid, which contains an expression cassette described herein that does not comprise a DNA region that is involved in 3-end formation and polyadenylation of an RNA transcript, may be stably integrated into the genome of a plant via *Agrobacterium*-mediated transformation. The progeny of that transformed plant, therefore, will continue to express the transcripts associated with the expression cassette.

"Callus formation": typically, young roots, stems, buds, and germinating seedlings are a few of the sources of plant tissue that can be used to induce callus formation. Callus formation is controlled by growth regulating substances present in tissue culture medium, such as auxins and cytokinins. The specific substances, and concentrations of those substances, that induce callus formation varies between plant species. Occasionally, different sources of explants require different culturing conditions, even if obtained from the same plant or species. Accordingly, a cocktail of various growth substances can be added to tissue culture medium in order to induce callus formation from a variety of plant species that are incubated on such media. Other factors, such as the amount of light, temperature, and humidity, for instance, are important in establishing a callus. Once established, callus cultures can be used to obtain protoplasts, or study somatic embryogenesis, organogenesis, and secondary metabolite production.

"Cleavage site" is a DNA sequence that is structurally different but functionally similar to T-DNA borders. A cleavage site comprises a sequence that is nicked when exposed to an enzyme involved in bacterium-mediated plant transformation. It can represent a synthetic sequence that may not be present in the genome of a living organism or it can represent a sequence from a living organism such as a plant, animal, fungus, or bacterium.

"Confer" means to invest with a property or characteristic, such as, in the present technology, to impart or give a particular trait or characteristic or property to a plant or plant cell. Thus, a particular resistance gene may confer viral resistance to a plant that is exposed to the particular virus. The resistance gene may also confer the ability of a plant cell to express an RNA transcript or protein, which by itself or in aggregate with transcripts and resistance proteins expressed from other cells, makes the plant, a part of the plant, or progeny of the plant, resistant to the virus. Accordingly, in the context of genetically engineered plants, a gene or polynucleotide that is integrated into the plant genome, or which is expressed in the plant cell but not integrated, may be said to "confer" resistance upon the plant or a part thereof to exposure to one or more viruses. To confer resistance, the gene may be expressed stably or transiently. According to the present invention, resistance to PVY may be conferred to a transformed plant over a period of time. For instance, a transformed cultivated plant of the present invention may be resistant to PVY virus for 1-5 days, 1 week, 2-4 weeks, 1 month, 2-12 months, 1 year, 2-5 years, 5-10 years, 10-50 years or 50-100 years, or longer.

The term "constitutive" when used in conjunction with a promoter means that the promoter dictates constant active expression of the gene controlled by the promoter. The term "near-constitutive", when used in conjunction with a promoter, means that the promoter does not have the same activities across different tissue types. Two examples of near-constitutive in plants are 35S promoter and Pat promoter.

A "cultivated" plant is one grown or tended to by, or under the control of, human care, attention, and husbandry. With respect to potato plants, *Solanum tuberosum* ssp. *tuberosum* is an example of one of the most widely cultivated potato varieties, although there are thousands of potato varieties worldwide. Modern varieties of *Solanum tuberosum* are the most widely cultivated. There are two major subspecies of *Solanum tuberosum: andigena*, or Andean; and *tuberosum*, or Chilean. In general, well-known cultivated varieties include, but are not limited to, russets, reds, whites, yellows (also called Yukons) and purples. Popular varieties, also known as cultivars, include: Adirondack Blue, Adirondack Red, Agata, Almond, Amandine, Anya, Arran Victory, Atlantic, Bamberg, Belle de Fontenay, BF-15, Bildtstar, Bintje, Blue Congo, Bonnotte, Cabritas, Camota, Chelina, Chiloé, Cielo, Clavela Blanca, Désirée, Fianna, Fingerling, Flava, Golden Wonder, Innovator, Jersey Royal, Kerr's Pink, Kestrel, King Edward, Kipfler, Lady Balfour, Linda, Marfona, Maris Piper, Marquis, Nicola, Pachacoñ a, Pink Eye, Pink Fir Apple, Primura, Ratte, Red Norland, Red Pontiac, Rooster, Russet Burbank, Russet Norkotah, Selma, Shepody, Sieglinde, Sirco, Spunta, Stobrawa, Vivaldi, Vitelotte, Yellow Finn, and Yukon Gold. Any of these cultivated varieties may be modified as disclosed herein to express a pwp1 gene for conferring resistance upon the variety to PVY virus. A wild potato plant is not a cultivated potato plant variety. See the definition elsewhere herein for more details.

The term "delayed disease progression" or "delayed disease symptoms" or "to resist the onset of one or more symptoms of PVY disease," or "partial resistance" in the context of the present invention means that, after being infected with the PVY virus, one or more symptoms of PVY disease do not appear for a period of time in a plant transformed as disclosed herein to express a PVY-resistance polynucleotide. For example, the transformed plant may display the disease symptom 1-3 days, 3-5 days, 5-7 days, 7-9 days, 9-11 days, 11-13 days, 13-15 days, 2-3 weeks, 3-4 weeks, 4-5 weeks, 5-7 weeks, 7-10 weeks, 2-3 months and 3-5 months later than the untransformed plant. Transformed plants with delayed disease progression typically carry the PVY virus protein upon infection. See Example 5. The PVY virus protein can be detected via ELISA assay. The length of the symptom delay varies.

PVY disease "symptoms" means a variety of reactions by the plant that may occur upon a PVY virus infection. These "symptoms" include, but are not limited to, rapid death of the infected area and area surrounding the infection, distorted and brittle leaves, wrinkled and rough leaves, leaf curling, mild mottling, some production reduction and the potato tuber necrotic ringspot disease. The present invention contemplates a delay in the appearance or onset of any of these symptoms and the phrases described above, e.g., "delayed disease progression," "delayed disease symptoms," "to resist the onset of one or more symptoms of PVY disease," and "partial resistance," are meant to connote that delay in PVY symptom appearance.

To "downregulate" or "inhibit" refers to a process by which the quantity of a cellular component, such as RNA or protein, is decreased in response to an external variable. Thus, for instance, in the context of gene silencing, it is possible to use sense, antisense, co-suppression, double-stranded RNA, hairpin RNA, siRNA, or to rely upon other gene silencing mechanisms, such as RNAi, to downregulate, inhibit, or silence the expression of an endogenous gene. This may mean that a consequence of gene silencing is the reduction in levels of RNA transcripts normally expressed from the targeted gene, or it may mean there is a reduction in the encoded and translated protein levels compared a non-silenced plant cell.

A "gene" is a segment of a DNA molecule that contains all the information required for synthesis of a product, polypeptide chain or RNA molecule that includes both coding and non-coding sequences. For instance, a gene may comprise different genetic elements such as discreet nucleotide sequences that include but are not limited to a promoter, terminator, intron, enhancer, spacer, 5'-untranslated region, 3'-untranslated region, or recombinase recognition site.

To "genetically modify" an organism can mean introducing a nucleic acid into a cell or genome of a plant or organism. The introduced nucleic acid may be DNA or RNA. The DNA or RNA may be single-stranded or double-stranded. The introduced nucleic acid may be stably integrated into a genome or chromosomal material, or may exist within the cell extrachromosomally.

"Isolated" refers to any nucleic acid or compound that is physically separated from its normal, native environment, and is therefore markedly different from its endogenous counterpart. The isolated material may be maintained in a suitable solution containing, for instance, a solvent, a buffer, an ion, or other component, and may be in purified, or unpurified, form.

"Native," when used to describe a gene or a genetic element, means that the gene or genetic element naturally exists in, originates from, or belongs to the genome of a plant that is to be transformed. In the same vein, the term "endogenous" also can be used to identify a particular nucleic acid, e.g., DNA or RNA, or a protein as "native" to a plant. Endogenous means an element that originates within the organism. Thus, any nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species. In other words, a native genetic element represents all genetic material that is accessible to plant breeders for the improvement of plants through classical plant breeding. Any variants of a native nucleic acid also are considered "native" in accordance with the present invention. In this respect, a "native" nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence.

A "native" nucleic acid isolated from a plant may also encode a variant of the naturally occurring protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60% similar in amino acid sequence to the unmodified, native protein expressed in the plant from which the nucleic acid was isolated.

"Naturally occurring nucleic acid" means that the nucleic acid is found within the genome of a selected plant species and may be a DNA molecule or an RNA molecule. The sequence of a restriction site that is normally present in the genome of a plant species can be engineered into an exogenous DNA molecule, such as a vector or oligonucleotide, even though that restriction site was not physically isolated from that genome. Thus, the present invention permits the synthetic creation of a nucleotide sequence, such as a restriction enzyme recognition sequence, so long as that sequence is naturally occurring in the genome of the selected plant species or in a plant that is sexually compatible with the selected plant species that is to be transformed.

Public concerns were addressed through development of an all-native approach to making genetically engineered plants, as disclosed by Rommens et al. in New Zealand Patent 535,395, U.S. Pat. No. 7,250,554, U.S. Pat. No. 7,534,934, and WO2005/004585, which are all incorporated herein by reference. Rommens et al. teach the identification and isolation of genetic elements from plants that can be used for bacterium-mediated plant transformation. Thus, Rommens teaches that a plant-derived transfer-DNA ("P-DNA"), for instance, can be isolated from a plant genome and used in place of an *Agrobacterium* T-DNA to genetically engineer plants.

"N-terminus" means the start of a protein or polypeptide terminated by an amino acid with a free amine group (—$NH_2$). Each amino acid has a carboxyl group and an amine group, and amino acids link to one another to form a chain by a dehydration reaction by joining the amine group of one amino acid to the carboxyl group of the next. Thus polypeptide chains have an end with an unbound carboxyl group, the C-terminus, and an end with an amine group, the N-terminus. The convention for writing peptide sequences is to put the N-terminus on the left and write the sequence from N- to C-terminus. When the protein is translated from messenger RNA, it is created from N-terminus to C-terminus. "N-terminus truncated" means that up to 99% of amino acids of a protein are missing from the N-terminus end of the protein. For example, for a 100-amino-acid long full length protein, the N-terminus truncated version of this protein may be missing the first amino acid at the N-terminus, the first to the fifth amino acid at the N-terminus, the first to the tenth amino acid at the N-terminus, the first to the twentieth amino acid at the N-terminus, the first to the thirtieth amino acid at the N-terminus, the first to the fortieth amino acid at the N-terminus, the first to the fiftieth amino acid at the N-terminus, the first to the sixtieth amino acid at the N-terminus, the first to the seventies amino acid at the N-terminus, the first to the eightieth amino acid at the N-terminus, the first to the ninetieth amino acid at the N-terminus or the first to the ninety ninth amino acid at the N-terminus. More specifically, The N-terminus truncated pwp1 may be missing the first amino acid at the N-terminus, the first one to twenty amino acids, the first one through forty amino acids, the first one through sixty amino acids, the first one through eighty amino acids, the first one through one hundred amino acids, the first one through one hundred fifty amino acids, the first one through two hundred amino acids, the first one through two hundred thirty amino acids. The N-terminus truncated pwp2 may be missing the first amino acid at the N-terminus, the first one to twenty amino acids, the first one through forty amino acids, the first one through sixty amino acids, the first one through eighty amino acids, the first one through one hundred amino acids, the first one through one hundred fifty amino acids, the first one through two hundred amino acids, the first one through two hundred thirty amino acids. More specifically, pwp1 or pwp2 may be missing the first one through fifty two amino acids as shown in SEQ ID NO: 20 and SEQ ID NO: 21 in Example 9.

A "plant" of the present invention includes, but is not limited to angiosperms and gymnosperms such as potato, tomato, tobacco, avocado, alfalfa, lettuce, carrot, strawberry, sugarbeet, cassava, sweet potato, soybean, pea, bean, cucumber, grape, brassica, maize, turf grass, wheat, rice, barley, sorghum, oat, oak, eucalyptus, walnut, and palm. Thus, a plant may be a monocot or a dicot. "Plant" and "plant material," as used interchangeably herein, also encompasses plant cells, seed, plant progeny, propagule whether generated sexually or asexually, and descendents of any of these, such as cuttings or seed. "Plant material" may refer to plant cells, cell suspension cultures, callus, embryos, meristematic regions, callus tissue, leaves, roots, shoots, gametophytes, sporophytes, pollen, seeds, germinating seedlings, and microspores. Plants may be at various stages of maturity and may be grown in liquid or solid culture, or in soil or suitable media in pots, greenhouses or fields. Expression of an introduced leader, trailer or gene sequences in plants may be transient or permanent.

"Regulatory sequences or elements" refers to those sequences which are standard and known to those in the art, that may be included in the expression vectors to increase and/or maximize transcription of a gene of interest or translation of the resulting RNA in a plant system. These include, but are not limited to, promoters, peptide export signal sequences, introns, polyadenylation, and transcription termination sites. Methods of modifying nucleic acid constructs to increase expression levels in plants are also generally known in the art (see, e.g. Rogers et al., 260 J. Biol. Chem. 3731-38, 1985; Cornejo et al., 23 Plant Mol. Biol. 567: 81, 1993). In engineering a plant system to affect the rate of transcription of a protein, various factors known in the art, including regulatory sequences such as positively or negatively acting sequences, enhancers and silencers, as well as chromatin structure may have an impact. The present invention provides that at least one of these factors may be utilized in engineering plants to express a protein of interest. The regulatory sequences of the present invention are native genetic elements, i.e., are isolated from the selected plant species to be modified. The promoters that are used to initiate transcription of the desired polynucleotide may be constitutive, tissue-preferred, or inducible promoters or permutations thereof. "Strong" promoters, for instance, include the potato ubiquitin-7 and ubiquitin-3 promoters, and ubiquitin promoters from maize, rice, and sugarcane. They also include the rice actin promoter, various rubisco small subunit promoters, rubisco activase promoters, and rice actin promoters. Good tissue-preferred promoters that are mainly expressed in potato tubers include the promoters of the granule-bound starch synthase and ADP glucose pyrophosphorylase genes. There are various inducible promoters, but typically an inducible promoter can be a temperature-sensitive promoter, a chemically-induced promoter, or a temporal promoter. Specifically, an inducible promoter can be a Ha hsp17.7 G4 promoter, a wheat wcs120 promoter, a Rab 16A gene promoter, an α-amylase gene promoter, a pin2 gene promoter, or a carboxylase promoter.

"Resistance" in the context of plant pathology means the power or capacity of a plant, explant or plant cell to withstand, endure, or survive the harmful effects or influences, such as disease, toxicity, and infection, by an harmful agent, such as a pathogen, insect, plant, bacteria, or virus. Resistance is a relative term that is often measured by how long the plant, explant, or plant cell, can tolerate harmful effects of the invading agent. For instance, the plant transformed with the present technology may exhibit disease symptoms for 1-7 days, 1-4 weeks, 1-12 months, 1-5 years, or for the entire lifetime of the plant later than a plant that has not been transformed to express one of the pwp1 or pwp2 polynucleotides disclosed herein.

The term "recessive" in the context of the present invention describes an allele that causes a phenotype (visible or detectable characteristic) that is only seen in a homozygous genotype (an organism that has two copies of the same allele) and never in a heterozygous genotype. In this regard, "recessive resistance" means that the resistance phenotype is only seen in homozygous genotype of the resistance allele.

"Sequence identity" or "identity" in the context of two nucleic acid or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11-17 (1988) e.g., as implemented in the program PC/GENE (Intelligenetics, Mountain View, Calif., USA).

"Percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Methods of alignment of sequences for comparison are well-known in the art. Optimal alignment of sequences for comparison may be conducted by the local homology algorithm of Smith and Waterman, Adv. Appl. Math. 2: 482 (1981); by the homology alignment algorithm of Needleman and Wunsch, J. Mol. Biol. 48: 443 (1970); by the search for similarity method of Pearson and Lipman, Proc. Natl. Acad. Sci. 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73: 237-244 (1988); Higgins and Sharp, CABIOS 5: 151-153 (1989); Corpet, et al., Nucleic Acids Research 16: 10881-90 (1988); Huang, et al., Computer Applications in the Biosciences 8: 155-65 (1992), and Pearson, et al., Methods in Molecular Biology 24: 307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul et al., J. Mol. Biol., 215:403-410 (1990); and, Altschul et al., Nucleic Acids Res. 25:3389-3402 (1997).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad Sci. USA 90:5873-5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters can be employed alone or in combination.

Multiple alignment of the sequences can be performed using the CLUSTAL method of alignment (Higgins and Sharp (1989) CABIOS. 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

A "trait" is a distinguishing feature or characteristic of a plant, which may be altered according to the present invention by integrating one or more "desired polynucleotides" and/or screenable/selectable markers into the genome of at least one plant cell of a transformed plant. The "desired polynucleotide(s)" and/or markers may confer a change in the trait of a transformed plant, by modifying any one of a number of genetic, molecular, biochemical, physiological, morphological, or agronomic characteristics or properties of the transformed plant cell or plant as a whole. Thus, expression of one or more, stably integrated desired polynucleotide(s) in a plant genome, may alter a trait that is selected from the group consisting of, but not limited to, increased drought tolerance, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved vigor, improved taste, improved texture, decreased phosphate content, increased germination, increased micronutrient uptake, improved starch composition, and improved flower longevity.

"Transformation" of a plant is a process by which DNA is stably integrated into the genome of a plant cell. "Stably" refers to the permanent, or non-transient retention and/or expression of a polynucleotide in and by a cell genome. Thus, a stably integrated polynucleotide is one that is a fixture within a transformed cell genome and can be replicated and propagated through successive progeny of the cell or resultant transformed plant. Transformation may occur under natural or artificial conditions using various methods well known in the art. See, for instance, METHODS IN PLANT MOLECULAR BIOLOGY AND BIOTECHNOLOGY, Bernard R. Glick and John E. Thompson (eds), CRC Press, Inc., London (1993); Chilton, Scientific American, 248) (6), pp. 36-45, 1983; Bevan, Nucl. Acids. Res., 12, pp. 8711-8721, 1984; and Van Montague et al., Proc R Soc Lond B Biol Sci., 210 (1180), pp. 351-65, 1980. Plants also may be transformed using "Refined Transformation" and "Precise Breeding" techniques. See, for instance, Rommens et al. in New Zealand Patent 535,395, U.S. Pat. No. 7,250,554, U.S. Pat. No. 7,534,934, WO2005/004585, U.S. Pat. No. 7,598,430, US-2005-0034188, WO2005/002994, and New Zealand Patent 536,037, which are all incorporated herein by reference.

Stably integrated DNA into the genome of a plant cell does not necessarily mean that the integrated DNA is continuously expressed in all parts of the plant. For instance, in one embodiment of the present technology the integrated DNA may be expressed in substantially all cells of the plant, or in 50%-99% of the cells of the plant. In another embodiment the integrated DNA may be expressed in one or more of the leaves, stem, flowers, reproductive organs, roots, and fruits and vegetables of the plant, such as in tubers of a transformed potato plant. As disclosed elsewhere herein a stably integrated polynucleotide may be expressed continuously or transiently over a period of time. For instance, a transformed cultivated plant of the present invention may be resistant to PVY virus for 1-5 days, 1 week, 2-4 weeks, 1 month, 2-12 months, 1 year, 2-5 years, 5-10 years, 10-50 years or 50-100 years.

"Transformation vector" is a plasmid that can be maintained in *Agrobacterium*, and contains at least one Right Border or initial cleavage site. Infection of explants with *Agrobacterium* strains carrying a transformation vector and application of transformation procedures will produce transformed calli, shoots, and/or plants that contain at least part of the transformation vector stably integrated into their genome. The vector may comprise a selectable marker to aid identification of plants that have been stably transformed.

A "transgenic plant" of the present invention is one that comprises at least one cell genome in which an exogenous nucleic acid has been stably integrated. According to the present invention, a transgenic plant is a plant that comprises only one genetically modified cell and cell genome, or is a plant that comprises some genetically modified cells, or is a plant in which all of the cells are genetically modified. A transgenic plant of the present invention may be one that comprises expression of the desired polynucleotide, i.e., the exogenous nucleic acid, in only certain parts of the plant. Thus, a transgenic plant may contain only genetically modified cells in certain parts of its structure.

A "tuber" is a thickened, usually underground, food-storing organ that lacks both a basal plate and tunic-like covering, which corms and bulbs have. Roots and shoots grow from growth buds, called "eyes," on the surface of the tuber. Some tubers, such as caladiums, diminish in size as the plants grow, and form new tubers at the eyes. Others, such as tuberous begonias, increase in size as they store nutrients during the growing season and develop new growth buds at the same time. Tubers may be shriveled and hard or slightly fleshy. They may be round, flat, odd-shaped, or rough. Examples of tubers include, but are not limited to ahipa, apio, arracacha, arrowhead, arrowroot, baddo, bitter casava, Brazilian arrowroot, cassava, Chinese artichoke, Chinese water chestnut, coco, cocoyam, dasheen, eddo, elephant's ear, girasole, goo, Japanese artichoke, Japanese potato, Jerusalem artichoke, jicama, lily root, ling gaw, mandioca, manioc, Mexican potato, Mexican yam bean, old cocoyam, potato, saa got, sato-imo, seegoo, sunchoke, sunroot, sweet casava, sweet potatoes, tanier, tannia, tannier, tapioca root, topinambour, water lily root, yam bean, yam, and yautia. Examples of potatoes include, but are not limited to Russet Potatoes, Round White Potatoes, Long White Potatoes, Round Red Potatoes, Yellow Flesh Potatoes, and Blue and Purple Potatoes.

Tubers may be classified as "microtubers," "minitubers," "near-mature" tubers, and "mature" tubers. Microtubers are tubers that are grown on tissue culture medium and are small in size. By "small" is meant about 0.1 cm-1 cm. A "minituber" is a tuber that is larger than a microtuber and is grown in soil. A "near-mature" tuber is derived from a plant that starts to senesce, and is about 9 weeks old if grown in a greenhouse. A "mature" tuber is one that is derived from a plant that has undergone senescence. A mature tuber is, for example, a tuber that is about 12 or more weeks old.

A plant-derived transfer-DNA ("P-DNA") border sequence of the present invention is not identical in nucleotide sequence to any known bacterium-derived T-DNA border sequence, but it functions for essentially the same purpose. That is, the P-DNA can be used to transfer and integrate one polynucleotide into another. A P-DNA can be inserted into a tumor-inducing plasmid, such as a Ti-plasmid from *Agrobacterium* in place of a conventional T-DNA, and maintained in a bacterium strain, just like conventional transformation plasmids. The P-DNA can be manipulated so as to contain a desired polynucleotide, which is destined for integration into a plant genome via bacteria-mediated plant transformation. See Rommens et al. in NEW ZEALAND PATENT 535,395, US-2003-0221213, U.S. Pat. No. 7,534,934, and WO2005/004585, which are all incorporated herein by reference.

Thus, a P-DNA border sequence is different by 1, 2, 3, 4, 5, 6, 7, 8, 9, 10, 11, 12, 13, 14, 15, 16, 17, 18, 19, 20, or more nucleotides from a known T-DNA border sequence from an *Agrobacterium* species, such as *Agrobacterium tumefaciens* or *Agrobacterium rhizogenes*.

A P-DNA border sequence is not greater than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51% or 50% similar in nucleotide sequence to an *Agrobacterium* T-DNA border sequence.

Methods were developed to identify and isolate transfer DNAs from plants, particularly potato and wheat, and made use of the border motif consensus described in U.S. Pat. No. 7,534,934, which is incorporated herein by reference.

In this respect, a plant-derived DNA of the present invention, such as any of the sequences, cleavage sites, regions, or elements disclosed herein is functional if it promotes the transfer and integration of a polynucleotide to which it is linked into another nucleic acid molecule, such as into a plant chromosome, at a transformation frequency of about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 15%, or about 5% or at least about 1%.

Any of such transformation-related sequences and elements can be modified or mutated to change transformation efficiency. Other polynucleotide sequences may be added to a transformation sequence of the present invention. For instance, it may be modified to possess 5'- and 3'-multiple cloning sites, or additional restriction sites. The sequence of a cleavage site as disclosed herein, for example, may be modified to increase the likelihood that backbone DNA from the accompanying vector is not integrated into a plant genome.

Any desired polynucleotide may be inserted between any cleavage or border sequences described herein. For example, a desired polynucleotide may be a wild-type or modified gene that is native to a plant species, or it may be a gene from a non-plant genome. For instance, when transforming a potato plant, an expression cassette can be made that comprises a potato-specific promoter that is operably linked to a desired potato gene or fragment thereof and a potato-specific terminator. The expression cassette may contain additional potato genetic elements such as a signal peptide sequence fused in frame to the 5'-end of the gene, and a potato transcriptional enhancer. The present invention is not limited to such an arrangement and a transformation cassette may be constructed such that the desired polynucleotide, while operably linked to a promoter, is not operably linked to a terminator sequence.

In addition to plant-derived elements, such elements can also be identified in, for instance, fungi and mammals. Several of these species have already been shown to be accessible to *Agrobacterium*-mediated transformation. See Kunik et al., Proc Natl Acad Sci USA 98: 1871-1876, 2001, and Casas-Flores et al., Methods Mol Biol 267: 315-325, 2004, which are incorporated herein by reference.

When a transformation-related sequence or element, such as those described herein, are identified and isolated from a plant, and if that sequence or element is subsequently used to transform a plant of the same species, that sequence or element can be described as "native" to the plant genome.

A "variant" is understood to mean a nucleotide or amino acid sequence that deviates from the standard, or given, nucleotide or amino acid sequence of a particular gene or protein. The terms, "isoform," "isotype," and "analog" also refer to "variant" forms of a nucleotide or an amino acid sequence. An amino acid sequence that is altered by the addition, removal or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software.

A "vector" which may also be regarded as a "plasmid" or "construct" is a vehicle used to transfer genetic material to a target cell. A vector may typically contain a desired polynucleotide, which shares sequence identity with at least part of a target gene that may be operably linked to a promoter and a terminator, or to two convergently-orient promoters, or in a expression cassette that lacks terminators. As is well appreciated, the promoter initiates transcription, while the terminator ends transcription at a specific site and subsequently mediates polyadenylation. Such transcript processing can be important for stability of the transcript and its transport from the nucleus and into the cytoplasm. On the other hand, another aspect of the present technology is a silencing construct that expresses a desired polynucleotide by two convergently-oriented promoters in the absence of any operably-linked terminators. These constructs produce unspecified RNA transcripts that are particularly effective in silencing an endogenous target gene. See, for instance, U.S. Pat. No. 7,713,735, which is incorporated herein by reference.

A vector of the present invention can be used to efficiently reduce or prevent the transcription or translation of a target nucleic acid by triggering convergent transcription of a desired polynucleotide. Hence one goal of the present invention is to provide constructs that produce nucleic acid molecules that prevent or reduce expression of a gene or of a gene product, such as an RNA transcript or protein.

A wild potato is related to, but is not, a cultivated potato, and belongs to the Solanaceae family. There are about 199 species of wild potato, and about 90% of them grow in Bolivia, Peru, Argentina, and Mexico. As used herein, a wild potato may also be regarded as an uncultivated or non-cultivated potato. Hence, wild, uncultivated, and non-cultivated are used interchangeably throughout the application to refer to the class of potatoes that do not belong to the cultivated class of potatoes, such as those used for commercial food, as disclosed elsewhere herein. Thus, a wild potato does not become classified as a "cultivated" potato merely because it has been grown somewhere other than where it is found naturally. That is, a wild potato species that has been transferred to a greenhouse or cultivatable field and thereafter grown under the direction and attention of man, does not, for the purposes of the present invention, become re-classified as a "cultivated" potato in that new environment. Examples of wild potato species include but are not limited to *Solanum* L. species, such as *Solanaceae* sect. *Petota* Dumort, and *Solanum* sect. *Etuberosum*. See Hijmans and Spooner, American Journal of Botany, 88 (11): 2101-2112 (2001), which is incorporated herein by reference. Particular examples of wild potato species include *Solanum etuberosum* (accession PI245939), *S. chacoense* (accessions PI175446 and PI175419), and *S. demissum* accession PI175423. Accordingly, the present invention encompasses the identification and isolation of viral resistant genes from one or more wild potato genomes, and the transformation of cultivated potato plants with one or more of those wild viral resistant genes, or fragments thereof.

Accordingly, as aspect of the present invention is the introduction of a wild homolog of one or more eIF4E genes into a plant, explant, or cell, in order to confer virus resistance to that plant, explant, or cell. For instance, one example of the plant is cultivated potato plant. One example of the wild homolog of eIF4E gene is pwp1. Pwp1 can be introduced into the genome of a plant to confer resistance, or the native eIF4E can be mutated to contain one or more pwp1-specific amino acids, in order to confer resistance. One example of a plant in this aspect of the present invention is a cultivated potato plant that exhibits resistance to PVY virus.

1. The Potato Virus Y

Potato virus Y (PVY, also called *Solanum* virus 2) is a plant pathogenic virus of the family Potyviridae, and one of the most important plant viruses affecting potato production. PVY may severely depress yields of cultivated potato and is spread by aphids in a nonpersistent manner and by human activity. This means that using the same line of potato for production of seed potatoes for several consecutive generations may lead to a progressive increase in viral load and subsequent loss of crop.

PVY infection of potato plants results in a variety of symptoms depending on the viral strain. The mildest of these symptoms is production loss, but the most detrimental is "potato tuber necrotic ringspot disease" (PTNRD). Necrotic ringspots render potatoes unmarketable and can therefore result in a significant loss of income. The increased rate of infection in recent years may be attributed to several factors. These include a marked decrease in the effectiveness and administration of chemicals used in vector control, the use of infected seed potatoes in cultivation, incorrect irrigation and farming methods as well as a lack of a sensitive, rapid and reliable method of detection.

There are about five-thousand cultivated potato varieties worldwide belonging to eight or nine species, and about 200 wild species and subspecies. None of the more commercially important cultivated potato varieties, however, exhibit resistance against the agronomically-devastating PVY virus. Furthermore, besides infecting potato, PVY affects other solanaceous crops (tomato, pepper) and weeds (nightshade, groundcherry). Accordingly, the present invention can be applied to a variety of plants, not only potato, such as to but not limited to tomato, pepper, nightshade, and groundcherry.

2. eIF4E eIF4E (eukaryotic translation initiation factor 4E) is a eukaryotic translation initiation factor involved in directing ribosomes to the cap structure of mRNAs to initiate translation. In performing its function, eIF4E binds to the mRNA cap structure (i.e., first nucleotide on the 5' end of an mRNA molecule) and 7 methyl guanosine (m7G) to effectively sandwich m7G between 2 tryptophan residues. There are at least two endogenous eIF4E alleles (SEQ ID NO: 6 and SEQ ID NO: 35) as shown in the sequence listing and FIG. 2.

eIF4E protein can exist in free form or as part of a multiprotein pre-initiation complex termed EIF4E. The other subunits of EIF4E are EIF4F, EIF4A and EIF4G. Almost all cellular proteins require eIF4E in order to be translated into protein.

Some viruses cut eIF4G so that eIF4E binding site is removed. In doing so the virus can translate its own protein without eIF4E. Some cellular proteins, e.g., heat shock proteins, also don't require eIF4E in order to be translated.

As explained below, two new eIF4E-like genes were identified by the present inventors from wild potato genome, and are the ones that was surprisingly found to confer resistance to PVY virus.

3. Testing for PVY Virus Resistance

Resistance to PVY virus can be tested in the following manner: first, infect a plant by rubbing the plant's leaf surface with a leaf extract of PVY-infected host. Second, assess how long it takes for typical disease symptoms, such as leaf curling, and mild mottling, to occur. Longer time signifies resistance to PVY virus. More accurate, molecular level testing of PVY resistance can be done by using a PVY-specific enzyme-linked immunosorbent assay (ELISA) developed by Agdia (Elkhart, Ind.) to detect the presence of PVY protein. For example, see R. G. Bouzid et al, PVY-resistant transformed potato plants expressing an anti-NIa protein scFv antibody, Molecular Biotechnology, Volume 33, Number 2, 133-140, (2006). The ELISA assay can be performed according to the steps detailed in Example 12. The longer it takes for PVY protein to be detected in the plant, the more resistant the plant is to PVY virus. Thus testing for the presence of PVY protein is one method for determining the resistance state of any of transformed plants disclosed herein.

4. The New pwp1 and pwp2 PVY Resistance Gene Isolated From Wild Potato

Two new and unique eIF4E genes in wild potato (SEQ ID NO.: 1, SEQ ID NO:3) were identified and isolated as described herein. As explained below, these new sequences are given the name herein as "pwp1" and"pwp2". The significance of the pwp1 gene is exemplified by the fact that it is expressed in three of the five species analyzed: *Solanum etuberosum* accession PI245939, *S. chacoense* accessions PI175446 and PI175419, and *S. demissum* accession PI175423. The gene was not expressed in *S. stoloniferum* accessions PI195195 and PI275244, and *S. phureja*. The significance of pwp2 gene is exemplified by the fact that it is expressed in both accessions (PI195195 and PI275244) of the *S. stoloniferum* species.

The wild potato version of the pwp1 and pwp2 genes encode proteins (SEQ ID NO.: 2, SEQ ID NO: 4) that is surprisingly different from the eIF4E from cultivated potato (SEQ ID NO.: 5 for gene, SEQ ID NO.: 6 for protein) (FIG. 2). It has multiple unique amino acids that are different from any of the genes analyzed by the prior art (FIG. 3). The wild potato pwp1 protein contains ten amino acids that differ from the eIF4E from cultivated potato: (i) T54, (ii) S68, (iii) I70, (iv) K72, (v) T76, (vi) A77, (vii) V128, (viii) A130, (ix) S172 and (x) S175. The wild potato pwp2 protein contains five amino acids that differ from the eIF4E from cultivated potato: (i) T10, (ii) A23, (iii) Y57, (iv) N99, and (v) 5140.

Importantly, all three species (*Solanum etuberosum* accession PI245939, *S. chacoense* accessions PI175446 and PI175419, and *S. demissum* accession PI175423) expressing the new eIF4E gene pwp1 displayed resistance against the potyvirus PVY strains $PVY^0$ and $PVY^{WT}$. And both accessions (PI195195 and PI275244) of the *S. stoloniferum* species expressing the new eIF4E gene pwp2 displayed resistance against the potyvirus PVY strains $PVY^0$ and $PVY^{WT}$. The isolated genes are designated, therefore, as associated with "PVY resistance in wild potato" (pwp1 and pwp2).

These potato pwp1 and pwp2 sequences can readily be used to identify other plant sequences and genes useful for conferring PVY resistance to other species of plants. Such species include, but are not limited to, monocotyledenous plant, selected from the group consisting of wheat, turf, turf grass, cereal, maize, rice, oat, wheat, barley, sorghum, orchid, iris, lily, onion, banana, sugarcane, sorghum, and palm, and dicotyledenous plant, selected from the group consisting of avacado, potato, tobacco, tomato, sugarbeet, broccoli, cassaya, sweet potato, pepper, cotton, poinsetta, legumes, alfalfa, soybean, carrot, strawberry, lettuce, oak, maple, walnut, rose, mint, squash, daisy, and cactus.

Along those lines, it is shown herein that such sequences were used to identify PVY resistance genes from pepper: the modified pepper eIF4E, mpe1 (i.e., pepper equivalent of pwp1) can confer strong PVY resistance to potato species (FIGS. 9 and 10). The results in FIGS. 9 and 10 illustrates that a skilled artisan can readily use the modified eIF4E from one species to confer PVY resistance to another species.

The present invention comprises proteins that confer PVY resistance but which do not necessarily comprise a sequence that fits the consensus sequence of SEQ ID NO: 25: DXXXXKSBQXAWGSSXRXXYTFSXVEXF-WXXYNNIHBPSKLXXGAD, where X is neutral and B is a basic amino acid. See Robaglia and Caranta, Trends in Plant Science, 11 (1), pp.: 40-45, 2006; and U.S. Pat. No. 7,772,462. In another embodiment, the present invention comprises expressing a wild PVY resistance gene that may or may not comprise the SEQ ID NO: 25 or 38 consensus sequence in a cultivated plant that is not resistant to a PVY virus.

In this regard, neutral amino acid include alanine, asparagine, cysteine, glutamine, glycine, isoleucine, leucine, methionines, phenylalanine, proline, serine, threonine, tryptophan, tyrosine and valine. Basic amino acids include arginine, histidine and lysine. Acidic amino acids include aspartic acid and glutamic acid.

Furthermore, amino acid may be polar or non-polar. Non-polar amino acids include alanine, glycine, isoleucine, leucine, methionines, phenyl-alanine, proline and valine. Polar amino acids include arginine, asparagine, aspartic acid, cysteine, glutamic acid, glutamine, histidine, lysine, serine, threonine, tryptophan and tyrosine.

Amino acids may also be categorized as charged or non-charged. Charged amino acids include arginine, aspartate, glutamate, histidine and lysine.

Yet another way to categorize amino acids is hydrophobic versus hydrophilic. In this regard, hydrophobic amino acids include alanine, isoleucine, leucine, methionines, phenylalanine, proline, tryptophan, tyrosine and valine. Hydrophilic amino acids include arginine, asparagine, aspartate, cysteine, glutamine, glutamate, histidine, lysine, serine and threonine.

Amino acids may be further categorized as aliphatic or aromatic. Aliphatic amino acids include alanine, glycine, isoleucine, leucine and valine. Aromatic amino acids include histidine, phenylalanine, tryptophan and tyrosine.

Amino acids may also be modified. A large number of modified amino acids are commercially available through chemical reagent vendors, such as Sigma-Aldrich.

Typically, because a conserved substitution with the same type of amino acid (e.g., neutral to neutral) on a protein does not result in significant structure change of the protein, the function of the protein with the substituted amino acid is not expected to change. For example, a neutral to neutral substitution on eIF4E protein is not expected to significantly change its structure. In this regard, the present inventors unexpectedly discovered that the functions of the pwp1/pwp2 protein differ significantly from the native eIF4E protein despite the fact that the difference between the pwp1/pwp2 protein and the eIF4E protein are all conserved. In other words, the pwp1/pwp2 protein and the eIF4E protein do have different amino acids at certain positions. But these amino acid are of the same type, e.g., both neutral. Because these amino acids are of the same type, a person skilled in the art would not have expected pwp1/pwp2 to function significantly different from eIF4E.

As a result, a person skilled in the art typically does not expect conserved substitution to significantly alter the eIF4E protein's ability to bind vpg virus protein. Thus a conserved substitution in the eIF4E protein is not expected to change a plant's sensitivity to PVY virus.

In addition to the positions represented by X in SEQ ID NO: 25 or 38, a skilled artisan may make changes (i.e., substitutions) to the non-X residues. Changes may be conservative or non-conservative. In this regard, conservative changes mean that one amino acid is substituted by another amino acid having a similar property. For example, a polar amino acid substituted by another polar amino acid, a hydrophobic amino acid substituted by another hydrophobic amino acid, or a neutral amino acid substituted by another neutral amino acid. Non-conservative changes mean that one amino acid is substituted by another amino acid having a different property. For example, a neutral amino acid substituted by a basic amino acid or an acidic amino acid, a polar amino acid substituted by a non-polar amino acid, or a hydrophobic amino acid by a hydrophilic amino acid.

Changes may be made to 1-5, 5-10, 10-15, 15-20 amino acids of SEQ ID NO: 25 or 38. Upon making such changes to SEQ ID NO: 25 or 38, a skilled artisan can then transform a plant with the changed SEQ ID NO: 25 or 38 sequence and test PVY virus-resistance of the transformed plant. Testing procedure for PVY virus-resistance is set out in section 3 above.

5. Delayed Disease Progression in Cultivated Potato Plants Transformed With pwp1 and pwp2

One aspect of the present invention contemplates introducing the wild potato 1 and 2 (pwp1 and pwp2) gene into a plant in order to confer virus resistance. Transformation with pwp1 or pwp2 typically results in delayed disease progression, which means that, upon PVY virus infection, the transformed potato displays disease symptoms later than the untransformed potato. For example, in Example 5, the transformed potato with strong expression of pwp1 begins to display typical disease symptoms (leaf curling, and mild mottling) one week later than the other lines.

The pwp1 or pwp2 transformed plant can be, but is not limited to, a cultivated potato. And the virus resistance can be, but is not limited to, against PVY. This invention contemplates that the transformed plant be resistant to other PVY related viruses, such as potato virus X (PVX) and potato virus A (PVA). Pwp1 and pwp2 can be introduced into a plant via various means, which is well known in the art. For instance, transformation may rely on any known method for the insertion of nucleic acid sequences into a prokaryotic or eukaryotic host cell, including *Agrobacterium*-mediated transformation protocols, viral infection, whiskers, electroporation, heat shock, lipofection, polyethylene glycol treatment, micro-injection, and particle bombardment. Such means therefore can be, but are not limited to, *Agrobacterium*-mediated transformation (explained in detail in Example 2) or P-DNA mediated transformation (explained in detail in Example 5).

6. Transformation with pwp1 and pwp2 While Silencing The Endogenous eIF4E Gene

This invention further contemplates downregulating or inhibiting the expression of the native homology of pwp1 (the eIF4E gene) upon introducing the pwp1 or pwp2 gene into a plant's genome. The present inventors discovered that downregulating or inhibiting the expression of eIF4E gene in addition to expressing the full length pwp1 and pwp2 gene would result in full virus resistance. Instead of delayed progression of disease symptom, plants transformed with full length pwp1 or pwp2 in which the endogenous eIF4E is silenced are fully resistant to PVY virus. For instance, Example 6 contains detailed data on pwp1 transformed potato in which the endogenous eIF4E gene is silenced. In some transformed potato varieties disease symptoms do not occur even after 4 weeks of infection with PVY virus. ELISA assay did not detect PVY virus protein in these transformed potatoes. This invention is not limited to downregulating or inhibiting eIF4E via the silencing cassette in Example 6, because a person skilled in the art knows various ways of downregulating or inhibiting of the expression of a gene. In this regard, the endogenous eIF4E may be downregulated or inhibited by, but not limited to, convergent transcription, sense suppression, anti-sense suppression and RNAi.

The expression of the endogenous eIF4E gene may be downregulated through a convergent transcription technology as described in U.S. Pat. No. 7,713,735, which is incorporated by reference into the present application in its entirety. In this regard, a polynucleotide of eIF4E, such as a desired 20-50 nucleotide fragment of the eIF4E gene, and an inverted repeat of it are positioned in between, and are operably linked to, two functional promoters with opposite direction of transcription, where neither the eIF4E polynucleotide nor its inverted repeat is operably linked to a terminator. This construct may be located between transfer-DNA border sequences of a plasmid that is suitable for bacterium-mediated plant transformation. The construct may also contain a spacer up to 500 nucleotides long between the eIF4E polynucleotide and its inverted repeat. The promoters in the construct can be selected from a variety of different promoters including constitutive promoter, a near-constitutive promoter, a tissue-specific promoter and an inducible promoter.

The expression of the endogenous eIF4E gene may be downregulated or inhibited through RNA interference (RNAi) as described in Xia H et al., siRNA-mediated gene silencing in vitro and in vivo, *Nature Biotechnology* (2002), Vol. 20, 1006-1010, Wesley S V et al., Construct design for efficient, effective and high-throughput gene silencing in plants. *The Plant Journal* (2001) 27 (6), 581-590, Meister G et al., Mechanisms of gene silencing by double-stranded RNA, *Nature* (2004), Vol. 431, 343-349 and Hammond S et al., Post-Translational Gene Silencing by Double-Stranded RNA, Nature (2001), Vol. 2, 110-119, all of which are incorporated by reference into the present application in their entireties. In this regard, a self-complementary 'hairpin' RNA, or more generally, a microRNA or small interference RNA (siRNA) may be designed with techniques well known to an ordinarily skilled person in the art to bind to the messenger RNA (mRNA) of the eIF4E gene to decrease the activity of the mRNA, for example, by preventing the mRNA to produce a protein.

The expression of the endogenous eIF4E gene may be downregulated or inhibited through sense suppression as described in Kimura T., et al., Absence of amylose in sweet potato [Ipomoea batatas (L.) Lam.] following the introduction of granule-bound starch synthase I cDNA, *Plant Cell Reports* (2001), Vol. 20 (7), 663-666 and Chasen, R, Making Sense (Suppression) of Viral RNA-Mediated Resistance. *The Plant Cell*, Vol. 6, 1329-1331, all of which are incorporated by reference into the present application in their entireties. In this regard, sense suppression means that when the functionally active fragment or variant of a gene is introduced into the plant in sense orientation, it causes an identifiable decrease in expression of the corresponding gene in the transformed plant relative to an untransformed control plant. Sense-orientation means that the nucleic acid is in the same orientation or has the same polarity as a messenger RNA copy that is translated or translatable into protein. Therefore, in the case of the eIF4E gene, the sense-oriented strand of the endogenous eIF4E may be transferred into a plant to decrease the expression of endogenous eIF4E gene. The mechanisms of sense-suppression works include transcriptional inactivation or post-transcriptional RNA degradation. See Lindsey A R, *Transgenic Plant Research*, page 116, CRC Press (1998), which is incorporated by reference into the present application in its entirety.

The expression of the endogenous eIF4E gene may be downregulated or inhibited through anti-sense suppression as described in Romer S et al., Genetic Engineering of a Zeaxanthin-rich Potato by Antisense Inactivation and Co-suppression of Carotenoid Epoxidation., *Metabolic Engineering* (2002), Vol. 4 (4), 263-272, which is incorporated by reference into the present application in its entirety. In this regard, antisense suppression means that when the antisense-oriented strand of a gene is introduced into the plant in sense orientation, it causes an identifiable decrease in expression of the corresponding gene in the transformed plant relative to an untransformed control plant. Antisense-orientation means that the nucleic acid is in the opposite orientation or has the opposite polarity as a messenger RNA copy that is translated or translatable into protein. Therefore, in the case of the eIF4E gene, the antisense-oriented strand of the endogenous eIF4E may be transferred into a plant to decrease the expression of endogenous eIF4E gene. The mechanisms of antisense-suppression include the antisense strand of a target gene binding to the mRNA of the target gene and thereby blocking normal translation of the mRNA. See Lindsey A R, *Transgenic Plant Research*, page 116, CRC Press (1998).

7. Expression of Fragments of pwp1 or pwp2 Confers Resistance to Potyviruses

This invention further contemplates introducing fragments of the pwp1 or pwp2 genes, or the pvr1-2 gene from pepper, into a plant in order to confer virus resistance. It is discovered that, while plants transformed with full-length pwp1 or pwp2 display delayed disease progression upon PVY virus infection, plants transformed with fragments of pwp1 or pwp2 develop full resistance to PVY virus infection. For instance, Example 9 describes plants that are fully PVY resistant upon transformation with the potato pwp1 or pwp2 genes lacking approximately fifty amino acids at the N terminus. Additionally, plants transformed with a N-terminus-truncated pvr1-2 gene also develop full resistance to PVY virus infection. Example 9 contains detailed data on these transformed plants.

8. Modifying the Native eIF4E Gene in Cultivated Plants

In addition to introducing the wild potato 1 (pwp1) and wild potato 2 (pwp2) genes into a plant in order to confer virus resistance, this invention also contemplates substituting the eIF4E gene to make the eIF4E gene look like pwp1 or pwp2. For instance, the native eIF4E can be made to comprise at least two amino acids substitutions selected from the group consisting of (i) T44A (ii) S68N, (iii) I70T, (iv) K72R, (v) T76I, (vi) A77D, (vii) V128I, (viii) A130S, (ix) S172N and (x) S175V of SEQ ID NO:6, or (i) T10M, (ii) A23G, (iii) Y47F, (iv) N99Y, (v) L140P of SEQ ID NO: 6 (mutated sequences disclosed as SEQ ID NOS 83 and 84, respectively). Substituting specific amino acids can be achieved through site-directed mutagenesis, which is well known in the art. For instance, see Gilbertson L, Cre-lox Recombination: Cre-ative Tools for Plant Biotechnology, Trends in Biotechnology, Vol. 21 (21), 550-555 (2003) ("Gilbertson 2003"), which is incorporated herein by reference.

With regard to modifying a native eIF4E gene in plants, this invention also contemplates knocking out or inhibiting the expression of a native eIF4E gene of the plant and introducing into the plant at least one copy of a native eIF4E gene comprising at least two amino acid substitutions selected from the group consisting of (i) T44A (ii) S68N, (iii) I70T, (iv) K72R, (v) T76I, (vi) A77D, (vii) V128I, (viii) A130S, (ix) S172N and (x) S175V of SEQ ID NO:6, or (i) T10M, (ii) A23G, (iii) Y47F, (iv) N99Y, (v) L140P of SEQ ID NO: 6 (mutated sequences disclosed as SEQ ID NOS 83 and 84, respectively) (hereafter "an eIF4E gene with two substitutions").

In this regard, the expression of a native eIF4E gene of the plant can be knocked out or inhibited by methods including, but not limited to, convergent transcription technology, RNA interference (RNAi), sense suppression and anti-sense suppression, which are described in detail in section 6 above.

An eIF4E gene with two substitutions can be introduced into the plant by methods well known in the art. These methods include, but are not limited to:

(1) a marker-free transformation method as described in U.S. Pat. No. 7,619,138, which is incorporated by reference in its entirety, (2) a biolistic (or particle gun) method as described in Wright, M., Efficient biolistic transformation of maize (*Zea mays* L.) and wheat (*Triticum aestivum* L.) using the phosphomannose isomerase gene, pmi, as the selectable marker, Plant Cell Reports, Vol. 20 (5), 429-436 (2001), which is incorporated by reference in its entirety, (3) an *Agrobacterium* transformation method as described in Block M., Genotype-independent leaf disc transformation of potato (*Solanum tuberosum*) using *Agrobacterium tumefaciens*, Theor. Appl. Genet., Vol. 76, 767-774 (1988), which is incorporated by reference in its entirety, (4) a combination of the biolistic method and the *Agrobacterium* transformation methods as described in Hansen G. et al., "Agrolistic" transformation of plant cells: Integration of T-strands generated in planta, Proc. Natl. Acad. Sci. U.S.A., Vol. 93 (25), 14978-14983 (1996), which is incorporated by reference in its entirety, (5) a cre-lox method as described in Gilbertson 2003.

9. Stacked Traits

In additional to virus resistance, additional traits of a plant may be modified. Such traits may include, but are not limited to, late blight resistance, low reducing sugar, low free asparagines, low bruising, reduced cold-induced sweetening, low acrylamide, reduced starch phosphate level and increased antioxidant. A number of methods are known in the art to modify a plant to possess additional traits. For example, a method to confer late blight resistance is described in Song J, et al, Gene RB cloned from *Solanum bulbocastanum* confers broad spectrum resistance to potato late blight. *PNAS* (2003) Vol. 100 (16): 9128-9133, which is incorporated by reference into the present application in its entirety. A method to confer the trait of low reducing sugar is described in U.S. Pat. No. 7,250,554. A method to confer the trait of low free asparagines is described in European Patent No. 1974039. Methods to confer the traits of low bruising, reduced cold-induced sweetening or reduced starch phosphate level are described in U.S. Pat. No. 7,250,554. A method to confer the trait of low acrylamide is described in U.S. published patent application 2007/0074304 and U.S. Pat. No. 7,250,554. A method to confer the trait of increased antioxidant is described in U.S. Pat. No. 7,855,319. U.S. Pat. No. 7,250,554, European Patent No. 1974039, U.S. Pat. No. 7,855,319 and other patents or published applications cited herein are incorporated by reference into the present application in their entireties.

A plant of the present invention can be modified to have any combination of these traits. For example, a plant can be modified to have various combinations traits, such as, but not limited to, various combinations and permutations of Trait (1) PVY resistance (full or delayed); Trait (2) late blight resistance, Trait (3) low reducing sugar, Trait (4) low free asparagines, Trait (5) low bruising, Trait (6) reduced cold-induced sweetening, Trait (7) low acrylamide, Trait (8) reduced starch phosphate level, Trait (9) increased antioxidants; and Trait (10) increased vitamin content, such as increased vitamin C. For instance, Trait (1) (i.e., PVY resistance) may be combined with one or more of Traits (2)-(10). Accordingly, the present technology contemplates the pair wise combination of Trait (1) with (2); (1) and (3); (1) and (4); (1) and (5); (1) and (6); (1) and (7); (1) and (8); (1) and (9); (1) and (10); as well as every other combinational permutation of these Traits. In addition to the combination of Trait (1) with one of more of the Traits (2)-(10), the present invention also contemplates other traits that a person of ordinary skill in the art can stack or combine with Trait (1).

The following examples serve to illustrate various embodiments of the present invention and should not be construed, in any way, to limit the scope of the invention.

All references cited herein, including patents, patent application and publications, are hereby incorporated by reference in their entireties, where previously specifically incorporated or not.

Having now fully described this invention, it will be appreciated by those skilled in the art that the same can be performed within a wide range of equivalent parameters, concentrations and conditions, without undue experimentation. This application is intended to cover any variations, uses, or adaptations of the invention, following in general the principles of the invention, that include such departures from the present disclosure as come within known or customary practice within the art to which the invention pertains and as may be applied to the essential features hereinbefore set forth.

EXAMPLES

Example 1

Cloning and Characterization of Wild Potato EIF4E Alleles

Two new and unique eIF4E genes in wild potato are disclosed herein. The nucleic acid sequence for the first new gene is depicted in SEQ ID NO.: 1. It was found that this new gene is expressed in individual segregating plants (not all plants) of specific accessions of three of five species analyzed:

Individual plants of *Solanum etuberosum* accession PI245939;

Individual plants of *S. chacoense* accessions PI175446 and PI175419; and

Individual plants of *S. demissum* accession PI175423.

This gene was not expressed in three plants of *S. stoloniferum* accessions PI195195 and PI275244, and *S. phureja*. However, it is possible that more extensive analyses of the accessions mentioned would identify individual segregating plants expressing the gene shown in SEQ ID NO.: 1.

The nucleic acid sequence for the second gene is depicted in SEQ ID NO.: 3. It was found that this new gene is expressed in individual segregating plants (not all plants) of two accessions of *S. stoloniferum.*

*S. stoloniferum* accession PI195195 and PI27524.

This gene was not expressed in three plants of *Solanum etuberosum* accession PI245939, *S. chacoense* accessions PI175446 and PI175419, *S. demissum* accession PI175423 and *S. phureja*. However, it is possible that more extensive analyses of the accessions mentioned would identify individual segregating plants expressing the gene shown in SEQ ID NO.: 3.

Importantly, all plants expressing eIF4E pwp1 and pwp2 genes were resistant to potyvirus PVY strains $PVY^{0}$ and $PVY^{WT}$.

Because the isolated, wild potato eIF4E genes are associated with PVY resistance in wild potato 1 and 2, they are designated herein as pwp1 and pwp2.

The wild potato eIF4E gene, i.e., "pwp1," encodes a protein with the amino acid sequence depicted in SEQ ID NO.: 2 that is surprisingly different from the cultivated potato eIF4E gene. The DNA sequence for the cultivated potato eIF4E gene is depicted in SEQ ID NO.: 5 and the encoded amino acid protein sequence depicted in SEQ ID NO.: 6. See FIG. 2 for the wild vs. cultivated alignment.

The wild potato eIF4E gene, i.e., "pwp2," encodes a protein with the amino acid sequence depicted in SEQ ID NO.: 4 that is surprisingly different from the cultivated potato eIF4E gene. The DNA sequence for the cultivated potato eIF4E gene is depicted in SEQ ID NO.: 5 and the encoded amino acid protein sequence depicted in SEQ ID NO.: 6. See FIG. 2 for the wild vs. cultivated alignment.

The pwp1 and pwp2 proteins have multiple unique amino acid substitutions that are different from any of the genes analyzed by the prior art. See FIG. 3. For instance, the wild potato pwp1 protein contains a first pair of substitutions at positions 72 and 76 (K72R and T76I), a second pair at positions 128 and 130 (V128I and A130S) and a third pair at positions 172 and 175 (S172N and S175V). The wild potato pwp2 protein contains five substitutions through the protein (T10M, A23G, Y47F, N99Y and L140P).

Example 2

Binding Properties of the pwp1 and pwp2 Proteins

The products of the pwp1 and pwp2 genes were tested for their ability to bind the viral vpg protein by using the yeast two-hybrid system. For this purpose, the pwp1 or pwp2 cDNA was cloned into vector pAD (Stratagene), which also contains a leucine (Leu) biosynthetic marker, to produce a "prey" protein. The "bait" protein was produced by expressing the Vpg gene into pBD (Stratagene), a vector also carrying a tryptophan (Trp) biosynthetic marker.

As shown in FIG. 4, co-transformation of the yeast strain YRG-2 with the modified pAD and pBD vectors (according to the manufacturer's recommendations) produced colonies on media lacking Leu and Trp but not on media also lacking histidine (His).

In contrast, co-transformations of a control prey vector expressing the potato eIF4E gene with the vpg-containing pBD vector resulted in colony formation on media lacking the three amino acids, indicating that only the potato eIF4E protein interacted with vpg, thus activating downstream His biosynthesis. The inability to bind with vpg suggests that pwp1 and pwp2 expression are associated with PVY resistance in wild potato.

Many of the changes of pwp1 were positioned within domains implicated in mRNA cap binding and VPg interaction. In fact, five of the substitutions (S68N, I70T, K72R, T76I and A77D) were within a degenerate 46-amino acid domain that was predicted to be the hotspot for potyvirus resistance-linked mutations. See FIG. 2, and Robaglia and Caranta, Trends in Plant Science, 11 (1), pp.: 40-45, 2006. In contrast to the expected changes, from either neutral to charged or charged to neutral or oppositely charged amino acids, it was discovered herein that four of substitutions, S68N, I70T, T76I and K72R, involved the substitution of the endogenous native basic amino acids with other basic amino acids, or the endogenous native neutral amino acids to other neutral amino acids (S, N, I and T are all neutral and both K and R are basic). The only mismatch that was previously predicted to be associated with resistance, A77D, did not interfere with binding of VPg in the yeast two-hybrid system, and was, therefore, not believed to be critical in mediating resistance (FIG. 4). This finding implies that pwp1 belongs to a new group of eIF4E variants.

Example 3

Method for Identifying Other pwp Homologs & Sequences

Accessions of wild potato species, some of which are maintained at the United States Potato Genebank and elsewhere, can be grown in the greenhouse and evaluated to determine the presence in their genomes of a pwp1 gene or homolog. Specifically, RNA from leaves of individual plants, isolated with the plant RNA-easy kit (Invitrogen), can be used in one-step reverse-transcriptase PCR reactions (Qiagen) with the primer pair 5'-GGA TCC ATG GCA GCA GCT GAA ATG (SEQ ID NO: 81), and 5'-ACT AGT CTA TAC TGT GTA ACG ATT CTT GGC A (SEQ ID NO: 82) to produce pwp1 cDNAs. Amplified products are then gel purified, and cloned into pGEM-Teasy (Promega), and sequenced.

Example 4

Transfer of pwp1 and pwp2 From Wild to Cultivated Potato

The pwp1 cDNA was operably linked to the near-constitutive 35S promoter of cauliflower mosaic virus (SEQ ID NO.: 7) and the terminator of the potato ubi3 gene (SEQ ID NO.: 8). The resulting expression cassette was positioned within a T-DNA region of a binary vector to produce pSIM1567. The pwp2 cDNA was operably linked to the near-constitutive PAT promoter of potato (SEQ ID NO.: 9) and the terminator of the potato ubi3 gene (SEQ ID NO.: 8). The resulting expression cassette was positioned within a T-DNA region of a binary vector to produce pSIM1569. These transformation vectors were used to transform the potato variety Ranger Russet as follows.

Competent LB4404 cells (50 μL) were incubated for 5 minutes at 37° C. in the presence of 1 μg of vector DNA, frozen for about 15 seconds in liquid nitrogen (about −196° C.), and incubated again at 37° C. for 5 minutes. After adding 1 ml of liquid broth (LB), the treated cells were grown for 3 hours at 28° C. and plated on LB/agar containing streptomycin (100 mg/L) and kanamycin (100 mg/L). The vector DNAs were then isolated from overnight cultures of individual LBA4404 colonies and examined by restriction analysis to confirm the presence of intact plasmid DNA.

Ten-fold dilutions of overnight-grown *Agrobacterium* cultures were grown for 5-6 hours, precipitated for 15 minutes at 2,800 RPM, washed with MS liquid medium (Phytotechnology) supplemented with sucrose (3%, pH 5.7), and resuspended in the same medium to 0.2 OD/600 nm. The resuspended cells were mixed and used to infect 0.4-0.6 mm internodal segments of potato. Infected stems were incubated for two days on co-culture medium (1/10 MS salts, 3% sucrose, pH 5.7) containing 6 g/L agar at 22° C. in a Percival growth chamber (16 hrs light) and subsequently transferred to callus induction medium (CIM, MS medium supplemented with 3% sucrose 3, 2.5 mg/L of zeatin riboside, 0.1 mg/L of naphthalene acetic acid, and 6 g/L of agar) containing timentin (150 mg/L) and kanamycin (100 mg/L).

After one month of culture on CIM, explants were transferred to shoot induction medium (SIM, MS medium supplemented with 3% sucrose, 2.5 mg/L of zeatin riboside, 0.3 mg/L of giberellic acid GA3, and 6 g/L of agar) containing timentin and kanamycin (150 and 100 mg/L respectively) until shoots arose. Shoots arising from the explants were transferred to MS medium with 3% sucrose, 6 g/L of agar and timentin (150 mg/L). Individual leaves from then independent transformants were confirmed by PCR to contain the T-DNA, and then transferred to soil and placed in a growth chamber (11 hours light, 25° C.).

Transgenic control plants were produced by transforming Ranger Russet with binary vector pSIM401, which only contains the nptII gene expression cassette between T-DNA borders.

Example 5

Delayed Disease Progression in pwp1 Transgenic Potato

Figure 5:
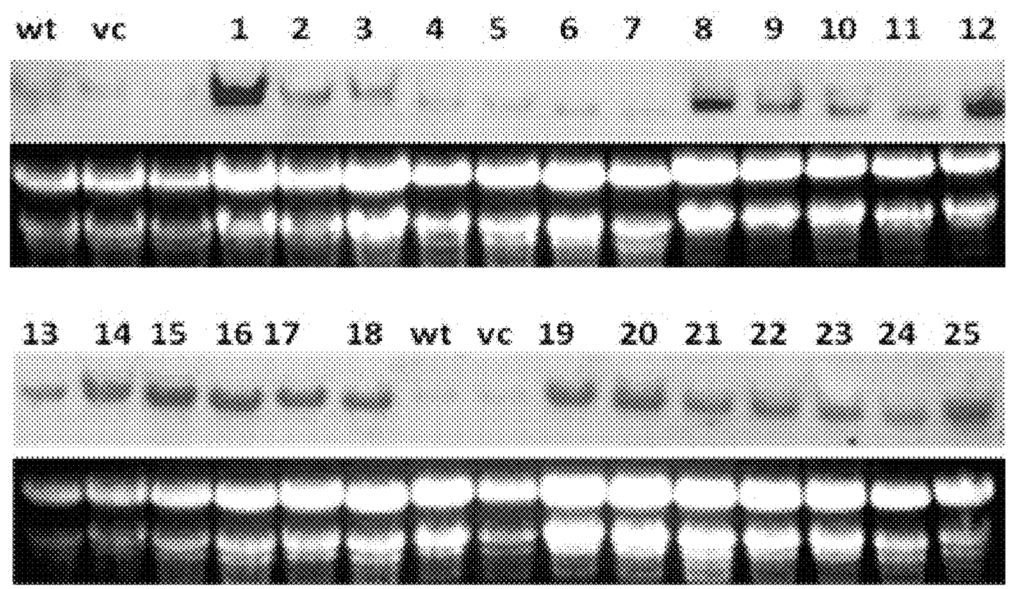
FIG. 5: RNA gel blot analysis of pSIM1567 plants. RNA was isolated from leaf tissues of wild type Burbank (wt), empty vector control (vc) and transgenic pSIM1567 (1-25) plants, run on the gel, transferred to nylon membrane and hybridized with Dig-labeled potato EIF4E probe according to standard protocol. EB-stained ribosome RNA was used as loading control.

Transgenic pSIM1567 plants and their pSIM401 controls were propagated in vitro to produce lines, and three copies of each line were transferred to soil. Leaf tissues were used to extract RNA and perform northern blot analysis using an eIF4E-derived probe. This probe visualizes the total amount of transcript for both the potato eIF4E gene and the pwp1 gene from wild potato. Assuming constant expression levels of the eIF4E gene, any increase in transcript levels was assumed to be associated with expression of the pwp1 gene. Thus, as shown in FIG. 5, most pSIM1567 plants were found to express the pwp1 gene. Highest expression levels were observed in lines pwp1-1, 8, 12, 15 and 25.

After two weeks, the transgenic plants were infected with PVY by rubbing a leaf extract of PVY-infected host plants onto their leaf surface. Plants were assessed for typical disease symptoms (leaf curling, and mild mottling) after both two and three weeks. Leaves of the infected plants were also analyzed with a PVY-specific enzyme-linked immunosorbent assay (ELISA) developed by Agdia (Elkhart, Ind.) for the presence of PVY protein.

Interestingly, disease progression was delayed in 2 lines (1567-15 and 1567-25) that expressed the pwp1 gene strongly. These lines developed disease symptoms one week later than all other lines (Table 2).

Example 6

Enhanced Effect of pwp1 Gene Expression Upon Silencing of the Potato eIF4E Gene

Sequence analysis of the 5'-untranslated leader and 3'-untranslated trailer allowed us to produce a DNA fragment carrying these eIF4E-specific sequences (SEQ ID NO.: 10). Two copies of this fragment were positioned as inverted repeat between the strong Pat promoter (SEQ ID NO.: 9) and the terminator of the potato ubiquitin-3 gene to produce an expression cassette intended to silence the eIF4E gene but not the homologous pwp1 gene. The silencing cassette was inserted next to an expression cassette of the Bar gene within the T-DNA borders of a binary vector to produce pSIM1895, and this vector was used to re-transform Ranger Russet line 1567-25.

Nine kanamycin and Bar resistant double-transformants were propagated in vitro, and three plants of each line were planted in soil, placed for two weeks in a growth chamber, and then infected with PVY. Two weeks after infection, six out of nine lines showed full PVY resistance as determined by the ELISA assay (Table 3). One week later, this resistance was still evident in three lines. Even four weeks after infection, no PVY protein could be detected in two of the 1567-25/1895 lines. Thus, overexpression of the pwp1 gene, together with eIF4E gene silencing, triggers effective disease resistance against PVY.

In one control experiment, a potato plant was transformed with the eIF4E silencing construct. Infection of 13 Bar-resistant lines (three plants/line) did not result in any control of PVY.

Example 7

Overexpression of pwp2 in Potato Delayed Disease Progression in Transgenic Potato Twenty-five transgenic pSIM1569 plants and their pSIM401 controls were propagated in vitro to produce lines, and three copies of each line were transferred to soil, placed for two weeks in a growth chamber, and then infected with PVY. Two weeks after infection, 4 out of twenty-five lines (No. 9, 16, 23 and 25) showed full PVY resistance as determined by the ELISA assay. Three weeks after infection, no PVY protein could be detected in two of the 1569 lines, No. 16 and No. 23. However, at four weeks after infection, all lines showed PVY-infected symptom and were tested as PVY positive by ELISA (Table 4). Thus, overexpression of the pwp2 gene also delayed disease progression. Four lines that showed resistance at two weeks and one susceptible line (No. 18) were selected for expression study. Leaf tissues were used to extract RNA and perform northern blot analysis using an eIF4E-derived probe. This probe visualizes the total amount of transcript for both the potato eIF4E gene and the pwp2 gene from wild potato. Assuming constant expression levels of the eIF4E gene, any increase in transcript levels was assumed to be associated with expression of the pwp2 gene.

Figure 8:
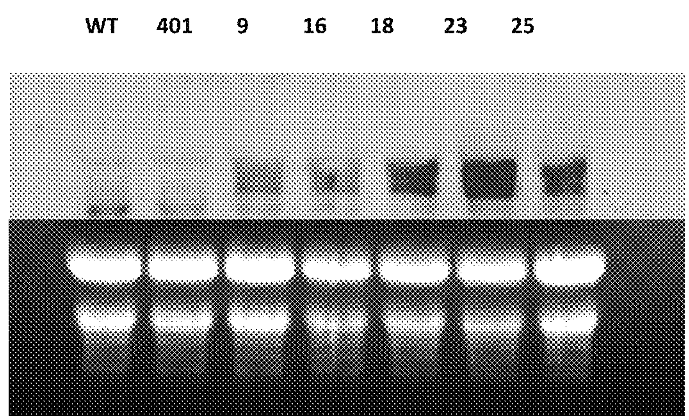
FIG. 8: RNA gel blot analysis of selected pSIM1569 plants. RNA was isolated from leaf tissues of wild type Burbank (wt), empty vector control (401) and transgenic pSIM1569 (9, 16, 18, 23, 25) plants, run on the gel, transferred to nylon membrane and hybridized with Dig-labeled potato EIF4E probe according to standard protocol. EB-stained ribosome RNA was used as loading control.

As shown in FIG. 8, all 5 pSIM1569 plants checked were found to express the pwp2 gene. Highest expression levels were observed in line pwp2-23.

Example 8

Development of Intragenic PVY Resistant Potato Plants

Figure 6:
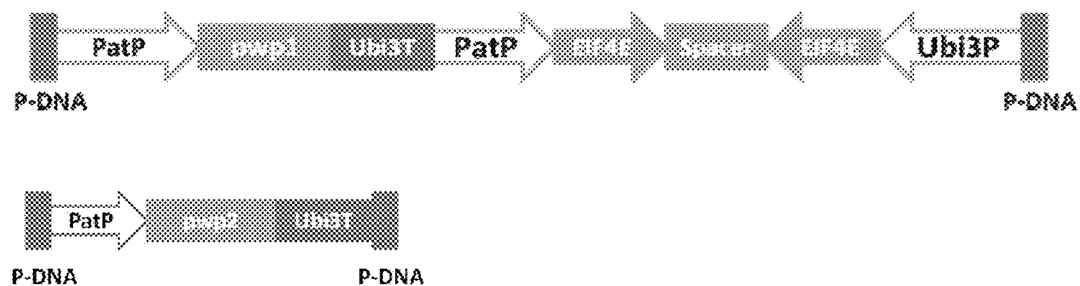
FIG. 6: All-native transfer DNA for PVY control.

A transfer DNA was designed that consists exclusively of DNA elements derived from either potato or sexually-compatible wild potato (FIG. 6). This transfer DNA comprises a first expression cassette for the pwp1 gene fused to the near-constitutive Pat promoter and the ubi3 terminator. The second cassette contains two copies of the untranslated 5' and 3' sequences of the potato eIF4E gene separated by a potato spacer and positioned between the same regulatory elements. These two cassettes are placed within a potato-derived transfer DNA. See SEQ ID NO.: 11 for the entire sequence.

Marker-free transformation of potato with the all-native transfer DNA (as described in Rommens et al., 2004 and Richael et al., 2008) creates intragenic plants, some of which display PVY resistance.

Example 9

Expression of Fragments of Specific eIF4E Genes Confers Resistance to Potyviruses Cloning and Deletion Mutagenesis of pvr1-2 Allele From Pepper RNA was isolated from leaves of the pepper variety that contains the pvr1-2 gene for resistance against potyviruses, using the plant RNA-easy kit (Qiagen). The RNA was used in one-step reverse-transcriptase PCR reactions (Qiagen) with the primer pair 5'-GGG GAT CCA TGG CAA CAG CTG AA AT (SEQ ID NO: 36), and 5'-CCA CTA GTC TAT ACG GTG TAA CGA T (SEQ ID NO: 37) (carrying the restriction sites BamHI and SpeI, respectively) to amplify a DNA fragment representing a cDNA of the pvr1-2 gene. Amplified products were gel purified and cloned into pGEM-Teasy (Promega); the amino acid sequence encoded by the cDNA is shown in SEQ ID NO: 12. A fragment of the cDNA was obtained by removing the 5'-part of this cDNA using the primers del25-73sense 5'-GAT TGG GGA TCC ATG GCA AAG CAT CCA TTA GAG CAT-3' (SEQ ID NO: 12) and del25-73antisense 5'-ATG CTC TAA TGG ATG CTT TGC CAT GGA TCC CCA ATC-3' (SEQ ID NO: 13) in an 18-cycleamplification reaction with Pfu Ultra II Fusion HS DNA Polymerase (Agilent). A total of 2 μl DpnI enzyme was added and the reaction incubated for 2 hrs to cleave the template molecules. 5 μl of this reaction was then transformed into DH5α competent cells (Invitrogen). Individual deleted clones were sequenced to identify an error-free clone, which was further subcloned into binary vector.

pSIM1719 Construct and Transformation into Potato

The sequence for complete pvr1-2 is shown as SEQ ID No.: 14. The pvr1-2-derived fragment, designated here as Fpvr (see SEQ ID No.: 15 for DNA sequence, SEQ ID NO: 16 for amino acid sequence), was operably linked to the near-constitutive PAT promoter of potato (SEQ ID NO.:9) and the terminator of the potato ubi3 gene (SEQ ID NO.: 8). The resulting expression cassette was positioned between T-DNA borders of a binary vector to produce pSIM1719. An *Agrobacterium* LBA4404 strain carrying this transformation vector was used to transform the potato variety Burbank Russet as described in example 4.

Expression Analyses and Disease Assay for Transgenic Lines Containing pSIM1719

Figure 7:
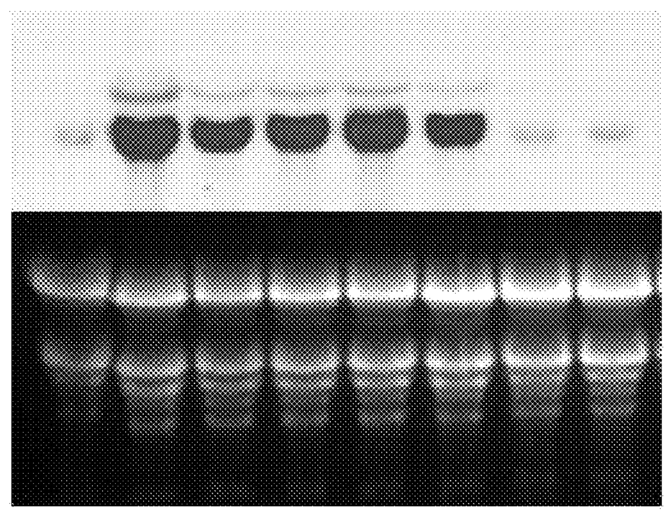
FIG. 7: Transcript levels of Fpvr in leaves of pSIM1719 lines. RBc is the Russet Burbank control and 401c is the empty vector control.

Transgenic pSIM1719 plants and their pSIM401 controls were propagated in vitro to produce lines, and three copies of each line were transferred to soil. Leaf tissues were used to extract RNA and perform northern blot analysis using an eIF4E-derived probe. 20 μg of leaf RNA was used for Northern analyses. This probe visualizes the total amount of transcript for pepper eIF4E gene. High expression levels were observed in lines 1719-11, 17, 20, 23 (FIG. 7).

The disease progression was checked as described in example 5. Two weeks after infection three lines pSIM1719-11, 17 and 20 showed no symptoms of infection and were negative in ELISA. Lines pSIM1719-11, 17 remained negative in ELISA even after four weeks post infection. Thus, expression of Fpvr was sufficient to confer PVY resistance to potato.

Most differences between pepper and potato eIF4e protein are in the N-terminal region of the protein and Fpvr might be more stable in providing resistance. The Fpvr fragment and a similar potato fragment shown in SEQ ID NO.: 17 show only 11 amino acid differences (SEQ ID NO.:16 and SEQ ID NO.: 17) and 46 differences between their respective nucleotide sequences (SEQ ID NO.:15 and SEQ ID NO.: 18).

Resistance can also be obtained by making transgenic plants having similar near constitutive expression of the fragment region with of the pwp1 (SEQ ID NO.: 19 and SEQ ID NO.: 20), pwp2 (SEQ ID NO.: 21 and SEQ ID NO.: 22) and mpe mutations (SEQ ID NO.: 23 and SEQ ID NO.: 24) discussed in EXAMPLE 10 below.

Example 10

The proteins encoded by previously-identified eIF4E genes implicated in potyvirus resistance comprise an amino acid domain with the consensus:

```
                                        (SEQ ID NO: 25)
DXXXXKSBQXAWGSSXRXXYTFSXVEXFWXXYNNIHBPSKLXXGAD
```

where X is a neutral amino acid and B is a basic amino acid. See Robaglia and Caranta, Trends in Plant Science, 11 (1), pp.: 40-45, 2006; and U.S. Pat. No. 7,772,462.

In addition to the pwp1 gene from wild potato species that encodes a protein with ten differences at positions that are generally conserved, including two amino acids (K69R and A74D, position based on pepper eIF4E protein) that are inconsistent with the consensus for resistance-associated eIF4E mutations, and pwp2 gene from wild potato that encodes a protein with five mismatches at positions that are generally conserved, including one amino acid (N96Y, position based on pepper eIF4E protein) that are inconsistent the consensus for resistance associated eIF4E mutations.

Two mutant eIF4E genes were created from pepper (mpe, modified CaeIF4E genes) that encodes protein conferring potyvirus resistance to potato without containing an amino acid sequence that conforms to the consensus sequence. The DNA and amino acid sequence of modified pepper eIF4E gene 1 is shown in SEQ ID NO: 26 and SEQ ID NO.: 27. The DNA and amino acid sequence of modified pepper eIF4E gene 2 is shown in SEQ ID NO.: 28 and SEQ ID NO: 29, respectively. Also created herein was a mutant eIF4E gene from potato that encodes protein potentially conferring potyvirus resistance to potato without containing an amino acid sequence that conforms to the consensus sequence. The DNA and amino acid sequence of this modified potato eIF4E gene are shown in SEQ ID NO: 30 and SEQ ID NO: 31, respectively.

Transformation of potato with an expression cassette comprising either of the modified CaeIF4E genes operably linked to the PAT promoter (pSIM1588 and pSIM1723, FIGS. 9 and 10) resulted in full resistance against PVY as determined by ELISA assays, carried out 4 weeks after infection. FIGS. 9 and 10 also show the transformed mpe genes are more or less overexpressed in selected lines compared to wild type and empty vector control plants.

Example 11

The sequences described in Examples 1-9 could similarly be used to engineer potyvirus resistance in lettuce and tomato when expressed under the control of near-constitutive promoters such as 35S or PAT (SEQ ID NO: 7 and SEQ ID NO: 9 respectively) and ubi3 terminator (SEQ ID NO: 8) as mentioned before. The resulting expression cassette can be positioned within a T-DNA region of a binary vector. The resultant binary vector containing the gene of interest described in this example is then transformed into an Agrobacterial strain LBA4404 and can subsequently be transformed into lettuce or tomato as per the transformation protocols described below. Transgenic control plants can be produced by transforming lettuce or tomato plants with a control binary vector containing just a selectable marker such as nptII expression cassette within the T-DNA borders.

Lettuce Transformation

For sterilization, lettuce seeds were immersed for 30 sec to 1 min in 70% ethanol and 15 min. in 10% bleach with a trace of Tween20, followed by 3 rinses with sterile water. Seeds (30-40 per Magenta box) were spread evenly over medium consisting of half-strength MS medium with vitamins (M404, Phytotechnology) with 10 g sucrose per liter, solidified with 2% Gelrite, pH 5.7. Seed germinated at 24° C. with 16/8 L/D.

*Agrobacterium* harboring a gene of interest such as pSIM1723 (modified pepper eIF4E 2, mpe2, constitutively expressed using PAT promoter (SEQ ID NO: 9) and ubi3 terminator (SEQ ID NO: 8) was grown overnight from frozen glycerol stock (−80° C.) in a small volume of Luria Broth with kanamycin and streptomycin selective agents. Two milliliters of the log-phase over-night culture was added to 18 ml of new LB with selection and growth with shaking until log phase. Agro was spun down and suspended in liquid MS medium to achieve an $OD_{600}$ of 0.2.

Seven days from sowing, the cotyledons were excised from seedlings and wounded with a scalpel to give small cuts at right angles to the mid-vein. All explants were immersed in the above Agrobacterial suspension. After 10 minutes, the Agrobacterial suspension was aspirated away and the explants were blotted on sterile filter paper. Explants were placed adaxial side up on co-culture medium that consisted of MS medium with vitamins (M404, Phytotechnology), 30 g sucrose per liter, 0.1 mg/l BAP, 0.1 mg/l NAA and solidified with 6 g/l agar, pH 5.7. After two days co-culture, explants were moved to regeneration medium that consisted of MS medium with vitamins (M404), 30 g sucrose per liter, 0.1 mg/l BAP, 0.1 mg/l NAA and solidified with 6 g/l agar, pH 5.7 and 150 mg/l of timentin and 100 mg/l kanamycin. Every two weeks, explants are moved to new regeneration medium. After 2-3 weeks, shoot buds are harvested and transferred to medium that consisted of MS medium with vitamins (M404), 30 g sucrose per liter, 0.01 mg/l BAP, 0.05 mg/l NAA and solidified with 6 g/l agar, pH 5.7 and 150 mg/l of timentin and 100 mg/l kanamycin. Two to four weeks later, elongated shoots are transferred to rooting medium (MS medium without hormones and with 150 mg/l timentin and 100 mg/l kanamycin).

Tomato Transformation

Tomato transformation was done essentially as described by Richael et al., 2008. Seeds of tomato (cv. Money Maker) were surface sterilized in 20% commercial bleach with 2 drops of Tween-20 for 20 min and rinsed with sterilized water 3 times for 10 min each. The seeds were germinated on M404 medium containing 1.5% sucrose and 6 g/l agar (germination medium). Hypocotyls of 12 to 14-day old seedlings were cut into segments 5 to 8 mm and infected by *Agrobacterium*. For ipt-based transformation, infected explants were transferred to cocultivation medium containing 200 1M acetosyringone. After 2 days, cultivated explants were transferred to the hormone-free medium. Explants were transferred to fresh medium every 2 weeks. For a conventional tomato transformation (conventional-Tm) the co-cultivated explants were transferred to M404 medium containing 2.5 mg/l ZR, 0.1 mg/l indole-3-acetic acid (IAA), 75 mg/l kanamycin and 150 mg/l timentin (selective medium). Explants were transferred to the fresh selective medium every 2 weeks. After one month of cultivation 0.3 mg/l GA3 was added to the selective medium for shoot elongation.

The transgenic plants thus produced are propagated in vitro, and three plants of each line planted in soil and placed in growth chamber for 2 weeks and can then be infected with PVY. Progression of susceptible and resistant lines can be checked after 2 and 4 weeks by ELISA assay as described for potato. The transgenic plants still resistant to PVY and negative in ELISA can be further confirmed for transgene expression by northern analyses as described for potato.

REFERENCES

Rommens, C M, Haring M A, Swords, K, Davies H V and Belknap, W R (2007) The intragenic approach as a new extension to traditional plant breeding. Trends in Plant Sci 12 (9): 397-403.

Richael, C M, Kalyaeva, M, Chretien, R C, Yan, H, Adimulam, S, Stivison, A, Weeks, J T and Rommens C M. (2008) Cytokinin vectors mediate marker-free and backbone-free plant transformation. Transgenic Res. 17:905-917.

Example 12

ELISA Assay

Enzyme-linked immunosorbent assay (ELISA) is an assay that relies on an enzymatic conversion reaction and is used to detect the presence of an antibody or an antigen in a sample. The ELISA has been used as a diagnostic tool in medicine and plant pathology, as well as a quality-control check in various industries. In simple terms, in ELISA, an unknown amount of antigen is affixed to a surface, and then a specific antibody is applied over the surface so that it can bind to the antigen. This antibody is linked to an enzyme, and, in the final step, a substance containing the enzyme's substrate is added. The subsequent reaction produces a detectable signal, most commonly a color change in the substrate. In the present invention, ELISA is used to detect the presence of PVY virus protein. An ELISA assay typically comprises the following steps.

1. Dispense Samples:

Following a loading diagram, dispense 100 μl of prepared sample into sample wells. Dispense 100 μl of positive control into positive control wells, and dispense 100 μl of general extract buffer into buffer wells. If using a negative control, dispense 100 μl into negative wells.

2. Incubate Plate:

Set the plate inside the humid box and incubate for 2 hours at room temperature or overnight in the refrigerator (4° C.).

3. Prepare Enzyme Conjugate:

Both bottles of alkaline phosphatase enzyme conjugate and detection antibody (bottles A and B) are supplied as a concentrate and must be diluted with ECI buffer before use. The recommended conjugate to buffer ratio is given on each label. Dispense the appropriate volume of prepared ECI buffer into a dedicated container. 100 μl of buffer for each test well is needed. A full plate will require about 10 ml. Then, add the alkaline phosphatase enzyme conjugate according to the dilution given on the labels. For example, if the dilution given on bottles A and B of concentrated detection antibody and alkaline phosphatase enzyme conjugate is 1:100, and tester are preparing 10 ml of enzyme conjugate solution, the tester should first dispense 10 ml ECI buffer. Then, add 100 μl from bottle A and 100 μl from bottle B to the ECI buffer. After adding the reagents from bottles A and B, it is important to mix the enzyme conjugate solution well.

4. Wash Plate:

When the sample incubation is complete, wash the plate. Use a quick flipping motion to dump the wells into a sink or waste container without mixing the contents. Fill all the wells completely with 1×PBST, and then quickly empty them again. Repeat 7 times. After washing, hold the frame upside down and tap firmly on a folded paper towel to remove all droplets of wash buffer. Inspect the testwells. All wells should be free of plant tissue. If tissue is present repeat the wash step and tap firmly on a paper towel.

5. Add Enzyme Conjugate:

Dispense 100 μl of prepared enzyme conjugate per well.

6. Incubate Plate:

Incubate the plate in the humid box for 2 hours at room temperature.

7. Prepare PNP Solution:

Each PNP tablet (ACC 00404) will make 5 ml of PNP solution, at a concentration of 1 mg/ml, about enough for five 8-well strips. About 15 minutes before the end of the above incubation step, measure 5 ml of room temperature 1×PNP buffer for each tablet tester will be using. Then, without touching the tablets, add the PNP tablets to the buffer.

8. Wash Plate:

As before, wash the plate 8 times with 1×PBST. Inspect the wells looking for the presence of air bubbles. Tap firmly on the paper towel to remove remaining wash buffer and any air bubbles. If air bubbles are still present they may be broken with a clean pipette tip.

9. Add PNP Substrate:

Dispense 100 μl of PNP substrate into each test well.

10. Incubate Plate:

Incubate the plate in a humid box for 60 minutes. Plates should be protected from direct or intense light.

11. Evaluate Results:

Examine the wells by eye, or measure on a plate reader at 405 nm. Air bubbles which are present at the time of reading can alter results, if in the light path. It is recommended that bubbles be eliminated prior to reading. Wells in which color develops indicate positive results. Wells in which there is no significant color development indicate negative result. Test results are valid only if positive control wells give a positive result and buffer wells remain colorless. Results may be interpreted after more than 60 minutes of incubation as long as negative wells remain virtually clear.

TABLE 2

Assessment of disease symptoms and viral presence in pSIM1567 plants upon infection with PVY$^{NTN+}$.

| | 2-weeks post infection | | 3 weeks posit infection | |
|---|---|---|---|---|
| Line | symptoms | ELISA | symptoms | ELISA |
| pSIM401 control | Yes | Positive | Yes | Positive |
| 1567-1 | Yes | Positive | Yes | Positive |
| 1567-2 | Yes | Positive | Yes | Positive |
| 1567-3 | Yes | Positive | Yes | Positive |
| 1567-4 | Yes | Positive | Yes | Positive |
| 1567-5 | Yes | Positive | Yes | Positive |
| 1567-6 | Yes | Positive | Yes | Positive |
| 1567-7 | Yes | Positive | Yes | Positive |
| 1567-8 | Yes | Positive | Yes | Positive |
| 1567-9 | Yes | Positive | Yes | Positive |
| 1567-10 | Yes | Positive | Yes | Positive |
| 1567-11 | Yes | Positive | Yes | Positive |
| 1567-12 | Yes | Positive | Yes | Positive |
| 1567-13 | Yes | Positive | Yes | Positive |
| 1567-14 | Yes | Positive | Yes | Positive |
| 1567-15 | No | Positive | Yes | Positive |
| 1567-16 | Yes | Positive | Yes | Positive |
| 1567-17 | Yes | Positive | Yes | Positive |
| 1567-18 | Yes | Positive | Yes | Positive |
| 1567-19 | Yes | Positive | Yes | Positive |
| 1567-20 | Yes | Positive | Yes | Positive |
| 1567-21 | Yes | Positive | Yes | Positive |
| 1567-22 | Yes | Positive | Yes | Positive |
| 1567-23 | Yes | Positive | Yes | Positive |
| 1567-24 | Yes | Positive | Yes | Positive |
| 1567-25 | No | Positive | Yes | Positive |

TABLE 3

Assessment of disease symptoms and viral presence in 1567-25 plants retransformed with pSIM1895 upon infection with PVY$^{NTN+}$.

| | 2-weeks post infection | | 3 weeks posit infection | | 4 weeks posit infection | |
|---|---|---|---|---|---|---|
| Line | symptoms | ELISA | symptoms | ELISA | symptoms | ELISA |
| pSIM401 control | Yes | Positive | Yes | Positive | N/A | Positive |
| 1567-25/1895-1 | No | Negative | No | Positive | N/A | Positive |
| 1567-25/1895-2 | No | Negative | No | Positive | N/A | Positive |
| 1567-25/1895-3 | No | Positive | Yes | Positive | N/A | Positive |
| 1567-25/1895-4 | Yes | Positive | Yes | Positive | N/A | Positive |
| 1567-25/1895-5 | Yes | Positive | Yes | Positive | N/A | Positive |
| 1567-25/1895-6 | No | Negative | No | Negative | No | Positive |
| 1567-25/1895-7 | No | Negative | No | Negative | No | Negative |
| 1567-25/1895-8 | No | Negative | No | Negative | No | Negative |
| 1567-25/1895-9 | No | Negative | Yes | Positive | N/A | Positive |

TABLE 4

| Assessment of disease symptoms and viral presence in pSIM1569 plants upon infection with PVY$^{NTN+}$. | | | | | | |
|---|---|---|---|---|---|---|
| | 2-weeks post infection | | 3 weeks posit infection | | 4 weeks posit infection | |
| Line | symptoms | ELISA | symptoms | ELISA | symptoms | ELISA |
| pSIM401 control | Yes | Positive | Yes | Positive | N/A | Positive |
| 1569-1 | Yes | Positive | Yes | Positive | N/A | Positive |
| 1569-2 | Yes | Positive | Yes | Positive | N/A | Positive |
| 1569-3 | Yes | Positive | Yes | Positive | N/A | Positive |
| 1569-4 | Yes | Positive | Yes | Positive | N/A | Positive |
| 1569-5 | Yes | Positive | Yes | Positive | N/A | Positive |
| 1569-6 | Yes | Positive | Yes | Positive | N/A | Positive |
| 1569-7 | Yes | Positive | Yes | Positive | N/A | Positive |
| 1569-8 | Yes | Positive | Yes | Positive | N/A | Positive |
| 1569-9 | No | Negative | Yes | Positive | Yes | Positive |
| 1569-10 | Yes | Positive | Yes | Positive | N/A | Positive |
| 1569-11 | Yes | Positive | Yes | Positive | N/A | Positive |
| 1569-12 | Yes | Positive | Yes | Positive | N/A | Positive |
| 1569-13 | Yes | Positive | Yes | Positive | N/A | Positive |
| 1569-14 | Yes | Positive | Yes | Positive | N/A | Positive |
| 1569-15 | Yes | Positive | Yes | Positive | N/A | Positive |
| 1569-16 | No | Negative | No | Negative | Yes | Positive |
| 1569-17 | Yes | Positive | Yes | Positive | N/A | Positive |
| 1569-18 | Yes | Positive | Yes | Positive | N/A | Positive |
| 1569-19 | Yes | Positive | Yes | Positive | N/A | Positive |
| 1569-20 | Yes | Positive | Yes | Positive | N/A | Positive |
| 1569-21 | Yes | Positive | Yes | Positive | N/A | Positive |
| 1569-22 | Yes | Positive | Yes | Positive | N/A | Positive |
| 1569-23 | No | Negative | No | Negative | Yes | Positive |
| 1569-24 | Yes | Positive | Yes | Positive | N/A | Positive |
| 1569-25 | No | Negative | Yes | Positive | Yes | Positive |

List of SEQ ID NOs:

SEQ ID NO: 1 (pwp1 full length polynucleotide sequence)
SEQ ID NO: 2 (pwp1 full length amino acid sequence)
SEQ ID NO: 3 (pwp2 full length polynucleotide sequence)
SEQ ID NO:4 (pwp2 full length amino acid sequence)
SEQ ID NO: 5 (eIF4E gene polynucleotide sequence from potato)
SEQ ID NO: 6 (potato eIF4E gene, allele 1, amino acid sequence)
SEQ ID NO: 7 (35S promoter)
SEQ ID NO: 8 (ubi3 terminator)
SEQ ID NO: 9 (Pat promoter)
SEQ ID NO: 10 (EIF4E leader and trailer)
SEQ ID NO: 11 (all-native transfer DNA for PVY resistance)
SEQ ID NO: 12 (primer for amplifying pvr1-2)
SEQ ID NO: 13 (primer for amplifying pvr1-2)
SEQ ID NO: 14 (pvr1-2 cDNA sequence, full length)
SEQ ID NO: 15 (pvr1-2-derived fragment, polynucleotide sequence)
SEQ ID NO: 16 (pvr1-2-derived fragment, amino acid sequence)
SEQ ID NO: 17 (amino acid sequence of deleted potato fragment with mutations)
SEQ ID NO: 18 (DNA sequence of deleted potato fragment with pvr1-2mutations)
SEQ ID NO: 19 (DNA sequence of deleted potato fragment with pwp1 mutations)
SEQ ID NO: 20 (amino acid sequence of deleted potato fragment with pwp1 mutations)
SEQ ID NO: 21 (amino acid sequence of deleted potato fragment with pwp2 mutations)
SEQ ID NO: 22 (DNA sequence of deleted potato fragment with pwp2 mutations)
SEQ ID NO: 23 (amino acid sequence of deleted potato fragment with mpe mutations)
SEQ ID NO: 24 (DNA sequence of deleted potato fragment with mpe mutations)
SEQ ID NO: 25 (The consensus sequence)
SEQ ID NO: 26 (modified CaeIF4E, mpe, DNA sequence 1)
SEQ ID NO: 27 (modified CaeIF4E, mpe, amino acid sequence 1)
SEQ ID NO: 28 (modified CaeIF4E, mpe, DNA sequence 2)
SEQ ID NO: 29 (modified CaeIF4E, amino acid sequence 2)
SEQ ID NO: 30 (modified StEIF4E, DNA sequence)
SEQ ID NO: 31 (modified StEIF4E, amino acid sequence)
SEQ ID NO: 32 (pvr1-2 amino acid sequence)
SEQ ID NO: 33 (Potato border-like sequence)
SEQ ID NO: 34 (consensus sequence of the border-like sequence)
SEQ ID NO: 35 (potato eIF4E gene, allele 2, amino acid sequence)

SEQ ID NO: 1 (pwp1)

```
ATGGCAGCAGCTGAAATGGAGAGAACGACGTCGTTTGATGCAGCTGAGAAGTTGAAGGCCGCCGATGCAGGAGGA

GGAGAGGTAGACGATGAACTTGAAGAAGGTGAAATTGTTGAAGAATCAAATGATGCGGCGTCGTATTTGGGGAAA

GAAATCACAGTGAAGCATCCATTGGAGCATTCATGGACTTTTTGGTTTGATAACCCTACTGCTAGATCTCGACAA

ATTGATTGGGGAAGCTCACTTCGAAATGTCTACACTTTCTCCACTGTTGAAGATTTTTGGGGTGCTTACAATAAT

ATCCATCACCCAAGCAAGTTGGTTATGGGAGCAGACTTTCATTGTTTTAAGCATAAAATTGAGCCAAAGTGGGAA
```

-continued

GATCCTATATGTTCCAATGGAGGGACGTGGAAAATGAGTTTTTCGAAGGGTAAATCTGATACCAGCTGGCTATAT

ACGCTGCTGGCAATGATTGGACATCAATTCGATCATGGAGATGAAATTTGTGGAGCAGTCGTTAATGTCCGGGTT

AAGGGAGAAAAAATAGCTTTGTGGACCAAGAATGCTGCAAATGAAACAGCTCAGGTTAGCATTGGTAAGCAATGG

AAGCAGTTTCTAGATTACAGCGATTCGGTTGGCTTCATATTTCATGACGATGCAAAGAGGCTCGACAGAAATGCC

AAGAATCGTTACACAGTATAG

SEQ ID NO: 2 (pwp1 protein)

MAAAEMERTTSFDAAEKLKAADAGGGEVDDELEEGEIVEESNDAASYLGKEITVKHPLEHSWTFWFDNPTARSRQ

IDWGSSLRNVYTFSTVEDFWGAYNNIHHPSKLVMGADFHCFKHKIEPKWEDPICSNGGTWKMSFSKGKSDTSWLY

TLLAMIGHQFDHGDEICGAVVNVRVKGEKIALWTKNAANETAQVSIGKQWKQFLDYSDSVGFIFHDDAKRLDRNA

KNRYTV

SEQ ID No 3 (pwp2 DNA sequence)

ATGGCAGCAGCTGAAATGGAGAGAACGATGTCGTTTGATGCAGCTGAGAAGCTGAAGGCCGCCGATGGAGGAGGA

GGGGAGGTAGACGATGAACTTGAAGAAGGTGAAATTGTTGAAGAATCAAATGATACGGCGTCGTTTTTAGGGAAA

GAAATCACAGTGAAGCATCCATTGGAGCATTCATGGACTTTTTGGTTTGATAGCCCTATTGCTAAATCTCGACAA

ACTGCTTGGGGAAGCTCACTTCGAAATGTCTACACTTTCTCCACTGTTGAAGATTTTTGGGGTGCTTACTATAAT

ATCCATCACCCAAGCAAGTTGGTTATGGGAGCAGACTTTCATTGTTTTAAGCATAAAATTGAGCCAAAGTGGGAA

GATCCTGTATGTGCCAATGGAGGGACGTGGAAAATGAGTTTTCCGAAGGGTAAATCTGATACCAGCTGGCTATAT

ACGCTGCTGGCAATGATTGGACATCAATTCGATCATGGAGATGAAATTTGTGGAGCAGTCGTTAGTGTCCGGGCT

AAGGGAGAAAAAATAGCTTTGTGGACCAAGAATGCTGCAAACGAAACAGCTCAGGTTAGCATTGGCAAACAATGG

AAGCAGTTTCTAGATTACAGCGATTCGGTTGGCTTCATATTTCACGATGATGCAAAGAGGCTCGACAGAAATGCC

AAGAATCGTTACACAGTTAG

SEQ ID No 4 (pwp2 amino acid sequence)

Maaaemertmsfdaaeklkaadggggevddeleegeiveesndtasflgkeitvkhplehswtfwfdspiaksrq tawgsslrnvytfstvedfwgayynihhpsklvmgadfhcfkhkiepkwedpvcanggtwkmsfpkgksdtswly tllamighqfdhgdeicgavvsvrakgekialwtknaanetaqvsigkqwkqfldysdsvgfifhddakrldrna knrytv SEQ ID NO: 5 (eIF4E gene from potato)

ATGGCAGCAGCTGAAATGGAGAGAACGACGTCGTTTGATGCAGCTGAGAAGTTGAAGGCCGCCGATGCAGGAGGA

GGAGAGGTAGACGATGAACTTGAAGAAGGTGAAATTGTTGAAGAATCAAATGATACGGCGTCGTATTTAGGGAAA

GAAATCACAGTGAAACATCCATTGGAGCATTCATGGACTTTTTGGTTTGATAGCCCTATTGCTAAATCTCGACAA

ACTGCTTGGGGAAGCTCACTTCGAAATGTCTACACTTTCTCCACTGTTGAAGATTTTTGGGGTGCTTACAATAAT

ATCCATCACCCAAGCAAGTTGGTTATGGGAGCAGACTTTCATTGTTTTAAGCATAAAATTGAGCCAAAGTGGGAA

GATCCTGTATGTGCCAATGGAGGGACGTGGAAAATGAATTTTTTGAAGGGTAAATCTGATACCAGCTGGCTATAT

ACGCTGCTGGCAATGATTGGACATCAATTCGATCACGGAGATGAAATTTGTGGAGCAGTCGTTAGTGTCCGGTCT

AAGGGAGAAAAAATAGCTTTGTGGACCAAGAATGCTGCAAATGAAACAGCTCAGGTTAGCATTGGTAAGCAATGG

AAGCAGTTTCTAGATTACAGCGATTCGGTTGGCTTCATATTTCACGATGATGCAAAGAGGCTCGACAGAAGTGCC

AAGAATCGTTACACAGTATAG

SEQ ID NO: 6 (eIF4E form potato, allele 1)

MAAAEMERTTSFDAAEKLKAADAGGGEVDDELEEGEIVEESNDTASYLGKEITVKHPLEHSWTFWFDSPIAKSRQ

TAWGSSLRNVYTFSTVEDFWGAYNNIHHPSKLVMGADFHCFKHKIEPKWEDPVCANGGTWKMNFLKGKSDTSWLY

TLLAMIGHQFDHGDEICGAVVSVRSKGEKIALWTKNAANETAQVSIGKQWKQFLDHSDSVGFIFHDDAKRLDRSA

KNRYTV

-continued

SEQ ID No: 7 (35S promoter)

atggtggagcacgacactctcgtctactccaagaatatcaaagatacagtctcagaagaccaaagggctattgag acttttcaacaaagggtaatatcgggaaacctcctcggattccattgcccagctatctgtcacttcatcaaaagg acagtagaaaaggaaggtggcacctacaaatgccatcattgcgataaaggaaaggctatcgttcaagatgcctct gccgacagtggtcccaaagatggacccccacccacgaggagcatcgtggaaaaagaagacgttccaaccacgtct tcaaagcaagtggattgatgtgaacatggtggagcacgacactctcgtctactccaagaatatcaaagatacagt ctcagaagaccaaagggctattgagacttttcaacaaagggtaatatcgggaaacctcctcggattccattgccc agctatctgtcacttcatcaaaaggacagtagaaaaggaaggtggcacctacaaatgccatcattgcgataaagg aaaggctatcgttcaagatgcctctgccgacagtggtcccaaagatggacccccacccacgaggagcatcgtgga aaaagaagacgttccaaccacgtcttcaaagcaagtggattgatgtgatatctccactgacgtaagggatgacgc acaatcccactatccttcgcaagacccttcctctatataaggaagttcatttcatttggagaggacacgctgaaa tcaccagtctctctctacaaatctatctct SEQ ID NO: 8 (ubi3 terminator)

gccaaagcacatacttatcgatttaaatttcatcgaagagattaatatcgaataatcatatacatactttaaata cataacaaattttaaatacatatatctggtatataattaatttttttaaagtcatgaagtatgtatcaaatacaca tatggaaaaaattaactattcataatttaaaaaaatagaaaagatacatctagtgaaattaggtgcatgtatcaaa tacattaggaaaagggcatatatcttgatctagataattaacgattttgatttatgtataatttccaaatgaagg tttatatctacttcagaaataacaatatacttttatcagaacattcaacaaagtaacaaccaactagagtgaaaa atacacattgttctctaaacatacaaaattgagaaaagaatctcaaaatttagagaaacaaatctgaatttctag aagaaaaaaataattatgcactttgctattgctcgaaaaataaatgaaagaaattagactttttttaaaagatgtt agactagatatactcaaaagctatcaaaggagtaatattcttcttacattaagtattttagttacagtcctgtaa ttaaagacacattttagattgtatctaaacttaaatgtatctagaatacatatatttgaatgcatcatatacatg tatccgacacaccaattctcataaaaagcgtaatatcctaaactaatttatccttcaagtcaacttaagcccaat atacattttcatctctaaaggcccaagtggcacaaaatgtcaggcccaattacgaagaaaagggcttgtaaaacc ctaataaagtggcactggcagagcttacactctcattccatcaacaaagaaaccctaaaagccgcagcgccactg atttctctcctccaggcgaagatgcagatcttcgtgaagaccctaacggggaagacgatcaccctagaggttgag tcttccgacaccatcgacaatgtcaaagccaagatccaggacaaggaagggattcccccagaccagcagcgtttg attttcgccggaaagcagcttgaggatggtcgtactcttgccgactacaacatccagaaggagtcaactctccat ctcgtgctccgtctccgtggtggtg SEQ ID No: 9 (Pat promoter)

cacattgattgagttttatatgcaatatagtaataataataatatttcttataaagcaagaggtcaattttttt tattataccaacgtcactaaattatatttgataatgtaaaacaattcaatttttacttaaatatcatgaaataaac tatttttataaccaaattactaaatttttccaataaaaaaaaagtcattaagaagacataaaataaatttgagtaa aaagagtgaagtcgactgactttttttttttttatcataagaaaataaattattaactttaacctaataaaacact aatataatttcatggaatctaatacttacctcttagaaataagaaaaagtgtttctaatagaccctcaatttaca ttaaatattttcaatcaaatttaaataacaaatatcaatatgaggtcaataacaatatcaaaataatatgaaaaa agagcaatacataatataagaaagaagatttaagtgcgattatcaaggtagtattatatcctaatttgctaatat ttaaactcttatatttaaggtcatgttcatgataaacttgaaatgcgctatattagagcatatattaaaataaaa aaatacctaaaataaaattaagttatttttagtatatatttttttacatgacctacatttttctgggtttttcta aaggagcgtgtaagtgtcgacctcattctcctaattttccccaccacataaaaattaaaaaggaaaggtagcttt tgcgtgttgttttggtacactacacctcattattacacgtgtcctcatataattggttaaccctatgaggcggtt tcgtctagagtcggccatgccatctataaaatgaagctttctgcacctcatttttttcatcttctatctgatttc -continued tattataatttctctcaattgccttcaaatttctctttaaggttagaaatcttctctatttttggtttttgtctg tttagattctcgaattagctaatcaggtgctgttatagcccttaattttgagtttttttttcggttgttttgatgg aaaaggcctaaaatttgagtttttttacgttggtttgatggaaaaggcctacaattggagttttccccgttgttt tgatgaaaaagcccctagtttgagatttttttttctgtcgattcgattctaaaggtttaaaattagagtttttaca tttgtttgatgaaaaaggccttaaatttgagtttttccggttgatttgatgaaaaagccctagaatttgtgtttt ttcgtcggtttgattctgaaggcctaaaatttgagtttctccggctgttttgatgaaaaagccctaaatttgagt ttctccggctgttttgatgaaaaagccctaaatttgagtttttttccccgtgttttagattgtttggttttaattc tcgaatcagctaatcagggagtgtgaaaagccctaaaatttgagtttttttcgttgttctgattgttgtttttat gaatttgcagatgcagatctttgtgaaaactctcaccggaaagactatcaccctagaggtggaaagttctgatac aatcgacaacgttaaggctaagatccaggataaggaaggaattcccccggatcagcaaaggcttatcttcgccgg aaagcagttggaggacggacgtactctagctgattacaacatccagaaggagtctaccctccatttggtgctccg tctacgtggaggt SEQ ID No: 10 (EIF4E leader and trailer)

CACCTCCATCAACAATATTCAAAGAGAATTGTACTACAGAGGAATAATAGGGAGCCTGGGGAAGTAATGCAGAAC

ACGCGAATTGTAGAGGCATGGATTCAAACCAAACAATTTTCCGCGATTAGAAAGTGCAAACACCAATACACGAGT

TACTCAAACCAGAAGCTTATCAAATGAGAAACAAAACCAGTGCCTACCAACTTTCCAGTACGAATTGTGTTTCTT

GCATTCCCACATTGCATCAAGAACTAATTTGCTGCTCTGTGGACTGTGGAGCACTTTTTTT

SEQ ID No: 11 (all-native transfer DNA for PVY resistance)

tcgagcacattgattgagttttatatgcaatatagtaataataataatatttcttataaagcaagaggtcaattt ttttttaattataccaacgtcactaaattatatttgataatgtaaaacaattcaattttacttaaatatcatgaa ataaactatttttataaccaaattactaaatttttccaataaaaaaaagtcattaagaagacataaaataaattt gagtaaaaagagtgaagtcgactgacttttttttttttttatcataagaaaataaattattaactttaacctaata aaacactaatataatttcatggaatctaatacttacctcttagaaataagaaaaagtgtttctaatagaccctca atttacattaaatattttcaatcaaatttaaataacaaatatcaatatgaggtcaataacaatatcaaaataata tgaaaaaagagcaatacataatataagaaagaagatttaagtgcgattatcaaggtagtattatatcctaatttg ctaatatttaaactcttatatttaaggtcatgttcatgataaacttgaaatgcgctatattagagcatatattaa aataaaaaaatacctaaaataaaattaagttatttttagtatatattttttttacatgacctacatttttctgggt ttttctaaaggagcgtgtaagtgtcgacctcattctcctaattttccccaccacataaaaattaaaaaggaaagg tagcttttgcgtgttgttttggtacactacacctcattattacacgtgtcctcatataattggttaaccctatga ggcggtttcgtctagagtcggccatgccatctataaaatgaagctttctgcacctcatttttttcatcttctatc tgatttctattataatttctctcaattgccttcaaatttctctttaaggttagaaatcttctctatttttggttt ttgtctgtttagattctcgaattagctaatcaggtgctgttatagcccttaattttgagtttttttttcggttgtc ttgatggaaaaggcctaaaatttgagtttttttacgttggtttgatggaaaaggcctacaattggagttttcccc gttgttttgatgaaaaagcccctagtttgagatttttttttctgtcgattcgattctaaaggtttaaaattagagt ttttacatttgtttgatgaaaaaggccttaaatttgagtttttccggttgatttgatgaaaaagccctagaattt gtgtttttttcgtcggtttgattctgaaggcctaaaatttgagtttctccggctgttttgatgaaaaagccctaaa tttgagtttctccggctgttttgatgaaaaagccctaaatttgagtttttttccccgtgttttagattgtttggtt ttaattctcgaatcagctaatcagggagtgtgaaaagccctaaatttgagtttttttcgttgttctgattgttgt ttttatgaatttgcagatgcagatctttgtgaaaactctcaccggaaagactatcaccctagaggtggaaagttc tgatacaatcgacaacgttaaggctaagatccaggataaggaaggaattcccccggatcagcaaaggcttatctt cgccggaaagcagttggaggacggacgtactctagctgattacaacatccagaaggagtctaccctccatttggt -continued

```
gctccgtctacgtggaggtggatccatggcagcagctgaaatggagagaacgacgtcgtttgatgcagctgagaa
gttgaaggccgccgatgcaggaggaggagaggtagacgatgaacttgaagaaggtgaaattgttgaagaatcaaa
tgatgcggcgtcgtatttggggaaagaaatcacagtgaagcatccattggagcattcatggactttttggtttga
taaccctactgctagatctcgacaaattgattggggaagctcacttcgaaatgtctacactttctccactgttga
agatttttggggtgcttacaataatatccatcacccaagcaagttggttatgggagcagactttcattgttttaa
gcataaaattgagccaaagtgggaagatcctatatgttccaatggagggacgtggaaaatgagtttttcgaaggg
taaatctgataccagctggctatatacgctgctggcaatgattggacatcaattcgatcatggagatgaaatttg
tggagcagtcgttaatgtccgggttaagggagaaaaaatagctttgtggaccaagaatgctgcaaatgaaacagc
tcaggttagcattggtaagcaatggaagcagtttctagattacagcgattcggttggcttcatatttcatgacga
tgcaaagaggctcgacagaaatgccaagaatcgttacacagtatagactagtttttaatgtttagcaaatgtcct
atcagttttctctttttgtcgaacggtaatttagagtttttttgctatatggattttcgtttttgatgtatgtg
acaaccctcgggattgttgatttatttcaaaactaagagttttgcttattgttctcgtctattttggatatcaa
tcttagttttatatcttttctagttctctacgtgttaaatgttcaacacactagcaatttggctgcagcgtatgg
attatggaactatcaagtctgtgggatcgataaatatgcttctcaggaatttgagattttacagtctttatgctc
attgggttgagtataatatagtaaaaaaataggtatcgataccgtcgacctcgatcgagggggggccccacattg
attgagttttatatgcaatatagtaataataataatatttcttataaagcaagaggtcaatttttttttattata
ccaacgtcactaaattatatttgataatgtaaaacaattcaattttacttaaatatcatgaaataaactattttt
ataaccaaattactaaatttttccaataaaaaaaagtcattaagaagacataaaataaatttgagtaaaaagagt
gaagtcgactgactttttttttttatcataagaaaataaattattaactttaacctaataaaacactaatataa
tttcatggaatctaatacttacctcttagaaataagaaaaagtgtttctaatagaccctcaatttacattaaata
ttttcaatcaaatttaaataacaaatatcaatatgaggtcaataacaatatcaaaataatatgaaaaaagagcaa
tacataatataagaaagaagatttaagtgcgattatcaaggtagtattatatcctaatttgctaatatttaaact
cttatatttaaggtcatgttcatgataaacttgaaatgcgctatattagagcatatattaaaataaaaaaatacc
taaaataaaattaagttatttttagtatatattttttacatgacctacatttttctgggtttttctaaaggagc
gtgtaagtgtcgacctcattctcctaattttccccaccacataaaaattaaaaaggaaaggtagcttttgcgtgt
tgttttggtacactacacctcattattacacgtgtcctcatataattggttaaccctatgaggcggtttcgtcta
gagtcggccatgccatctataaaatgaagctttctgcacctcatttttttcatcttctatctgatttctattata
atttctctcaattgccttcaaatttctctttaaggttagaaatcttctctatttttggtttttgtctgtttagat
tctcgaattagctaatcaggtgctgttatagcccttaatttgagtttttttttcggttgttttgatggaaaaggc
ctaaaatttgagtttttttacgttggtttgatggaaaaggcctacaattggagttttccccgttgttttgatgaa
aaagcccctagtttgagatttttttttctgtcgattcgattctaaaggtttaaaattagagtttttacatttgttt
gatgaaaaaggccttaaatttgagtttttccggttgatttgatgaaaaagccctagaatttgtgtttttttcgtcg
gtttgattctgaaggcctaaaatttgagtttctccggctgttttgatgaaaaagccctaaatttgagtttctccg
gctgttttgatgaaaaagccctaaatttgagttttttccccgtgttttagattgtttggttttaattctcgaatc
agctaatcagggagtgtgaaaagccctaaaatttgagttttttttcgttgttctgattgttgtttttatgaatttg
cagatgcagatctttgtgaaaactctcaccggaaagactatcaccctagaggtggaaagttctgatacaatcgac
aacgttaaggctaagatccaggataaggaaggaattcccccggatcagcaaaggcttatcttcgccggaaagcag
ttggaggacggacgtactctagctgattacaacatccagaaggagtctaccctccatttggtgctccgtctacgt
ggaggtggatcccacctccatcaacaatattcaaagagaattgtactacagaggaataatagggagcctggggaa
gtaatgcagaacacgcgaattgtagaggcatggattcaaaccaaacaattttccgcgattagaaagtgcaaacac
caatacacgagttactcaaaccagaagcttatcaaatgagaaacaaaaccagtgcctaccaactttccagtacga
```

-continued attgtgtttcttgcattcccacattgcatcaagaactaatttgctgctctgtggactgtggagcactttttttga attcgtaacttttactcatctcctccaattatttctgatttcatgcatgtttccctacattctattatgaatcgt gttatggtgtataaacgttgtttcatatctcatctcatctattctgattttgattctcttgcctactgaatttga ccctactgtaatcggtgataaatgtgaatgcttcctcttcttcttcttcttctcagaaatcaatttctgttttgt ttttgttcatctgtagccgcggaaaaaaagtgctccacagtccacagagcagcaaaatagttcttgatgcaatgt gggaatgcaagaaacacaattcgtactggaaagttggtaggcactggttttgtttctcatttgataagcttctgg tttgagtaactcgtgtattggtgtttgcactttctaatcgcggaaaattgtttggtttgaatccatgcctctaca attcgcgtgttctgcattacttccccaggctccctattattcctctgtagtacaattctctttgaatattgttga tggaggtgactagtcaccaccacggagacggagcacgagatggagagttgactccttctggatgttgtagtcggc aagagtacgaccatcctcaagctgctttccggcgaaaatcaaacgctgctggtctgggggaatcccttccttgtc ctggatcttggctttgacattgtcgatggtgtcggaagactcaacctctagggtgatcgtcttccccgttagggt cttcacgaagatctgcatcttcgcctggaggagagaaatcagtggcgctgcggcttttagggtttctttgttgat ggaatgagagtgtaagctctgccagtgccactttattagggttttacaagcccttttcttcgtaattgggcctga cattttgtgccacttgggcctttagagatgaaaatgtatattgggcttaagttgacttgaaggataaattagttt aggatattacgctttttatgagaattggtgtgtcggatacatgtatatgatgcattcaaatatatgtattctaga tacatttaagtttagatacaatctaaaatgtgtctttaattacaggactgtaactaaaatacttaatgtaagaag aatattactcctttgatagcttttgagtatatctagtctaacatcttttaaaaaagtctaatttctttcatttat ttttcgagcaatagcaaagtgcataattatttttttcttctagaaattcagatttgtttctctaaattttgagat tcttttctcaattttgtatgtttagagaacaatgtgtatttttcactctagttggttgttactttgttgaatgtt ctgataaaagtatattgttatttctgaagtagatataaaccttcatttggaaattatacataaatcaaaatcgtt aattatctagatcaagatatatgcccttttcctaatgtatttgatacatgcacctaatttcactagatgtatctt ttctatttttaaattatgaatagttaatttttccatatgtgtatttgatacatacttcatgactttaaaaaat taattatataccagatatatgtatttaaaatttgttatgtatttaaagtatgtatatgattattcgatattaatc tcttcgatgaaatttaaatcgataagtatgtgctttggc SEQ ID No 12

GATTGGGGATCCATGGCAAAGCATCCATTAGAGCAT

SEQ ID No 13

ATGCTCTAATGGATGCTTTGCCATGGATCCCCAATC

SEQ ID No 14 (pvr1-2 cDNA)

ATGGCAACAGCTGAAATGGAGAAAACGACGACGTTTGATGAAGCTGAGAAGGTGAAATTGAATGCTAATGAGGCA

GATGATGAAGTTGAAGAAGGTGAAATTGTTGAAGAAACTGATGATACGACGTCGTATTTGAGCAAAGAAATAGCA

ACAAAGCATCCATTAGAGCATTCATGGACTTTCTGGTTTGATAATCCAGAGGCGAAATCGAAACAAGCTGCTTGG

GGTAGCTCGCGTCGCAACGTCTACACTTTCTCCACTGTTGAAGATTTTTGGGGTGCTTACAATAATATCCACCAC

CCAAGCAAGTTAGTTGTGGGAGCAGACTTACATTGTTTCAAGCATAAAATTGAGCCAAAGTGGGAAGATCCTGTA

TGTGCCAATGGAGGGACATGGAAAATGAGTTTTTCAAAGGGTAAATCTGATACCAGCTGGCTATATACGCTGCTT

GCAATGATTGGACATCAATTCGATCATGAAGATGAAATTTGTGGAGCAGTAGTTAGTGTCAGAGGTAAGGGAGAA

AAAATATCTTTGTGGACCAAGAATGCTGCAAATGAAACGGCTCAGGTTAGCATTGGTAAGCAATGGAAGCAGTTT

CTGGATTACAGCGACAGTGTTGGCTTCATATTTCACGACGATGCAAAGAGGCTCGACAGAAATGCAAAGAATCGT

TACACAGTATAA

SEQ ID No 15 (pvr1-2-derived fragment)

ATGGCAAAGCATCCATTAGAGCATTCATGGACTTTCTGGTTTGATAATCCAGAGGCGAAATCGAAACAAGCTGCT

TGGGGTAGCTCGCGTCGCAACGTCTACACTTTCTCCACTGTTGAAGATTTTTGGGGTGCTTACAATAATATCCAC

-continued

CACCCAAGCAAGTTAGTTGTGGGAGCAAACTTACATTGTTTCAAGCATAAAATTGAGCCAAAGTGGGAAGATCCT

GTATGTGCCAATGGAGGGACATGGAAAATGAGTTTTTCAAAGGGTAAATCTGATACCAGCTGGCTATATACGCTG

CTTGCAATGATTGGACATCAATTCGATCATGAAGATGAAATTTGTGGAGCAGTAGTTAGTGTCAGAGGTAAGGGA

GAAAAAAATATCTTTGTGGACCAAGAATGCTGCAAATGAAACGGCTCAGGTTAGCATTGGTAAGCAATGGAAGCAG

TTTCTGGATTACAGCGACAGTGTTGGCTTCATATTTCACGACGATGCAAAGAGGCTCGACAGAAATGCAAAGAAT

CGTTACACCGTATAG

SEQ ID No 16 (amino acid sequence of the purl-2-derived fragment)

MATKHPLEHSWTFWFDNPEAKSKQAAWGSSRRNVYTFSTVEDFWGAYNNIHHPSKLVVGANLHCFKHKIEPKWED

PVCANGGTWKMSFSKGKSDTSWLYTLLAMIGHQFDHEDEICGAVVSVRGKGEKISLWTKNAANETAQVSIGKQWK

QFLDYSDSVGFIFHDDAKRLDRNAKNRYTV

Seq ID NO 17 (Amino acid sequence of deleted potato fragment with pvr1-2 mutations)

MAKHPLEHSWTFWFDSPEAKSRQTAWGSSRRNVYTFSTVEDFWGAYNNIHHPSKLVMGANFHCFKHKIEPKWEDP

VCANGGTWKMNFLKGKSDTSWLYTLLAMIGHQFDHGDEICGAVVSVRSKGEKIALWTKNAANETAQVSIGKQWKQ

FLDYSDSVGFIFHDDAKRLDRSAKNRYTV*

Seq ID NO 18 (DNA sequence of deleted potato fragment with pvr1-2 mutations)

ATGGCAAAACATCCATTGGAGCATTCATGGACTTTTTGGTTTGATAGCCCTGAAGCTAAATCTCGACAAACTGCT

TGGGGAAGCTCAAGACGAAATGTCTACACTTTCTCCACTGTTGAAGATTTTTGGGGTGCTTACAATAATATCCAT

CACCCAAGCAAGTTGGTTATGGGAGCAAACTTTCATTGTTTTAAGCATAAAATTGAGCCAAAGTGGGAAGATCCT

GTATGTGCCAATGGAGGGACGTGGAAAATGAATTTTTTGAAGGGTAAATCTGATACCAGCTGGCTATATACGCTG

CTGGCAATGATTGGACATCAATTCGATCACGGAGATGAAATTTGTGGAGCAGTCGTTAGTGTCCGGTCTAAGGGA

GAAAAAATAGCTTTGTGGACCAAGAATGCTGCAAATGAAACAGCTCAGGTTAGCATTGGTAAGCAATGGAAGCAG

TTTCTAGATTACAGCGATTCGGTTGGCTTCATATTTCACGATGATGCAAAGAGGCTCGACAGAAGTGCCAAGAAT

CGTTACACAGTATAG

SEQ ID NO: 19 (DNA sequence of deleted potato fragment with pwp1 mutations)

ATGGCAAAGCATCCATTGGAGCATTCATGGACTTTTTGGTTTGATAACCCTACTGCTAGATCTCGACAAATTGAT

TGGGGAAGCTCACTTCGAAATGTCTACACTTTCTCCACTGTTGAAGATTTTTGGGGTGCTTACAATAATATCCAT

CACCCAAGCAAGTTGGTTATGGGAGCAGACTTTCATTGTTTTAAGCATAAAATTGAGCCAAAGTGGGAAGATCCT

ATATGTTCCAATGGAGGGACGTGGAAAATGAGTTTTTCGAAGGGTAAATCTGATACCAGCTGGCTATATACGCTG

CTGGCAATGATTGGACATCAATTCGATCATGGAGATGAAATTTGTGGAGCAGTCGTTAATGTCCGGGTTAAGGGA

GAAAAAATAGCTTTGTGGACCAAGAATGCTGCAAATGAAACAGCTCAGGTTAGCATTGGTAAGCAATGGAAGCAG

TTTCTAGATTACAGCGATTCGGTTGGCTTCATATTTCATGACGATGCAAAGAGGCTCGACAGAAATGCCAAGAAT

CGTTACACAGTATAG

SEQ ID NO: 20(amino acid sequence of deleted potato fragment with pwp1 mutations)

MAKHPLEHSWTFWFDNPTARSRQIDWGSSLRNVYTFSTVEDFWGAYNNIHHPSKLVMGADFHCFKHKIEPKWEDP

ICSNGGTWKMSFSKGKSDTSWLYTLLAMIGHQFDHGDEICGAVVNVRVKGEKIALWTKNAANETAQVSIGKQWKQ

FLDYSDSVGFIFHDDAKRLDRNAKNRYTV

Seq ID No 21 (Amino acid sequence of deleted potato fragment with pwp2 mutations)

MAKHPLEHSWTFWFDSPIAKSRQTAWGSSLRNVYTFSTVEDFWGAYYNIHHPSKLVMGADFHCFKHKIEPKWEDP

VCANGGTWKMSFPKGKSDTSWLYTLLAMIGHQFDHGDEICGAVVSVRAKGEKIALWTKNAANETAQVSIGKQWKQ

FLDYSDSVGFIFHDDAKRLDRNAKNRYTV

Seq ID No 22 (DNA sequence of deleted potato fragment with pwp2 mutations)

ATGGCAAAGCATCCATTGGAGCATTCATGGACTTTTTGGTTTGATAGCCCTATTGCTAAATCTCGACAAACTGCT

-continued

TGGGGAAGCTCACTTCGAAATGTCTACACTTTCTCCACTGTTGAAGATTTTTGGGGTGCTTACTATAATATCCAT

CACCCAAGCAAGTTGGTTATGGGAGCAGACTTTCATTGTTTTAAGCATAAAATTGAGCCAAAGTGGGAAGATCCT

GTATGTGCCAATGGAGGGACGTGGAAAATGAGTTTTCCGAAGGGTAAATCTGATACCAGCTGGCTATATACGCTG

CTGGCAATGATTGGACATCAATTCGATCATGGAGATGAAATTTGTGGAGCAGTCGTTAGTGTCCGGGCTAAGGGA

GAAAAAATAGCTTTGTGGACCAAGAATGCTGCAAACGAAACAGCTCAGGTTAGCATTGGCAAACAATGGAAGCAG

TTTCTAGATTACAGCGATTCGGTTGGCTTCATATTTCACGATGATGCAAAGAGGCTCGACAGAAATGCCAAGAAT

CGTTACACAGTTAG

Seq ID No 23 (Amino acid sequence of deleted potato fragment with mpe mutations)

MAKHPLEHSWTFWFDSPIPKSRQTAWGSSLRNVYTFSTVEDFWGAYNNIHHPSKLVHDFHCFKHKIEPKWEDPVC

ANGGTWKMNFLKGKSDTSWLYTLLAMIGHQFDHGDEICGAVVSVRSKGEKIALWTKNSANETAQVSIGKQWKQFL

DYSDSVGFIFHDDAKRLDRSAKNRYTV*

Seq ID No 24 (DNA sequence of deleted potato fragment with mpe mutations)

ATGGCAAAACATCCATTGGAGCATTCATGGACTTTTTGGTTTGATAGCCCTATTCCTAAATCTCGACAAACTGCT

TGGGGAAGCTCACTTCGAAATGTCTACACTTTCTCCACTGTTGAAGATTTTTGGGGTGCTTACAATAATATCCAT

CACCCAAGCAAGTTGGTTCACGACTTTCATTGTTTTAAGCATAAAATTGAGCCAAAGTGGGAAGATCCTGTATGT

GCCAATGGAGGGACGTGGAAAATGAATTTTTTGAAGGGTAAATCTGATACCAGCTGGCTATATACGCTGCTGGCA

ATGATTGGACATCAATTCGATCACGGAGATGAAATTTGTGGAGCAGTCGTTAGTGTCCGGTCTAAGGGAGAAAAA

ATAGCTTTGTGGACCAAGAATAGTGCAAATGAAACAGCTCAGGTTAGCATTGGTAAGCAATGGAAGCAGTTTCTA

GATTACAGCGATTCGGTTGGCTTCATATTTCACGATGATGCAAAGAGGCTCGACAGAAGTGCCAAGAATCGTTAC

ACAGTATAG

SEQ ID No 25

DXXXXKSBQXAWGSSXRXXYTFSXVEXFWXXYNNIHBPSKLXXGAD

SEQ ID No 26 (modified CaeIF4E, DNA sequence 1)

ATGGCAACAGCTGAAATGGAGAAAACGACGACGTTTGATGAAGCTGAGAAGGTGAAATTGAATGCTAATGAGGCA

GATGATGAAGTTGAAGAAGGTGAAATTGTTGAAGAAACTGATGATACGACGTCGTATTTGAGCAAAGAAATAGCA

ACAAAGCATCCATTAGAGCATTCATGGACTTTCTGGTTTGATAATCCAGTGCCGAAATCGAAACAAGCTGCTTGG

GGTAGCTCGCTTCGCAACGTCTACACTTTCTCCACTGTTGAAGATTTTTGGGGTGCTTACAATAATATCCACCAC

CCAAGCAAGTTAGTTCACGACTTACATTGTTTCAAGCATAAAATTGAGCCAAAGTGGGAAGATCCTGTATGTGCC

AATGGAGGGACATGGAAAATGAGTTTTTCAAAGGGTAAATCTGATACCAGCTGGCTATATACGCTGCTTGCAATG

ATTGGACATCAATTCGATCATGAAGATGAAATTTGTGGGGCAGTAGTTAGTGTCAGAGGTAAGGGAGAAAAAATA

TCTTTGTGGACCAAGAATTCTGCAAATGAAACGGCTCAGGTTAGCATTGGTAAGCAATGGAAGCAGTTTCTGGAT

TACAGCGACAGTGTTGGCTTCATATTTCACGACGATGCAAAGAGGCTCGACAGAAATGCAAAGAATCGTTACACC

GTATAG

SEQ ID No 27(modified CaeIF4E, amino acid sequence 1)

MATAEMEKTTTFDEAEKVKLNANEADDEVEEGEIVEETDDTTSYLSKEIATKHPLEHSWTFWFDNPVPKSKQAAW

GSSLRNVYTFSTVEDFWGAYNNIHHPSKLVHDLHCFKHKIEPKWEDPVCANGGTWKMSFSKGKSDTSWLYTLLAM

IGHQFDHEDEICGAVVSVRGKGEKISLWTKNSANETAQVSIGKQWKQFLDYSDSVGFIFHDDAKRLDRNAKNRYT

V

SEQ ID No 28 (modified CaeIF4E, DNA sequence 2)

ATGGCAACAGCTGAAATGGAGAAAACGACGACGTTTGATGAAGCTGAGAAGGTGAAATTGAATGCTAATGAGGCA

GATGATGAAGTTGAAGAAGGTGAAATTGTTGAAGAAACTGATGATACGACGTCGTATTTGAGCAAAGAAATAGCA

ACAAAGCATCCATTAGAGCATTCATGGACTTTCTGGTTTGATAATCCAGTGCCGAAATCGAAACAAGCTGCTTGG

GGTAGCTCGCTTCGCAACGTCTACACTTTCTCCACTGTTGAAGATTTTTGGGGTGCTTACAATAATATCCACCAC

-continued

CCAAGCAAGTTAGTTCACGACTTACATTGTTTCAAGCATAAAATTGAGCCAAAGTGGGAAGATCCTGTATGTGCC

AATGGAGGGACATGGAAAATGAGTTTTTCAAAGGGTAAATCTGATACCAGCTGGCTATATACGCTGCTTGCAATG

ATTGGACATCAATTCGATCATGAAGATGAAATTTGTGGGGCAGTAGTTAGTGTCAGAGGTAAGGGAGAAAAAATA

TCTTTGTGGACCAAGAATTCTGCAAATGAAACGGCTCAGGTTAGCATTGGTAAGCAATGGAAGCAGTTTCTGGAT

TACAGCGACAGTGTTGGCTTCATATTTCACGACGATGCAAAGAGGCTCGACAGAAATGCAAAGAATCGTTACACC

GTATAG

SEQ ID No 29 (modified CaeIF4E, amino acid sequence 2)

MATAEMEKTTTFDEAEKVKLNANEADDEVEEGEIVEETDDTTSYLSKEIATKHPLEHSWT

FWFDNPVPKSKQAAWGSSLRNVYTFSTVEDFWGAYNNIHHPSKLVHDLHCFKHKIEPKWE

DPVCANGGTWKMSFSKGKSDTSWLYTLLAMIGHQFDHEDEICGAVVSVRGKGEKISLWTK

NSANETAQVSIGKQWKQFLDYSDSVGFIFHDDAKRLDRNAKNRYTV

SEQ ID No 30 (modified StEIF4E, DNA sequence)

ATGGCAGCAGCTGAAATGGAGAGAACGACGTCGTTTGATGCAGCTGAGAAGTTGAAGGCCGCCGATGCAGGAGGA

GGAGAGGTAGACGATGAACTTGAAGAAGGTGAAATTGTTGAAGAATCAAATGATACGGCGTCGTATTTAGGGAAA

GAAATCACAGTGAAACATCCATTGGAGCATTCATGGACTTTTTGGTTTGATAGCCCTATTCCTAAATCTCGACAA

ACTGCTTGGGGAAGCTCACTTCGAAATGTCTACACTTTCTCCACTGTTGAAGAGTTTTGGGGTGCTTACAATAAT

ATCCATCACCCAAGCAAGTTGGTTCACGACTTTCATTGTTTTAAGCATAAAATTGAGCCAAAGTGGGAAGATCCT

GTATGTGCCAATGGAGGGACGTGGAAAATGAATTTTTTGAAGGGTAAATCTGATACCAGCTGGCTATATACGCTG

CTGGCAATGATTGGACATCAATTCGATCACGGAGATGAAATTTGTGGAGCAGTCGTTAGTGTCCGGTCTAAGGGA

GAAAAAATAGCTTTGTGGACCAAGAATACTGCAAATGAAACAGCTCAGGTTAGCATTGGTAAGCAATGGAAGCAG

TTTCTAGATTACAGCGATTCGGTTGGCTTCATATTTCACGATGATGCAAAGAGGCTCGACAGAAGTGCCAAGAAT

CGTTATTCCGTGTAG

SEQ ID No 31 (modified StEIF4E, amino acid sequence)

MAAAEMERTTSFDAAEKLKAADAGGGEVDDELEEGEIVEESNDTASYLGKEITVKHPLEH

SWTFWFDSPIPKSRQTAWGSSLRNVYTFSTVEEFWGAYNNIHHPSKLVHDFHCFKHKIEP

KWEDPVCANGGTWKMNFLKGKSDTSWLYTLLAMIGHQFDHGDEICGAVVSVRSKGEKIAL

WTKNTANETAQVSIGKQWKQFLDYSDSVGFIFHDDAKRLDRSAKNRYSV

SEQ ID NO: 32 (pvr1-2 amino acid sequence)

MATAEMEKTTTFDEAEKVKLNANEADDEVEEGEIVEETDDTTSYLSKEIATKHPLEHSWT

FWFDNPEAKSKQAAWGSSRRNVYTFSTVEDFWGAYNNIHHPSKLVVGADLHCFKHKIEPK

WEDPVCANGGTWKMSFSKGKSDTSWLYTLLAMIGHQFDHEDEICGAVVSVRGKGEKISLW

TKNAANETAQVSIGKQWKQFLDYSDSVGFIFHDDAKRLDRNAKNRYTV*

SEQ ID NO: 33 (Potato border-like sequence)

GTTTACAGTACCATATATCCTGTCAGAGGTATAGAGGCATGACTGGCATGATCACTAAATTGATGCCCACAGAGG

AGACTTATAACCTACAGGGGCACGTAGTTCTAGGACTTGAAAGTGACTGACCGTAGTCCAACTCGGTATAAAGCC

TACTCCCAACTAAATATATGAAATTTATAGCATAACTGCAGATGAGCTCGATTCTAGAGTAGGTACCGAGCTCGA

ATTCCTTACTCCTCCACAAAGCCGTAACTGAAGCGACTTCTATTTTTCTCAACCTTCGGACCTGACGATCAAGAA

TCTCAATAGGTAGTTCTTCATAAGTGAGACTATCCTTCATAGCTACACTTTCTAAAGGTACGATAGATTTTGGAT

CAACCACACACACTTCGTTTACACCGGTATATATCCTGCCA

SEQ ID NO: 34 (consensus sequence of the border-like sequence)

YGRYAGGATATATWSNVBKGTAAWY

SEQ ID NO: 35 (potato eIF4E gene, allele 2, amino acid sequence)

MAAAEMERTTSFDAA<u>D</u>KLKAADAGGGEVDDELEEGEIVEESNDTASYLGKEITVKHPLEHSWTFWFDSPIAKSRQ

-continued

TAWGSSLRNVYTFSTVEDFWGAYNNIHHPSKLVMGADFHCFKHKIEPKWEDPVCANGGTWKMSFSKGKSDTSWLY

TPLAMIGHQFDHGDEICGAVVSVRAKGEKIALWTKNAANETAQVSIGKQWKQFLDYSDSVGFIFHDDAKRLDRNA

KNRYTV

What is claimed is:

1. A method for conferring PVY resistance to a *Solanum tuberosum* plant, said method comprising:

(A) transforming the *Solanum tuberosum* plant with an *Agrobacterium* transfer-DNA comprising at least one of (i) a polynucleotide encoding SEQ ID NO: 2, or (ii) a polynucleotide encoding SEQ ID NO: 4, and (B) expressing said polynucleotide in a cell of the plant, wherein said resistance comprises a delay in the onset of one or more symptoms of PVY disease for a period of time of at least one day compared to a *Solanum tuberosum* plant lacking said polynucleotide.

2. The method of claim 1, wherein the *Solanum tuberosum* plant is transformed with the *Agrobacterium* transfer-DNA comprising the polynucleotide encoding SEQ ID NO: 2.

3. The method of claim 2, wherein the period of time is selected from the group consisting of: (i) 1-3 days, (ii) 3-5 days, (iii) 5-7 days, (iv) 7-9 days, (v) 9-11 days, (vi) 11-13 days, (vii) 13-15 days, (viii) 2-3 weeks, (ix) 3-4 weeks, (x) 4-5 weeks, (xi) 5-7 weeks, (xii) 7-10 weeks, (xiii) 2-3 months, and (xiv) 3-5 months.

4. The method of claim 2, wherein the plant possesses one or more additional traits selected from the group consisting of: (i) low reducing sugar, (ii) low free asparagines, (iii) low bruising, (iv) reduced cold-induced sweetening, (v) low acrylamide, (vi) resistance to *Phytophthora*, (vii) reduced starch phosphate level, and (viii) increased antioxidant.

5. The method of claim 1, wherein the *Solanum tuberosum* plant is transformed with the *Agrobacterium* transfer-DNA comprising the polynucleotide encoding SEQ ID NO: 4.

6. The method of claim 5, wherein the period of time is selected from the group consisting of: (i) 1-3 days, (ii) 3-5 days, (iii) 5-7 days, (iv) 7-9 days, (v) 9-11 days, (vi) 11-13 days, (vii) 13-15 days, (viii) 2-3 weeks, (ix) 3-4 weeks, (x) 4-5 weeks, (xi) 5-7 weeks, (xii) 7-10 weeks, (xiii) 2-3 months, and (xiv) 3-5 months.

7. The method of claim 5, wherein the plant possesses one or more additional traits selected from the group consisting of: (i) low reducing sugar, (ii) low free asparagines, (iii) low bruising, (iv) reduced cold-induced sweetening, (v) low acrylamide, (vi) resistance to *Phytophthora*, (vii) reduced starch phosphate level, and (viii) increased antioxidant.

8. A method for conferring PVY resistance to a *Solanum tuberosum* plant, said method comprising:

(A) transforming the *Solanum tuberosum* plant with an *Agrobacterium* transfer-DNA comprising at least one of (i) a polynucleotide encoding SEQ ID NO: 2, or (ii) a polynucleotide encoding SEQ ID NO: 4, (B) expressing said polynucleotide in a cell of the plant, and (C) downregulating the expression of the plant's endogenous eIF4E gene, wherein said resistance comprises full resistance to PVY virus infection, or a delay in the onset of one or more symptoms of PVY disease for a period of time of at least one day compared to a *Solanum tuberosum* plant lacking said polynucleotide.

9. The method of claim 8, wherein the *Solanum tuberosum* plant is transformed with the *Agrobacterium* transfer-DNA comprising the polynucleotide encoding SEQ ID NO: 2.

10. The method of claim 9, wherein the period of time is selected from the group consisting of: (i) 1-3 days, (ii) 3-5 days, (iii) 5-7 days, (iv) 7-9 days, (v) 9-11 days, (vi) 11-13 days, (vii) 13-15 days, (viii) 2-3 weeks, (ix) 3-4 weeks, (x) 4-5 weeks, (xi) 5-7 weeks, (xii) 7-10 weeks, (xiii) 2-3 months, and (xiv) 3-5 months.

11. The method of claim 9, wherein the plant possesses one or more additional traits selected from the group consisting of: (i) low reducing sugar, (ii) low free asparagines, (iii) low bruising, (iv) reduced cold-induced sweetening, (v) low acrylamide, (vi) resistance to *Phytophthora*, (vii) reduced starch phosphate level, and (viii) increased antioxidant.

12. The method of claim 8, wherein the *Solanum tuberosum* plant is transformed with the *Agrobacterium* transfer-DNA comprising the polynucleotide encoding SEQ ID NO: 4.

13. The method of claim 12, wherein the period of time is selected from the group consisting of: (i) 1-3 days, (ii) 3-5 days, (iii) 5-7 days, (iv) 7-9 days, (v) 9-11 days, (vi) 11-13 days, (vii) 13-15 days, (viii) 2-3 weeks, (ix) 3-4 weeks, (x) 4-5 weeks, (xi) 5-7 weeks, (xii) 7-10 weeks, (xiii) 2-3 months, and (xiv) 3-5 months.

14. The method of claim 12, wherein the plant possesses one or more additional traits selected from the group consisting of: (i) low reducing sugar, (ii) low free asparagines, (iii) low bruising, (iv) reduced cold-induced sweetening, (v) low acrylamide, (vi) resistance to *Phytophthora*, (vii) reduced starch phosphate level, and (viii) increased antioxidant.

15. A method for conferring PVY resistance to a *Solanum tuberosum* plant, said method comprising expressing at least one of (i) a polynucleotide encoding SEQ ID NO: 2, or (ii) a polynucleotide encoding SEQ ID NO: 4 in a cell of the plant, wherein said resistance comprises a delay in the onset of one or more symptoms of PVY disease for a period of time of at least one day compared to a *Solanum tuberosum* plant lacking said polynucleotide.

16. The method of claim 15, wherein the *Solanum tuberosum* plant expresses the polynucleotide encoding SEQ ID NO: 2.

17. The method of claim 16, wherein the period of time is selected from the group consisting of: (i) 1-3 days, (ii) 3-5 days, (iii) 5-7 days, (iv) 7-9 days, (v) 9-11 days, (vi) 11-13 days, (vii) 13-15 days, (viii) 2-3 weeks, (ix) 3-4 weeks, (x) 4-5 weeks, (xi) 5-7 weeks, (xii) 7-10 weeks, (xiii) 2-3 months, and (xiv) 3-5 months.

18. The method of claim 16, wherein the plant possesses one or more additional traits selected from the group consisting of: (i) low reducing sugar, (ii) low free asparagines, (iii) low bruising, (iv) reduced cold-induced sweetening, (v) low acrylamide, (vi) resistance to *Phytophthora*, (vii) reduced starch phosphate level, and (viii) increased antioxidant.

19. The method of claim 15, wherein the *Solanum tuberosum* plant expresses the polynucleotide encoding SEQ ID NO: 4.

20. The method of claim 19, wherein the period of time is selected from the group consisting of: (i) 1-3 days, (ii) 3-5 days, (iii) 5-7 days, (iv) 7-9 days, (v) 9-11 days, (vi) 11-13 days, (vii) 13-15 days, (viii) 2-3 weeks, (ix) 3-4 weeks, (x) 4-5 weeks, (xi) 5-7 weeks, (xii) 7-10 weeks, (xiii) 2-3 months, and (xiv) 3-5 months.

21. The method of claim 19, wherein the plant possesses one or more additional traits selected from the group consisting of: (i) low reducing sugar, (ii) low free asparagines, (iii) low bruising, (iv) reduced cold-induced sweetening, (v) low acrylamide, (vi) resistance to *Phytophthora*, (vii) reduced starch phosphate level, and (viii) increased antioxidant.

* * * * *